United States Patent
Buesing et al.

(10) Patent No.: US 10,020,450 B2
(45) Date of Patent: Jul. 10, 2018

(54) MATERIALS FOR ELECTRONIC DEVICES

(71) Applicant: Merck Patent GmbH, Darmstadt (DE)

(72) Inventors: Arne Buesing, Frankfurt am Main (DE); Irina Martynova, Griesheim (DE); Teresa Mujica-Fernaud, Darmstadt (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 367 days.

(21) Appl. No.: 14/443,549

(22) PCT Filed: Oct. 25, 2013

(86) PCT No.: PCT/EP2013/003218
§ 371 (c)(1),
(2) Date: May 18, 2015

(87) PCT Pub. No.: WO2014/078527
PCT Pub. Date: May 30, 2014

(65) Prior Publication Data
US 2015/0318484 A1    Nov. 5, 2015

(30) Foreign Application Priority Data
Nov. 23, 2012 (EP) .................................. 12007922

(51) Int. Cl.
| | |
|---|---|
| *H01L 51/00* | (2006.01) |
| *C07D 209/86* | (2006.01) |
| *C07D 405/12* | (2006.01) |
| *C07D 209/94* | (2006.01) |
| *C08G 61/12* | (2006.01) |
| *C09K 11/06* | (2006.01) |
| *H05B 33/22* | (2006.01) |
| *H01L 51/50* | (2006.01) |

(52) U.S. Cl.
CPC ........ *H01L 51/0061* (2013.01); *C07D 209/86* (2013.01); *C07D 209/94* (2013.01); *C07D 405/12* (2013.01); *C08G 61/124* (2013.01); *C08G 61/125* (2013.01); *C09K 11/06* (2013.01); *H01L 51/006* (2013.01); *H01L 51/0035* (2013.01); *H01L 51/0059* (2013.01); *H05B 33/22* (2013.01); *C08G 2261/312* (2013.01); *C08G 2261/3142* (2013.01); *C08G 2261/3241* (2013.01); *C08G 2261/3242* (2013.01); *C08G 2261/512* (2013.01); *C08G 2261/95* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *H01L 51/0052* (2013.01); *H01L 51/0072* (2013.01); *H01L 51/0073* (2013.01); *H01L 51/0085* (2013.01); *H01L 51/506* (2013.01); *H01L 51/5012* (2013.01); *H01L 51/5056* (2013.01); *H01L 51/5064* (2013.01); *H01L 51/5088* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | | | |
|---|---|---|---|---|
| 7,090,930 | B2 * | 8/2006 | Robello | C09K 11/06 257/98 |
| 8,178,215 | B2 * | 5/2012 | Yabe | C07D 401/14 313/502 |
| 2009/0284143 | A1 | 11/2009 | Nomura et al. | |
| 2011/0248247 | A1 | 10/2011 | Matsumoto et al. | |
| 2011/0297924 | A1 * | 12/2011 | Yabunouchi | C07D 209/86 257/40 |
| 2014/0203272 | A1 | 7/2014 | Hong et al. | |

FOREIGN PATENT DOCUMENTS

| | | | | |
|---|---|---|---|---|
| EP | 2399906 | A1 | | 12/2011 |
| EP | 2749625 | A1 | | 7/2014 |
| JP | 2007110093 | A | | 4/2007 |
| JP | 2009016718 | A | * | 1/2009 ............ H01L 51/50 |
| JP | 201083770 | | * | 4/2010 ........... C07D 209/86 |
| JP | 2012062450 | A | | 3/2012 |
| WO | WO-2008127057 | A1 | | 10/2008 |
| WO | WO-2013129835 | A1 | | 9/2013 |

OTHER PUBLICATIONS

Machine translation of JP 2009-016718, translation generated Oct. 2017. (Year: 2017).*
International Search Report for PCT/EP2013/003218 dated Dec. 20, 2013.
European Patent Office for Application No. 13 782 978.4, dated Mar. 8, 2017.

* cited by examiner

*Primary Examiner* — Robert S Loewe
(74) *Attorney, Agent, or Firm* — Drinker Biddle & Reath LLP

(57) ABSTRACT

The present application relates to a compound according to formula (I), and the use thereof as a functional material in an electronic device. The compound according to formula (I) is preferably used as a hole-transporting material in an organic electroluminescence device (OLED).

12 Claims, No Drawings

MATERIALS FOR ELECTRONIC DEVICES

CROSS-REFERENCE TO RELATED APPLICATIONS

This application is a national stage application (under 35 U.S.C. § 371) of PCT/EP2013/003218, filed Oct. 25, 2013, which claims benefit of European Application No. 12007922.3, filed Nov. 23, 2012, both of which are incorporated herein by reference in their entirety.

The present application relates to a compound of the formula (I) which contains a carbazole unit and an arylamino unit. The compound is suitable for use as functional material in an electronic device, preferably as functional material having hole-transporting properties. The present application furthermore relates to a process for the preparation of the compound of the formula (I).

Electronic devices in the sense of this application are taken to mean, in particular, so-called organic electronic devices, which comprise organic semiconductor materials as functional materials. They are more particularly taken to mean organic electroluminescent devices (OLEDs) and other electronic devices which are indicated below in the detailed description of the invention.

The precise structure of OLEDs is described, inter alia, in U.S. Pat. No. 4,539,507, U.S. Pat. No. 5,151,629, EP 0676461 and WO 98/27136. In general, the term OLED is taken to mean electronic devices which comprise at least one organic material and emit light on application of an electrical voltage.

In the case of electronic devices, in particular OLEDs, there is great interest in improving the performance data, in particular lifetime and efficiency and operating voltage. An important role is played here by layers having a hole-transporting function in the electronic device. There is furthermore great interest in the provision of compounds having advantageous glass formation properties, in particular a high glass transition temperature.

In order to achieve this technical object, novel materials having hole-transporting properties are continuously being sought.

The prior art discloses the use of triarylamine compounds in electronic devices. These may be monotriarylamines, as described, for example, in JP 1995/053955, WO 2006/123667 and JP 2010/222268, or bis- or poly-amines, as described, for example, in U.S. Pat. No. 7,504,163 or US 2005/0184657. Known examples are, inter alia, tris-p-biphenylamine, N,N'-di-1-naphthyl-N,N'-diphenyl-1,1'-biphenyl-4,4'-diamine (NPB) and 4,4',4"-tris-(3-methyl-phenyl-phenylamino)triphenylamine (MTDATA).

Likewise known is the use of compounds which contain a carbazole unit. Such compounds are employed, in particular, as host materials in emitting layers. Inter alia, the compound CBP (N,N-biscarbazolylbiphenyl) or compounds in accordance with WO 2005/039246, US 2005/0069729, JP 2004/288381, EP 1205527 or WO 2008/086851 is known.

The prior art furthermore discloses the use of hole-transporting compounds which contain both carbazole groups and triarylamino groups, and in which the groups are connected via linker units, such as phenylene (JP 2007-110093). Three, i.e. a plurality of, carbazole groups per molecule are always present in the working examples therein. The compounds are suitable as functional materials for use in OLEDs.

However, there continues to be a need for improvement with respect to the compounds known from the prior art, in particular for use of the compounds in hole-transport and electron-blocking layers, and more particularly in the aspects of efficiency and lifetime of devices comprising the compounds.

Surprisingly, it has now been found that the use of a linker unit consisting of three or more phenylene units between a single triarylamino group and a single carbazole group gives compounds having excellent properties. On use in electronic devices, excellent lifetimes and power efficiencies of the devices are achieved with such compounds.

The present application thus relates to a compound of a formula (I)

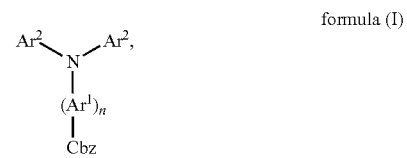

formula (I)

where:
Cbz is a carbazole group, which may be substituted by one or more radicals $R^1$, and which is bonded via the carbazole nitrogen atom;
$Ar^1$ is on each occurrence, identically or differently, an aryl or heteroaryl group having 6 to 14 aromatic ring atoms, which may be substituted by one or more radicals $R^2$, where individual groups $Ar^1$ may be connected to one another via radicals $R^2$;
$Ar^2$ is on each occurrence, identically or differently, an aromatic or heteroaromatic ring system having 6 to 30 aromatic ring atoms, which may be substituted by one or more radicals $R^2$;
$R^1$, $R^2$ is on each occurrence, identically or differently, H, D, F, Cl, Br, I, C(=O)$R^3$, CN, Si($R^3$)$_3$, P(=O)($R^3$)$_2$, S(=O)$R^3$, S(=O)$_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=S, C=N$R^3$, —C(=O)O—, —C(=O)N$R^3$—, N$R^3$, P(=O)($R^3$), —O—, —S—, SO or SO$_2$ and where one or more H atoms in the above-mentioned groups may be replaced by D, F, Cl, Br, I or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^1$ or $R^2$ may be linked to one another and may form a ring;
$R^3$ is on each occurrence, identically or differently, H, D, F, Cl, Br, I, C(=O)$R^4$, CN, Si($R^4$)$_3$, N($R^4$)$_2$, P(=O)($R^4$)$_2$, S(=O)$R^4$, S(=O)$_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups may be replaced by —$R^4$C=C$R^4$—, —C≡C—, Si($R^4$)$_2$, C=O, C=N$R^4$, —C(=O)O—, —C(=O)N$R^4$—, N$R^4$, P(=O)($R^4$), —O—, —S—, SO or SO$_2$ and where one or more H atoms in the above-mentioned groups may be replaced by D, F, Cl, Br, I or CN, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$, where two or more radicals $R^3$ may be linked to one another and may form a ring;

$R^4$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^4$ here may be linked to one another and may form a ring;

n is 3, 4, 5 or 6;

where the compound of the formula (I) contains no further carbazole group besides the group Cbz.

A carbazole group in the sense of the present application is also taken to mean carbazole groups in which one or more carbon atoms of the aromatic six-membered rings have been replaced by nitrogen. Furthermore, it is also taken to mean carbazole groups in which the five-membered carbazole ring has been expanded to form a six-membered ring, so that, for example, a methylene, silylene, oxygen or sulfur bridge is arranged opposite the nitrogen atom. In the former case, this gives rise, for example, to a unit which is also called dihydroacridine. Furthermore, a carbazole groups is also taken to mean carbazole groups containing condensed-on groups, such as, for example, indenocarbazoles or indolocarbazoles.

The carbazole nitrogen atom in the sense of the present application is taken to mean the nitrogen atom of the five-membered ring or of the extended five-membered ring of the carbazole.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spiro-truxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzo-pyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cyclo-heptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following scheme:

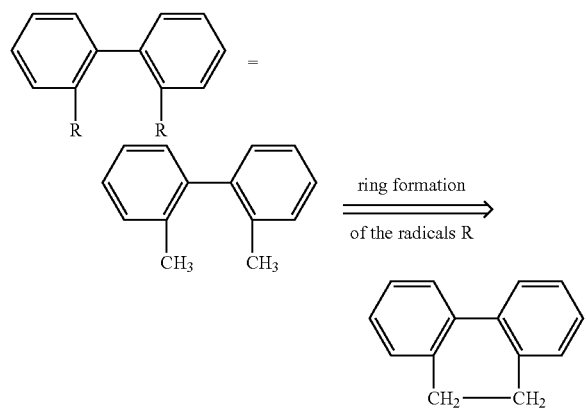

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

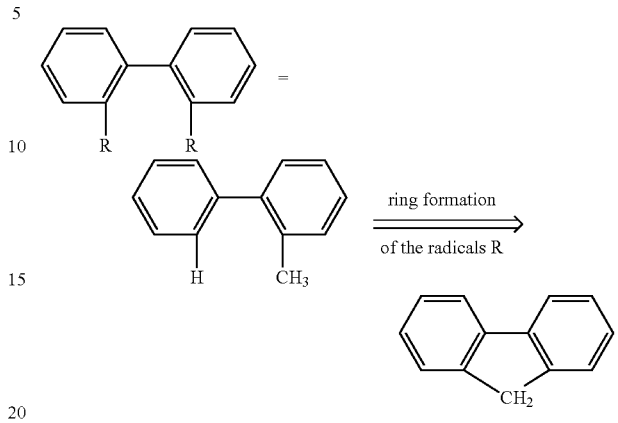

n is preferably equal to 3, 4 or 5, particularly preferably equal to 3 or 4, very particularly preferably equal to 3.

Furthermore, the compound of the formula (I) preferably contains no further arylamino group besides the arylamino group shown. An arylamino group in the sense of this application is taken to mean a group in which at least one aryl group or heteroaryl group is bonded to a trivalent nitrogen atom. The way in which the group is built up further or what further groups it contains is unimportant for the definition. The compound of the formula (I) particularly preferably contains no further amino group besides the arylamino group shown.

Furthermore, the compound of the formula (I) preferably contains no condensed aryl or heteroaryl group having more than 14 aromatic ring atoms. It particularly preferably contains no condensed aryl or heteroaryl group having more than 10 aromatic ring atoms.

Furthermore, $R^1$ is preferably on each occurrence, identically or differently, H, D, F, CN, Si($R^3$)$_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more CH$_2$ groups in the above-mentioned groups may be replaced by —C≡C—, —R$^3$C=CR$^3$—, Si($R^3$)$_2$, C=O, C=NR$^3$, —NR$^3$—, —O—, —S—, —C(=O)O— or —C(=O)NR$^3$—, or an aromatic or heteroaromatic ring system having 5 to 20 aromatic ring atoms, which may in each case be substituted by one or more radicals $R^3$, where two or more radicals $R^1$ may be linked to one another and may form a ring.

Furthermore, $R^2$ is preferably on each occurrence, identically or differently, H, D, F, CN, Si($R^3$)$_3$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more CH$_2$ groups in the above-mentioned groups may be replaced by —C≡C—, —R$^3$C=CR$^3$—, Si($R^3$)$_2$, C=O, C=NR$^3$, —NR$^3$—, —O—, —S—, —C(=O)O— or —C(=O)NR$^3$—, or an aromatic or heteroaromatic ring system having 5 to 20 aromatic ring atoms, which may in each case be substituted by one or more radicals $R^3$, where two or more radicals $R^2$ may be linked to one another and may form a ring.

Furthermore, R³ is preferably on each occurrence, identically or differently, H, D, F, CN, Si(R⁴)₃, a straight-chain alkyl or alkoxy group having 1 to 20 C atoms or a branched or cyclic alkyl or alkoxy group having 3 to 20 C atoms, where the above-mentioned groups may each be substituted by one or more radicals R⁴ and where one or more CH₂ groups in the above-mentioned groups may be replaced by —C≡C—, —R⁴C═CR⁴—, Si(R⁴)₂, C═O, C═NR⁴, —NR⁴—, —O—, —S—, —C(═O)O— or —C(═O)NR⁴—, or an aromatic or heteroaromatic ring system having 5 to 20 aromatic ring atoms, which may in each case be substituted by one or more radicals R⁴, where two or more radicals R³ may be linked to one another and may form a ring.

Cbz is preferably selected from groups of the formula (Cbz)

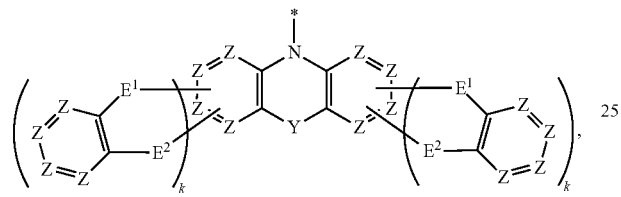

formula (Cbz)

where:

Z is on each occurrence, identically or differently, CR¹ or N, where Z is equal to C if a group E¹ or E² is bonded;

E¹, E² is selected on each occurrence, identically or differently, from a single bond, C(R¹)₂, Si(R¹)₂, C═O, O, S, S═O, SO₂ and NR¹, where E¹ and E² cannot both be a single bond;

Y is a single bond, C(R¹)₂, Si(R¹)₂, O, or S;

k is on each occurrence, identically or differently, 0 or 1;

where the group of the formula (Cbz) is bonded via the bond labelled with *.

The sum of the indices k in the group of the formula (Cbz) is preferably equal to 0 or 1. It is particularly preferably equal to 0, i.e. all indices k are equal to 0.

Furthermore, Y in the group of the formula (Cbz) is preferably a single bond.

It is preferred for not more than three groups Z in the group of the formula (Cbz) in an aromatic ring to be equal to N. It is furthermore preferred for not more than two adjacent groups Z in an aromatic ring to be equal to N. It is furthermore preferred for not more than one group Z per aromatic ring to be equal to N.

It is generally preferred for Z in the group of the formula (Cbz) to be equal to CR¹, where, in the case where a group E¹ or E² is bonded to Z, the group Z is equal to C.

The groups E¹ and E² in the group of the formula (Cbz) are preferably bonded to adjacent groups Z on the six-membered ring.

The groups E¹ and E² in the group of the formula (Cbz) are particularly preferably bonded at the positions which are located in the para-position to the groups Y and N on the aromatic six-membered rings. These are labelled by the symbol # in the following scheme:

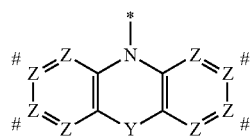

For the groups E¹ and E² in the group of the formula (Cbz), it is preferred for one of E¹ and E² within a unit in brackets with index k to be a single bond and for the other to be selected from C(R¹)₂, Si(R¹)₂, C═O, O, S, S═O, SO₂ and NR¹, preferably from C(R¹)₂, O and S, and particularly preferably C(R¹)₂.

It is furthermore preferred, preferably in combination with the preferences indicated above, for Cbz to be selected from groups of the formula (Cbz-1) to (Cbz-10)

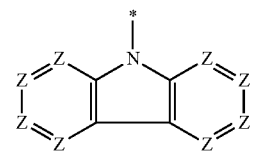

formula (Cbz-1)

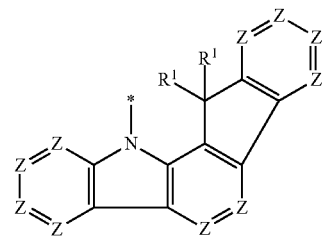

formula (Cbz-2)

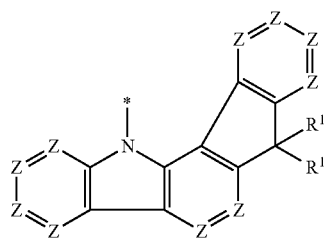

formula (Cbz-3)

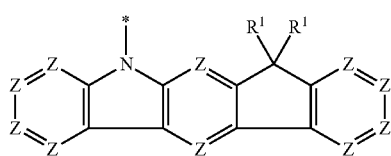

formula (Cbz-4)

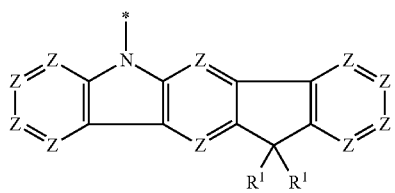

formula (Cbz-5)

-continued

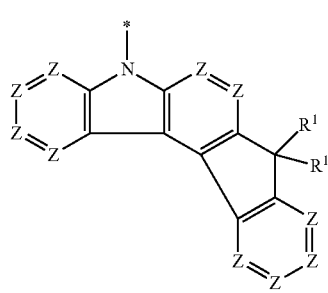

formula (Cbz-6)

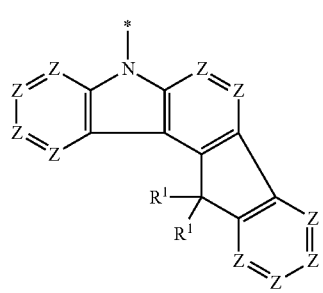

formula (Cbz-7)

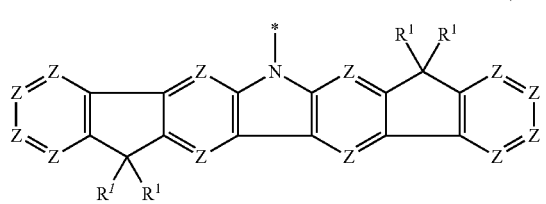

formula (Cbz-8)

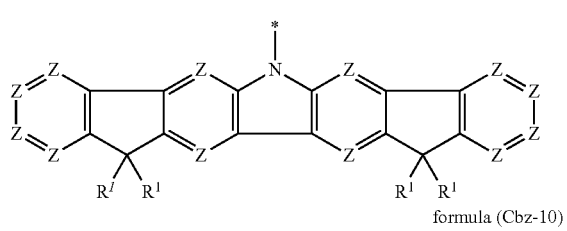

formula (Cbz-9)

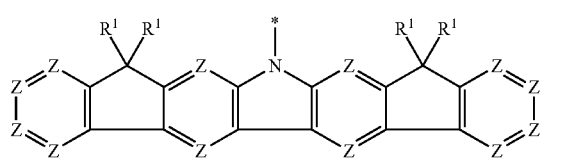

formula (Cbz-10)

where the symbols occurring are defined as above and the group Cbz is bonded via the bond labelled with *.

Furthermore, the above-mentioned preferred embodiments of groups preferably apply to the groups (Cbz-1) to (Cbz-10).

For groups (Cbz-1) to (Cbz-10), Z is especially preferably equal to $CR^1$.

Furthermore, for groups (Cbz-1) to (Cbz-10), $R^1$, $R^2$ and $R^3$ are preferably defined as indicated as preferred above.

Of the formulae indicated above, the formulae (Cbz-1) and (Cbz-4) are particularly preferred.

$Ar^1$ is furthermore preferably on each occurrence, identically or differently, an aryl or heteroaryl group having 6 to 10 aromatic ring atoms, which may be substituted by one or more radicals $R^2$, and where individual groups $Ar^1$ may also be connected to one another via radicals $R^2$. $Ar^1$ is particularly preferably on each occurrence, identically or differently, an aryl or heteroaryl group having 6 aromatic ring atoms, which may be substituted by one or more radicals $R^2$, and where individual groups $Ar^1$ may also be connected to one another via radicals $R^2$. $Ar^1$ is very particularly preferably selected from ortho-phenylene, meta-phenylene and para-phenylene, each of which may be substituted by one or more radicals $R^2$, and where individual groups $Ar^1$ may also be connected to one another via radicals $R^2$.

For embodiments in which groups $Ar^1$ are connected to one another via radicals $R^2$, it is particularly preferred for fluorene groups, dibenzofuran groups or dibenzothiophene groups, preferably fluorene groups, to be formed from two phenyl groups substituted by radicals $R^2$.

It is furthermore preferred for at least one group $Ar^1$ to be selected from ortho-phenylene and meta-phenylene, preferably from meta-phenylene, where the groups may be substituted by one or more radicals $R^2$. Particularly preferably, at least two groups $Ar^1$ are selected from ortho-phenylene or meta-phenylene, preferably from meta-phenylene, where the groups may be substituted by one or more radicals $R^2$.

It is furthermore preferred for n to be equal to 3, and the middle of the three groups $Ar^1$ to be equal to meta-phenylene or ortho-phenylene, which may be substituted by one or more radicals $R^2$.

It is furthermore preferred for n to be equal to 4, and for one or both of the two middle of the four groups $Ar^1$ to be equal to meta-phenylene or ortho-phenylene, where the meta-phenylene or the ortho-phenylene may be substituted by one or more radicals $R^2$.

$Ar^2$ is furthermore preferably selected on each occurrence, identically or differently, from an aromatic or heteroaromatic ring system having 6 to 24 aromatic ring atoms, which may be substituted by one or more radicals $R^2$. Of these, very particular preference is given to phenyl, biphenyl, naphthyl, terphenyl, fluorenyl, spirobifluorene, indenofluorenyl, dibenzofuran, and dibenzothiophene, each of which may be substituted by one or more radicals $R^2$.

Preferred compounds of the formula (I) conform to the following formula (I-A)

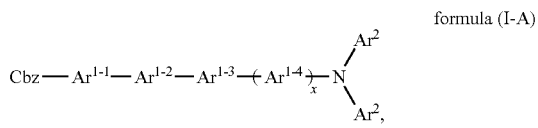

formula (I-A)

where:
Cbz conforms to formula (Cbz-1) or (Cbz-4), as defined above;
$Ar^{1-1}$ to $Ar^{1-4}$ are defined like $Ar^1$ above;
$Ar^2$ is defined like $Ar^2$ above;
x is 0 or 1.

In the case where x=0, the group $Ar^{1-4}$ is not present (n. p.) and $Ar^{1-3}$ and N are connected directly to one another.

The above-mentioned preferred embodiments of groups are likewise preferred for formula (I-A).

$Ar^1$ is preferably on each occurrence, identically or differently, an aryl or heteroaryl group having 6 to 10 aromatic ring atoms, which may be substituted by one or more radicals $R^2$, and where individual groups $Ar^1$ may also be connected to one another via radicals $R^2$. $Ar^1$ is particularly preferably on each occurrence, identically or differently, an aryl or heteroaryl group having 6 aromatic ring atoms, which may be substituted by one or more radicals $R^2$, and where individual groups $Ar^1$ may also be connected to one another via radicals $R^2$. $Ar^1$ is very particularly preferably selected from ortho-phenylene, meta-phenylene and para-phenylene, each of which may be substituted by one or more radicals $R^2$, and where individual groups $Ar^1$ may also be connected to one another via radicals $R^2$.

Particularly preferred embodiments of compounds of the formula (I-A) conform to the following formulae:

| Formula (I-A- | Cbz | $Ar^{1-1}$ | $Ar^{1-2}$ | $Ar^{1-3}$ | $Ar^{1-4}$ |
|---|---|---|---|---|---|
| 1) | (Cbz-1) | p- | p- | m- | n.p. |
| 2) | " | p- | p- | o- | n.p. |
| 3) | " | p- | m- | p- | n.p. |
| 4) | " | p- | m- | m- | n.p. |
| 5) | " | p- | m- | o- | n.p. |
| 6) | " | p- | o- | p- | n.p. |
| 7) | " | p- | o- | m- | n.p. |
| 8) | " | p- | o- | o- | n.p. |
| 9) | " | m- | p- | p- | n.p. |
| 10) | " | m- | p- | m- | n.p. |
| 11) | " | m- | p- | o- | n.p. |
| 12) | " | m- | m- | p- | n.p. |
| 13) | " | m- | m- | m- | n.p. |
| 14) | " | m- | m- | o- | n.p. |
| 15) | " | m- | o- | p- | n.p. |
| 16) | " | m- | o- | m- | n.p. |
| 17) | " | m- | o- | o- | n.p. |
| 18) | " | o- | p- | p- | n.p. |
| 19) | " | o- | p- | m- | n.p. |
| 20) | " | o- | p- | o- | n.p. |
| 21) | " | o- | m- | p- | n.p. |
| 22) | " | o- | m- | m- | n.p. |
| 23) | " | o- | m- | o- | n.p. |
| 24) | " | o- | o- | p- | n.p. |
| 25) | " | o- | o- | m- | n.p. |
| 26) | " | o- | o- | o- | n.p. |
| 27) | (Cbz-4) | p- | p- | m- | n.p. |
| 28) | " | p- | p- | o- | n.p. |
| 29) | " | p- | m- | p- | n.p. |
| 30) | " | p- | m- | m- | n.p. |
| 31) | " | p- | m- | o- | n.p. |
| 32) | " | p- | o- | p- | n.p. |
| 33) | " | p- | o- | m- | n.p. |
| 34) | " | p- | o- | o- | n.p. |
| 35) | " | m- | p- | p- | n.p. |
| 36) | " | m- | p- | m- | n.p. |
| 37) | " | m- | p- | o- | n.p. |
| 38) | " | m- | m- | p- | n.p. |
| 39) | " | m- | m- | m- | n.p. |
| 40) | " | m- | m- | o- | n.p. |
| 41) | " | m- | o- | p- | n.p. |
| 42) | " | m- | o- | m- | n.p. |
| 43) | " | m- | o- | o- | n.p. |
| 44) | " | o- | p- | p- | n.p. |
| 45) | " | o- | p- | m- | n.p. |
| 46) | " | o- | p- | o- | n.p. |
| 47) | " | o- | m- | p- | n.p. |
| 48) | " | o- | m- | m- | n.p. |
| 49) | " | o- | m- | o- | n.p. |
| 50) | " | o- | o- | p- | n.p. |
| 51) | " | o- | o- | m- | n.p. |
| 52) | " | o- | o- | o- | n.p. |
| 53) | (Cbz-1) | p- | p- | m- | p- |
| 54) | " | p- | p- | o- | p- |
| 55) | " | p- | m- | p- | p- |
| 56) | " | p- | m- | m- | p- |
| 57) | " | p- | m- | o- | p- |
| 58) | " | p- | o- | p- | p- |
| 59) | " | p- | o- | m- | p- |
| 60) | " | p- | o- | o- | p- |
| 61) | " | m- | p- | p- | p- |
| 62) | " | m- | p- | m- | p- |
| 63) | " | m- | p- | o- | p- |
| 64) | " | m- | m- | p- | p- |
| 65) | " | m- | m- | m- | p- |
| 66) | " | m- | m- | o- | p- |
| 67) | " | m- | o- | p- | p- |
| 68) | " | m- | o- | m- | p- |
| 69) | " | m- | o- | o- | p- |
| 70) | " | o- | p- | p- | p- |
| 71) | " | o- | p- | m- | p- |
| 72) | " | o- | p- | o- | p- |
| 73) | " | o- | m- | p- | p- |
| 74) | " | o- | m- | m- | p- |
| 75) | " | o- | m- | o- | p- |
| 76) | " | o- | o- | p- | p- |
| 77) | " | o- | o- | m- | p- |
| 78) | " | o- | o- | o- | p- |
| 79) | " | p- | p- | p- | m- |
| 80) | " | p- | p- | m- | m- |
| 81) | " | p- | p- | o- | m- |
| 82) | " | p- | m- | p- | m- |
| 83) | " | p- | m- | m- | m- |
| 84) | " | p- | m- | o- | m- |
| 85) | " | p- | o- | p- | m- |
| 86) | " | p- | o- | m- | m- |
| 87) | " | p- | o- | o- | m- |
| 88) | " | m- | p- | p- | m- |
| 89) | " | m- | p- | m- | m- |
| 90) | " | m- | p- | o- | m- |
| 91) | " | m- | m- | p- | m- |
| 92) | " | m- | m- | m- | m- |
| 93) | " | m- | m- | o- | m- |
| 94) | " | m- | o- | p- | m- |
| 95) | " | m- | o- | m- | m- |
| 96) | " | m- | o- | o- | m- |
| 97) | " | o- | p- | p- | m- |
| 98) | " | o- | p- | m- | m- |
| 99) | " | o- | p- | o- | m- |
| 100) | " | o- | m- | p- | m- |
| 101) | " | o- | m- | m- | m- |
| 102) | " | o- | m- | o- | m- |
| 103) | " | o- | o- | p- | m- |
| 104) | " | o- | o- | m- | m- |
| 105) | " | o- | o- | o- | m- |
| 106) | " | p- | p- | p- | o- |
| 107) | " | p- | p- | m- | o- |
| 108) | " | p- | p- | o- | o- |
| 109) | " | p- | m- | p- | o- |
| 110) | " | p- | m- | m- | o- |
| 111) | " | p- | m- | o- | o- |
| 112) | " | p- | o- | p- | o- |
| 113) | " | p- | o- | m- | o- |
| 114) | " | p- | o- | o- | o- |
| 115) | " | m- | p- | p- | o- |
| 116) | " | m- | p- | m- | o- |
| 117) | " | m- | p- | o- | o- |
| 118) | " | m- | m- | p- | o- |
| 119) | " | m- | m- | m- | o- |
| 120) | " | m- | m- | o- | o- |
| 121) | " | m- | o- | p- | o- |
| 122) | " | m- | o- | m- | o- |
| 123) | " | m- | o- | o- | o- |
| 124) | " | o- | p- | p- | o- |
| 125) | " | o- | p- | m- | o- |
| 126) | " | o- | p- | o- | o- |
| 127) | " | o- | m- | p- | o- |
| 128) | " | o- | m- | m- | o- |
| 129) | " | o- | m- | o- | o- |
| 130) | " | o- | o- | p- | o- |
| 131) | " | o- | o- | m- | o- |
| 132) | " | o- | o- | o- | o- |
| 133) | (Cbz-4) | p- | p- | m- | p- |
| 134) | " | p- | p- | o- | p- |
| 135) | " | p- | m- | p- | p- |
| 136) | " | p- | m- | m- | p- |
| 137) | " | p- | m- | o- | p- |
| 138) | " | p- | o- | p- | p- |
| 139) | " | p- | o- | m- | p- |
| 140) | " | p- | o- | o- | p- |
| 141) | " | m- | p- | p- | p- |
| 142) | " | m- | p- | m- | p- |
| 143) | " | m- | p- | o- | p- |
| 144) | " | m- | m- | p- | p- |
| 145) | " | m- | m- | m- | p- |
| 146) | " | m- | m- | o- | p- |
| 147) | " | m- | o- | p- | p- |

| Formula (I-A- | Cbz | $Ar^{1-1}$ | $Ar^{1-2}$ | $Ar^{1-3}$ | $Ar^{1-4}$ |
|---|---|---|---|---|---|
| 148) | " | m- | o- | m- | p- |
| 149) | " | m- | o- | o- | p- |
| 150) | " | o- | p- | p- | p- |
| 151) | " | o- | p- | m- | p- |
| 152) | " | o- | p- | o- | p- |
| 153) | " | o- | m- | p- | p- |
| 154) | " | o- | m- | m- | p- |
| 155) | " | o- | m- | o- | p- |
| 156) | " | o- | o- | p- | p- |
| 157) | " | o- | o- | m- | p- |
| 158) | " | o- | o- | o- | p- |
| 159) | " | p- | p- | p- | m- |
| 160) | " | p- | p- | m- | m- |
| 161) | " | p- | p- | o- | m- |
| 162) | " | p- | m- | p- | m- |
| 163) | " | p- | m- | m- | m- |
| 164) | " | p- | m- | o- | m- |
| 165) | " | p- | o- | p- | m- |
| 166) | " | p- | o- | m- | m- |
| 167) | " | p- | o- | o- | m- |
| 168) | " | m- | p- | p- | m- |
| 169) | " | m- | p- | m- | m- |
| 170) | " | m- | p- | o- | m- |
| 171) | " | m- | m- | p- | m- |
| 172) | " | m- | m- | m- | m- |
| 173) | " | m- | m- | o- | m- |
| 174) | " | m- | o- | p- | m- |
| 175) | " | m- | o- | m- | m- |
| 176) | " | m- | o- | o- | m- |
| 177) | " | o- | p- | p- | m- |
| 178) | " | o- | p- | m- | m- |
| 179) | " | o- | p- | o- | m- |
| 180) | " | o- | m- | p- | m- |
| 181) | " | o- | m- | m- | m- |
| 182) | " | o- | m- | o- | m- |
| 183) | " | o- | o- | p- | m- |
| 184) | " | o- | o- | m- | m- |
| 185) | " | o- | o- | o- | m- |
| 186) | " | p- | p- | p- | o- |
| 187) | " | p- | p- | m- | o- |
| 188) | " | p- | p- | o- | o- |
| 189) | " | p- | m- | p- | o- |
| 190) | " | p- | m- | m- | o- |
| 191) | " | p- | m- | o- | o- |
| 192) | " | p- | o- | p- | o- |
| 193) | " | p- | o- | m- | o- |
| 194) | " | p- | o- | o- | o- |
| 195) | " | m- | p- | p- | o- |
| 196) | " | m- | p- | m- | o- |
| 197) | " | m- | p- | o- | o- |
| 198) | " | m- | m- | p- | o- |
| 199) | " | m- | m- | m- | o- |
| 200) | " | m- | m- | o- | o- |
| 201) | " | m- | o- | p- | o- |
| 202) | " | m- | o- | m- | o- |
| 203) | " | m- | o- | o- | o- |
| 204) | " | o- | p- | p- | o- |
| 205) | " | o- | p- | m- | o- |
| 206) | " | o- | p- | o- | o- |
| 207) | " | o- | m- | p- | o- |
| 208) | " | o- | m- | m- | o- |
| 209) | " | o- | m- | o- | o- |
| 210) | " | o- | o- | p- | o- |
| 211) | " | o- | o- | m- | o- |
| 212) | " | o- | o- | o- | o- |

In the table, "p-" in each case stands for para-phenylene, which may be substituted by one or more radicals $R^2$, as defined above. Correspondingly, "m-" stands for meta-phenylene, which may be substituted by one or more radicals $R^2$, as defined above. Correspondingly, "o-" stands for ortho-phenylene, which may be substituted by one or more radicals $R^2$, as defined above.

$Ar^{1-1}$=ortho-phenylene here denotes that the group $Ar^{1-1}$ is connected to the adjacent groups, here Cbz and $Ar^{1-2}$, via bonds in the ortho positions. A corresponding situation applies to meta-phenylene (bonds in the meta-positions) and para-phenylene (bonds in the para-positions).

Examples of compounds of the formula (I) are shown in the following table.

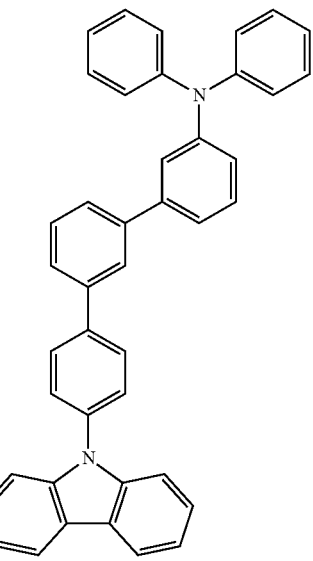

1

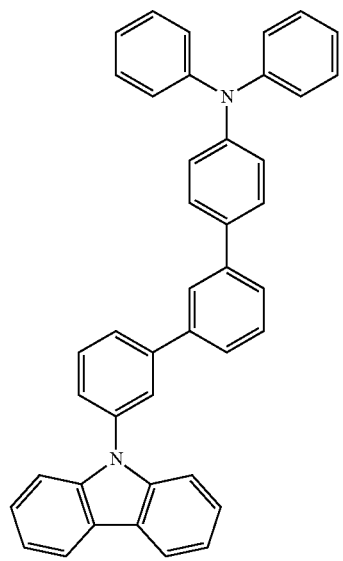 [SMILES: c1ccc(N(c2ccccc2)c2ccc(-c3cccc(-c4cccc(-n5c6ccccc6c6ccccc65)c4)c3)cc2)cc1]
2
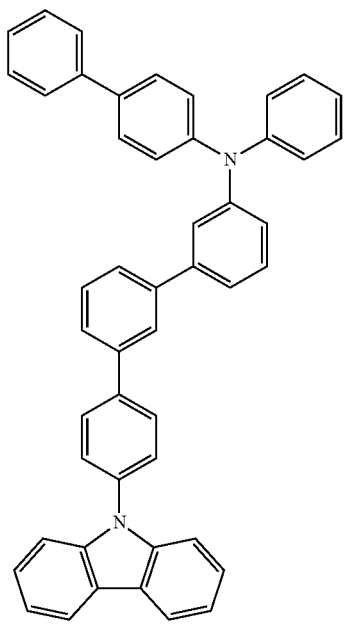 [SMILES: c1ccc(-c2ccc(N(c3ccccc3)c3cccc(-c4cccc(-c5ccc(-n6c7ccccc7c7ccccc76)cc5)c4)c3)cc2)cc1]
3

-continued
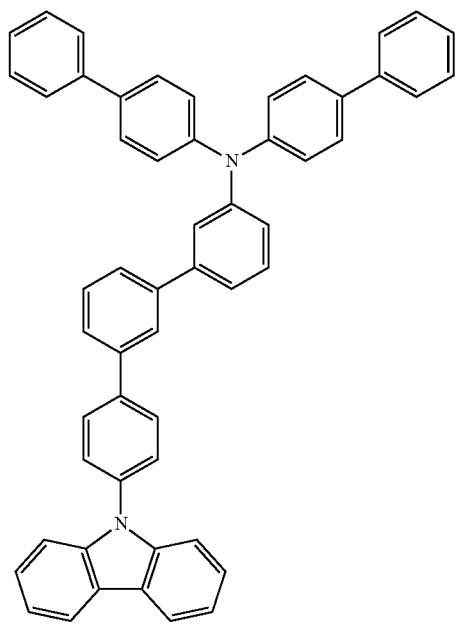 [SMILES: c1ccc(-c2ccc(N(c3ccc(-c4ccccc4)cc3)c3cccc(-c4cccc(-c5ccc(-n6c7ccccc7c7ccccc76)cc5)c4)c3)cc2)cc1]
4
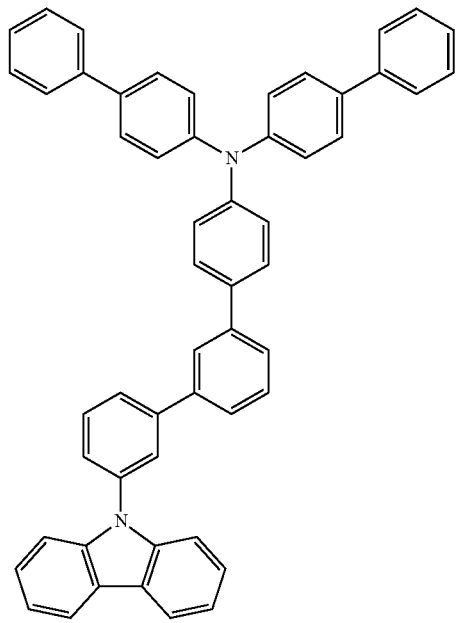 [SMILES: c1ccc(-c2ccc(N(c3ccc(-c4ccccc4)cc3)c3ccc(-c4cccc(-c5cccc(-n6c7ccccc7c7ccccc76)c5)c4)cc3)cc2)cc1]
5

-continued
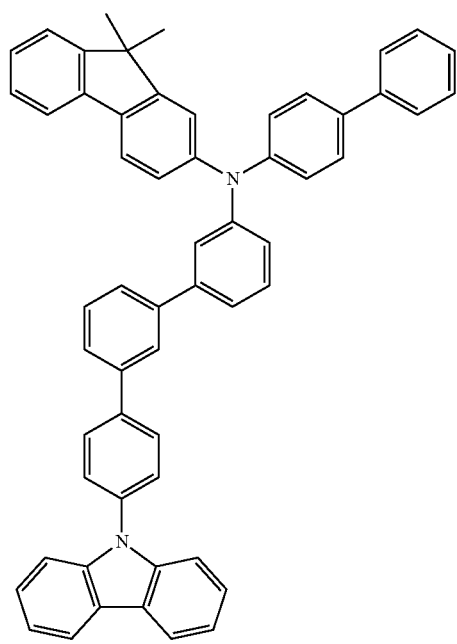 [SMILES: CC1(C)c2ccccc2-c2ccc(N(c3ccc(-c4ccccc4)cc3)c3cccc(-c4cccc(-c5ccc(-n6c7ccccc7c7ccccc76)cc5)c4)c3)cc21]
6
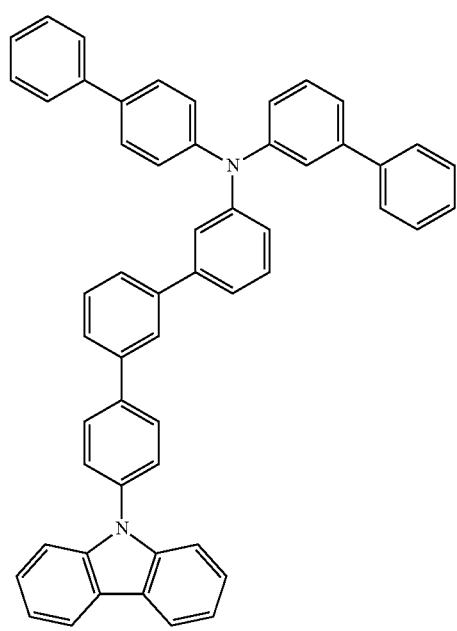 [SMILES: c1ccc(-c2ccc(N(c3cccc(-c4ccccc4)c3)c3cccc(-c4cccc(-c5ccc(-n6c7ccccc7c7ccccc76)cc5)c4)c3)cc2)cc1]
7

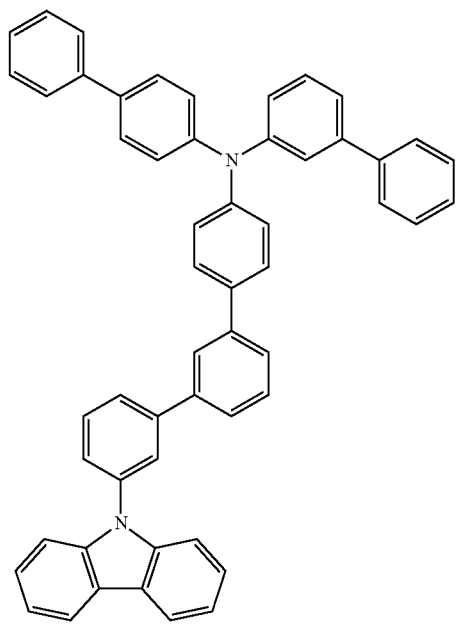 [SMILES: c1ccc(-c2ccc(N(c3ccc(-c4cccc(-c5cccc(-n6c7ccccc7c7ccccc76)c5)c4)cc3)c3cccc(-c4ccccc4)c3)cc2)cc1]
8
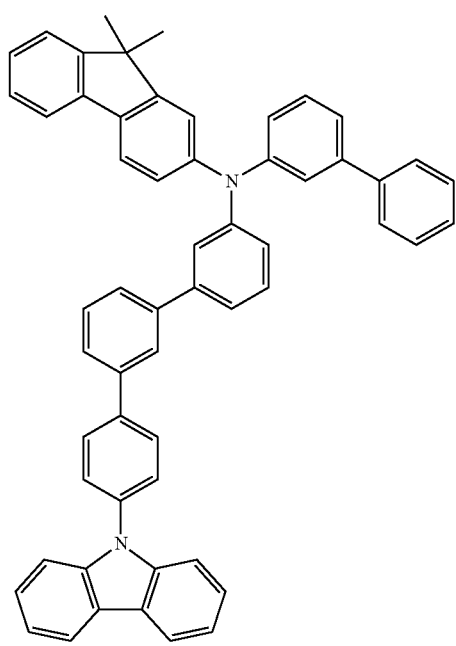 [SMILES: CC1(C)c2ccccc2-c2ccc(N(c3cccc(-c4ccccc4)c3)c3cccc(-c4cccc(-c5ccc(-n6c7ccccc7c7ccccc76)cc5)c4)c3)cc21]
9

-continued
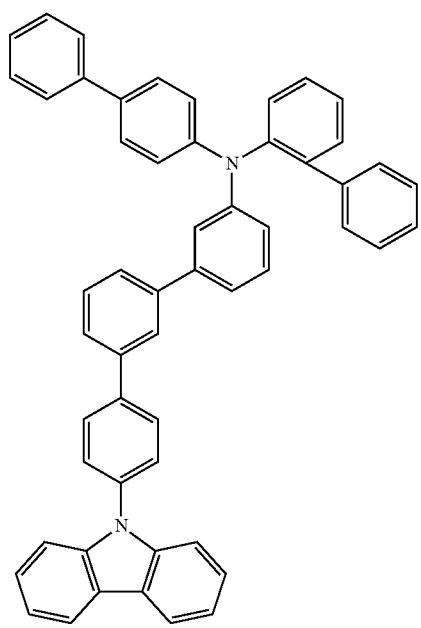 [SMILES: c1ccc(-c2ccc(N(c3cccc(-c4cccc(-c5ccc(-n6c7ccccc7c7ccccc76)cc5)c4)c3)c3ccccc3-c3ccccc3)cc2)cc1]
10
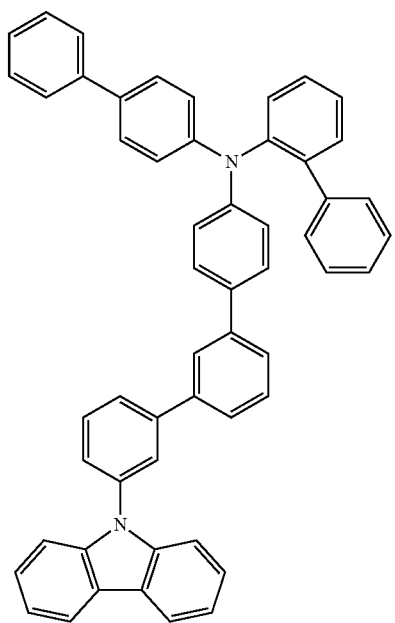 [SMILES: c1ccc(-c2ccc(N(c3ccc(-c4cccc(-c5cccc(-n6c7ccccc7c7ccccc76)c5)c4)cc3)c3ccccc3-c3ccccc3)cc2)cc1]
11

12
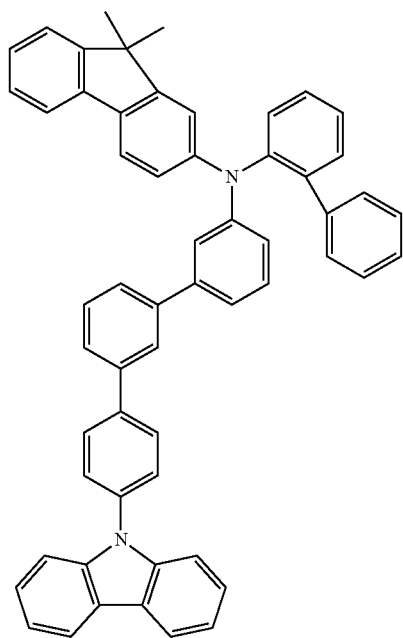 [SMILES: CC1(C)c2ccccc2-c2ccc(N(c3cccc(-c4cccc(-c5ccc(-n6c7ccccc7c7ccccc76)cc5)c4)c3)c3ccccc3-c3ccccc3)cc21]
13
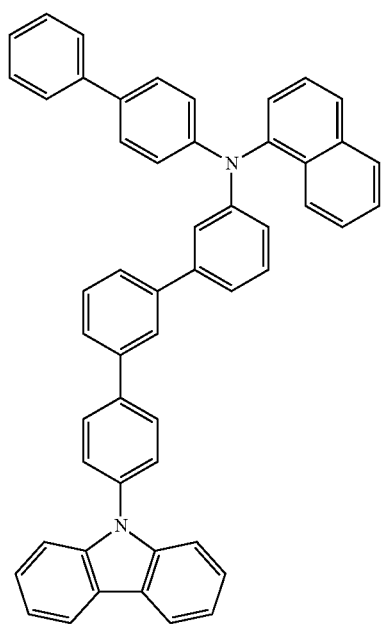 [SMILES: c1ccc(-c2ccc(N(c3cccc(-c4cccc(-c5ccc(-n6c7ccccc7c7ccccc76)cc5)c4)c3)c3cccc4ccccc34)cc2)cc1]

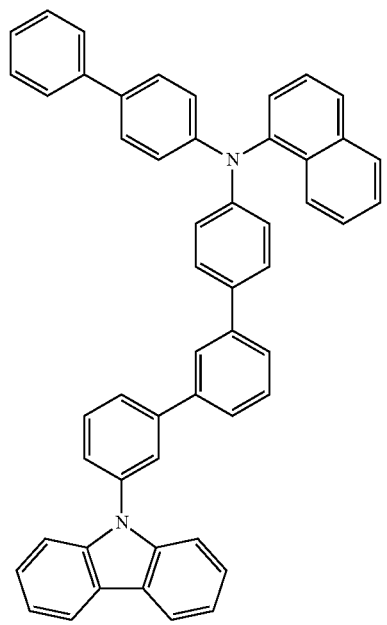 [SMILES: c1ccc(-c2ccc(N(c3ccc(-c4cccc(-c5cccc(-n6c7ccccc7c7ccccc76)c5)c4)cc3)c3cccc4ccccc34)cc2)cc1]
14
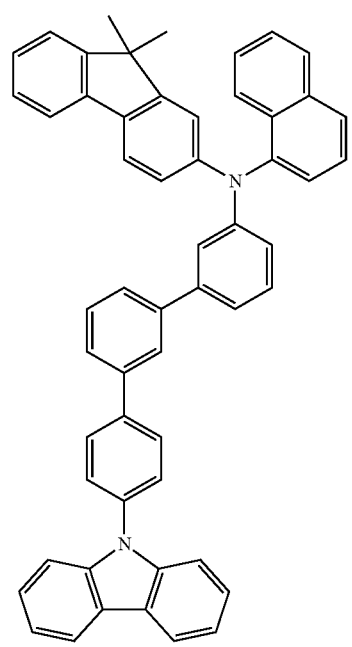 [SMILES: CC1(C)c2ccccc2-c2ccc(N(c3cccc(-c4cccc(-c5ccc(-n6c7ccccc7c7ccccc76)cc5)c4)c3)c3cccc4ccccc34)cc21]
15

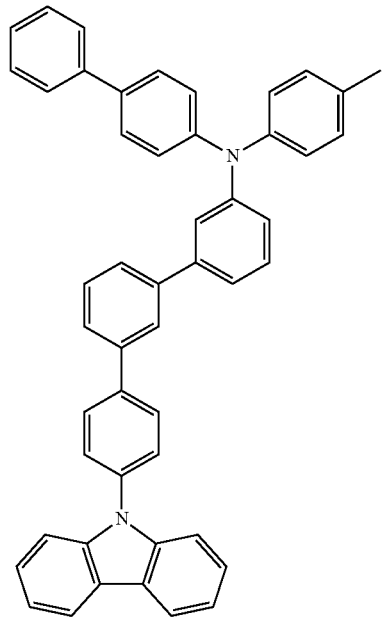 [SMILES: Cc1ccc(N(c2ccc(-c3ccccc3)cc2)c2cccc(-c3cccc(-c4ccc(-n5c6ccccc6c6ccccc65)cc4)c3)c2)cc1]
16
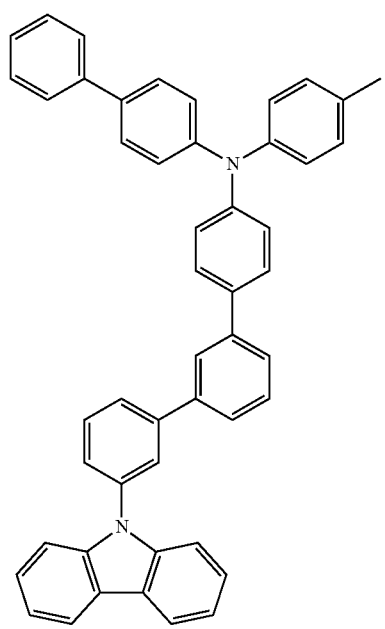 [SMILES: Cc1ccc(N(c2ccc(-c3ccccc3)cc2)c2ccc(-c3cccc(-c4cccc(-n5c6ccccc6c6ccccc65)c4)c3)cc2)cc1]
17

-continued
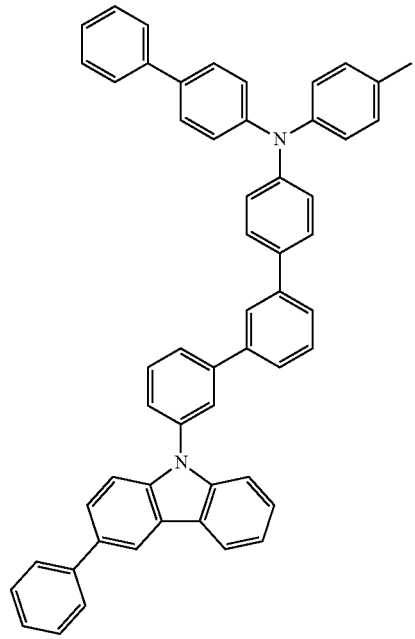 [SMILES: Cc1ccc(N(c2ccc(-c3ccccc3)cc2)c2ccc(-c3cccc(-c4cccc(-n5c6ccccc6c6cc(-c7ccccc7)ccc65)c4)c3)cc2)cc1]
18
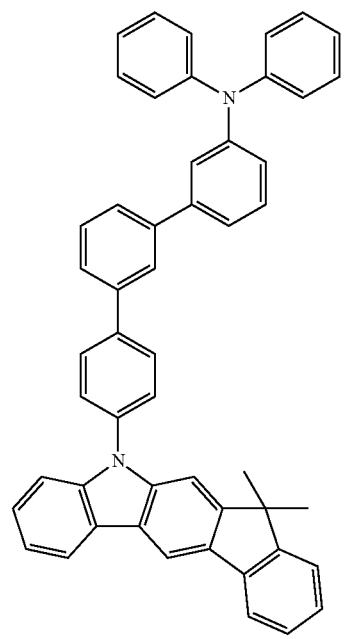 [SMILES: CC1(C)c2ccccc2-c2cc3c4ccccc4n(-c4ccc(-c5cccc(-c6cccc(N(c7ccccc7)c7ccccc7)c6)c5)cc4)c3cc21]
19

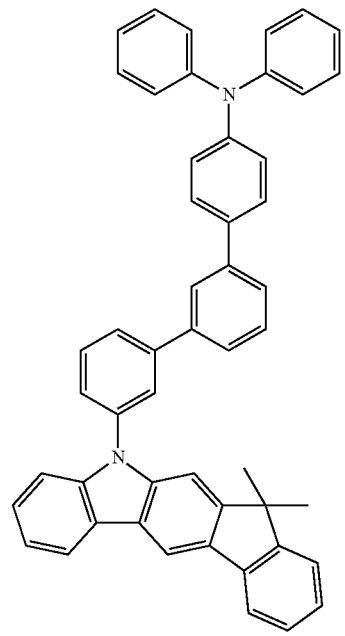 [SMILES: CC1(C)c2ccccc2-c2cc3c4ccccc4n(-c4cccc(-c5cccc(-c6ccc(N(c7ccccc7)c7ccccc7)cc6)c5)c4)c3cc21]
20
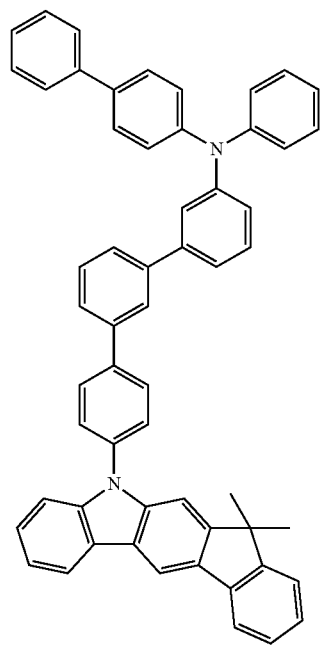 [SMILES: CC1(C)c2ccccc2-c2cc3c4ccccc4n(-c4ccc(-c5cccc(-c6cccc(N(c7ccccc7)c7ccc(-c8ccccc8)cc7)c6)c5)cc4)c3cc21]
21
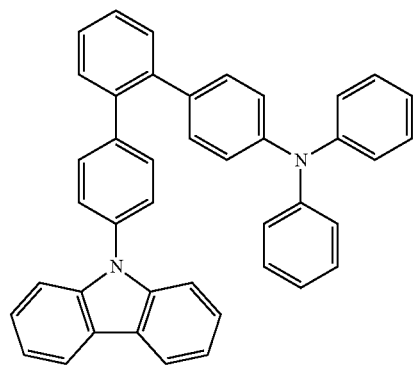 [SMILES: c1ccc(N(c2ccccc2)c2ccc(-c3ccccc3-c3ccc(-n4c5ccccc5c5ccccc54)cc3)cc2)cc1]
22

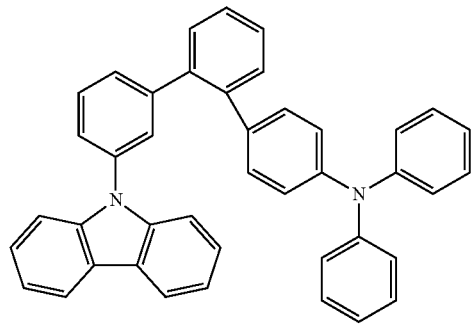 [SMILES: c1ccc(N(c2ccccc2)c2ccc(-c3ccccc3-c3cccc(-n4c5ccccc5c5ccccc54)c3)cc2)cc1]
23
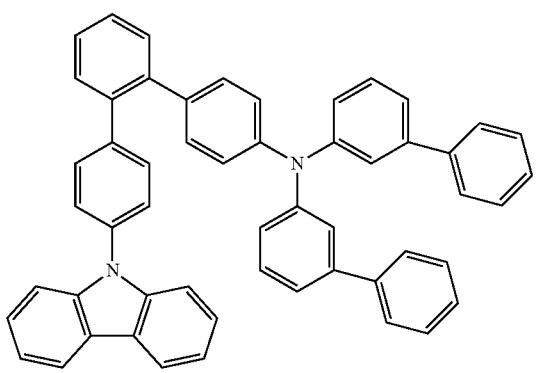 [SMILES: c1ccc(-c2cccc(N(c3ccc(-c4ccccc4-c4ccc(-n5c6ccccc6c6ccccc65)cc4)cc3)c3cccc(-c4ccccc4)c3)c2)cc1]
24
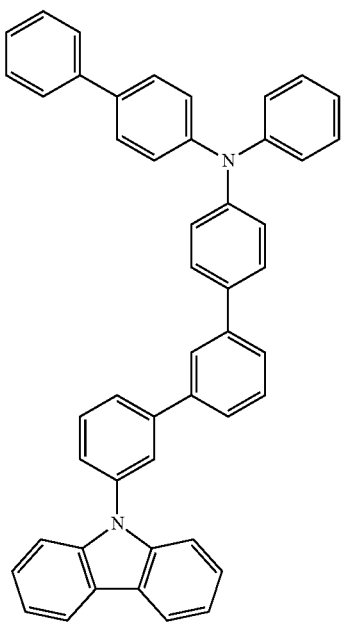 [SMILES: c1ccc(-c2ccc(N(c3ccccc3)c3ccc(-c4cccc(-c5cccc(-n6c7ccccc7c7ccccc76)c5)c4)cc3)cc2)cc1]
25

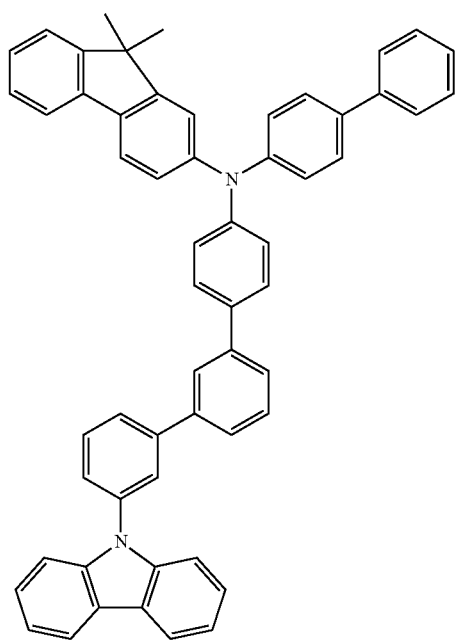 [SMILES: CC1(C)c2ccccc2-c2ccc(N(c3ccc(-c4ccccc4)cc3)c3ccc(-c4cccc(-c5cccc(-n6c7ccccc7c7ccccc76)c5)c4)cc3)cc21]
26
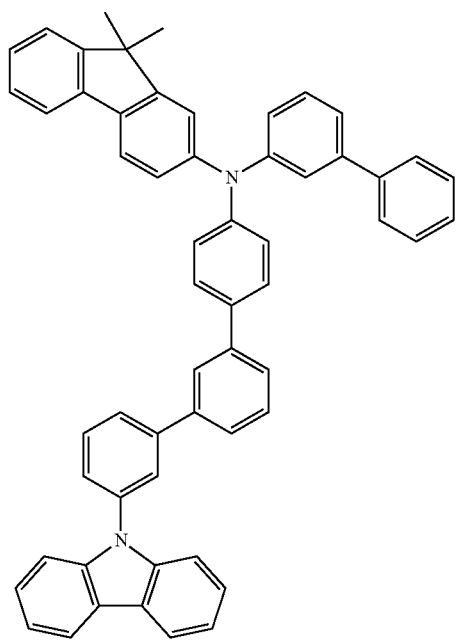 [SMILES: CC1(C)c2ccccc2-c2ccc(N(c3ccc(-c4cccc(-c5cccc(-n6c7ccccc7c7ccccc76)c5)c4)cc3)c3cccc(-c4ccccc4)c3)cc21]
27

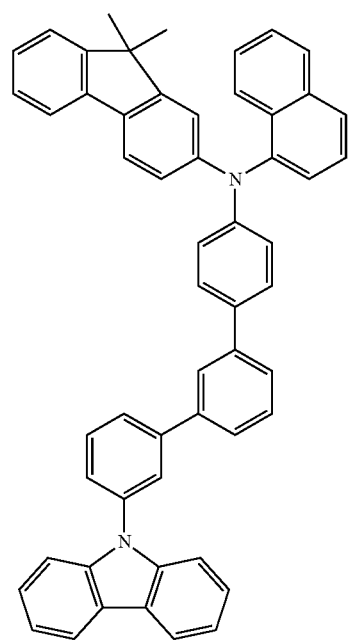 [SMILES: CC1(C)c2ccccc2-c2ccc(N(c3ccc(-c4cccc(-c5cccc(-n6c7ccccc7c7ccccc76)c5)c4)cc3)c3cccc4ccccc34)cc21]
28
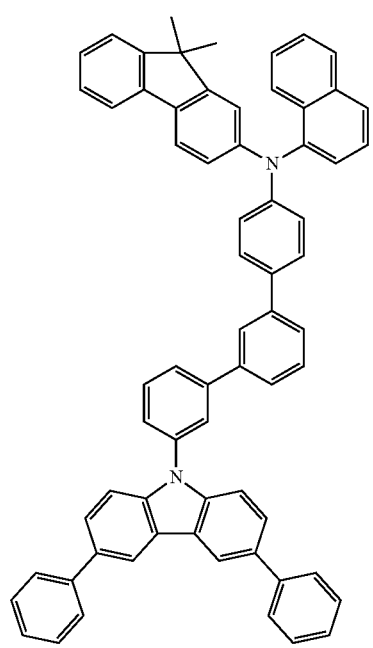 [SMILES: CC1(C)c2ccccc2-c2ccc(N(c3ccc(-c4cccc(-c5cccc(-n6c7ccc(-c8ccccc8)cc7c7cc(-c8ccccc8)ccc76)c5)c4)cc3)c3cccc4ccccc34)cc21]
29

-continued
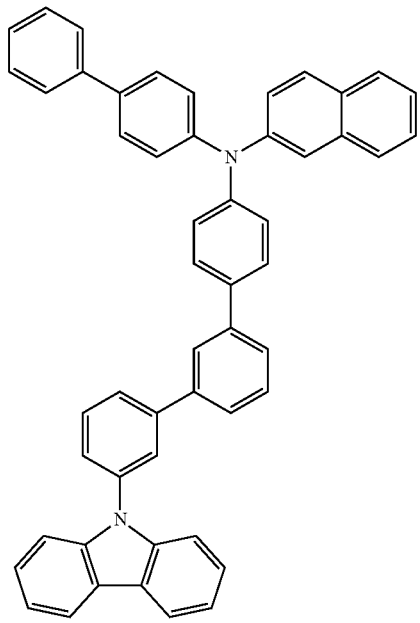 [SMILES: c1ccc(-c2ccc(N(c3ccc(-c4cccc(-c5cccc(-n6c7ccccc7c7ccccc76)c5)c4)cc3)c3ccc4ccccc4c3)cc2)cc1]
30
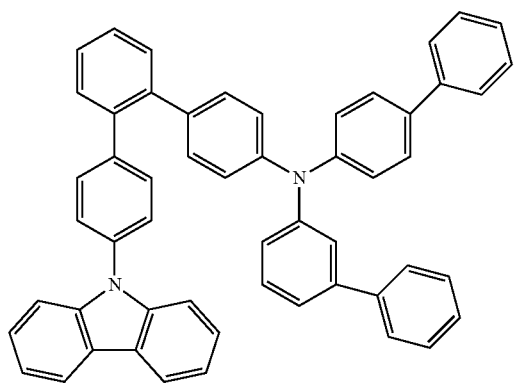 [SMILES: c1ccc(-c2ccc(N(c3ccc(-c4ccccc4-c4ccc(-n5c6ccccc6c6ccccc65)cc4)cc3)c3cccc(-c4ccccc4)c3)cc2)cc1]
31
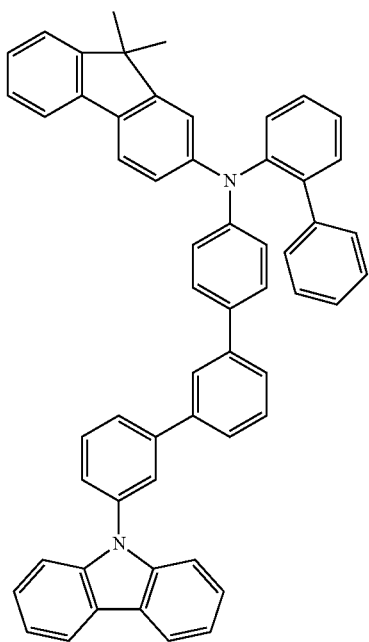 [SMILES: CC1(C)c2ccccc2-c2ccc(N(c3ccc(-c4cccc(-c5cccc(-n6c7ccccc7c7ccccc76)c5)c4)cc3)c3ccccc3-c3ccccc3)cc21]
32

-continued
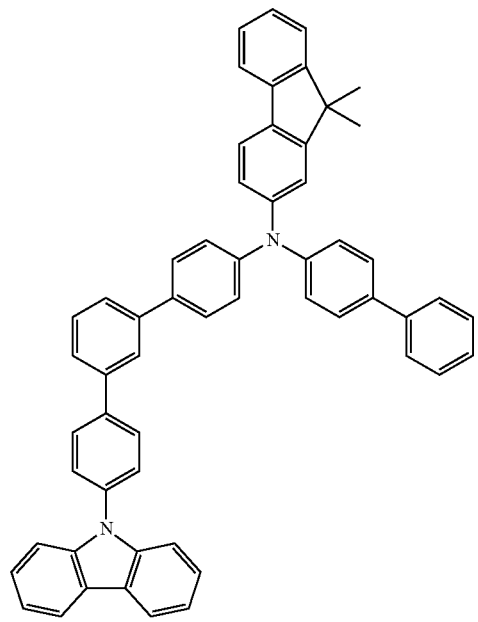 [SMILES: CC1(C)c2ccccc2-c2ccc(N(c3ccc(-c4ccccc4)cc3)c3ccc(-c4cccc(-c5ccc(-n6c7ccccc7c7ccccc76)cc5)c4)cc3)cc21]
33
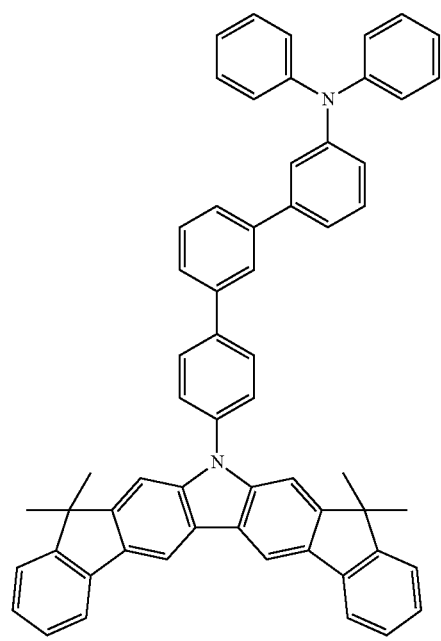 [SMILES: CC1(C)c2ccccc2-c2cc3c4cc5c(cc4n(-c4ccc(-c6cccc(-c7cccc(N(c8ccccc8)c8ccccc8)c7)c6)cc4)c3cc21)C(C)(C)c1ccccc1-5]
34

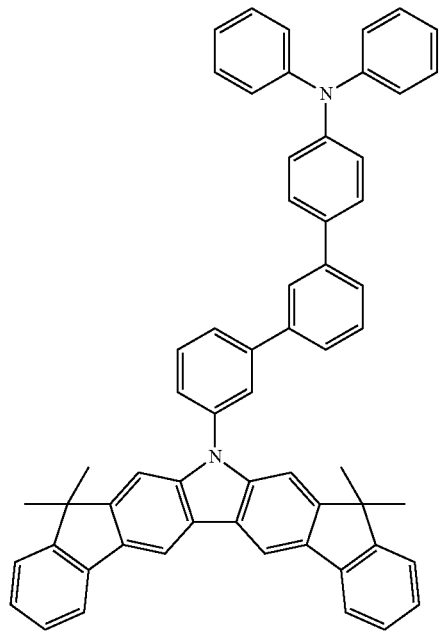 [SMILES: CC1(C)c2ccccc2-c2cc3c4cc5c(cc4n(-c4cccc(-c6cccc(-c7ccc(N(c8ccccc8)c8ccccc8)cc7)c6)c4)c3cc21)C(C)(C)c1ccccc1-5]
35
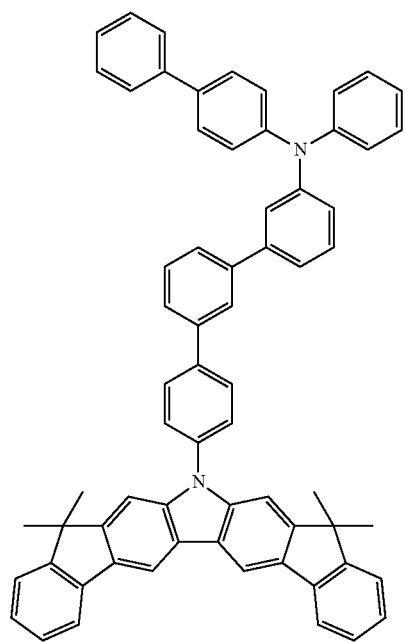 [SMILES: CC1(C)c2ccccc2-c2cc3c4cc5c(cc4n(-c4ccc(-c6cccc(-c7cccc(N(c8ccccc8)c8ccc(-c9ccccc9)cc8)c7)c6)cc4)c3cc21)C(C)(C)c1ccccc1-5]
36

-continued
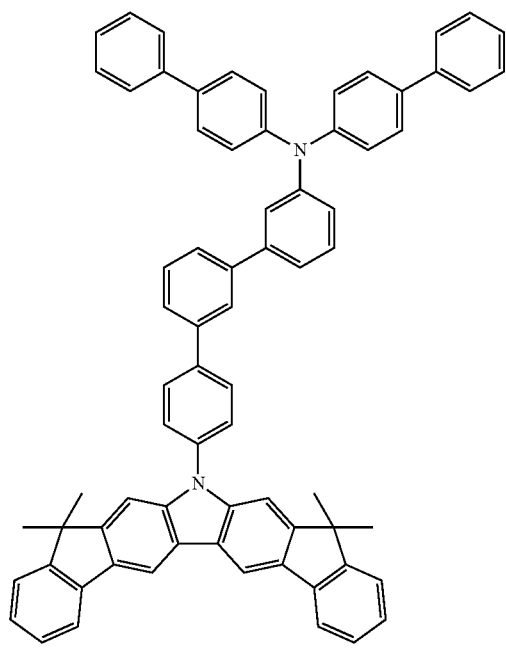 [SMILES: CC1(C)c2ccccc2-c2cc3c4cc5c(cc4n(-c4ccc(-c6cccc(-c7cccc(N(c8ccc(-c9ccccc9)cc8)c8ccc(-c9ccccc9)cc8)c7)c6)cc4)c3cc21)C(C)(C)c1ccccc1-5]
37
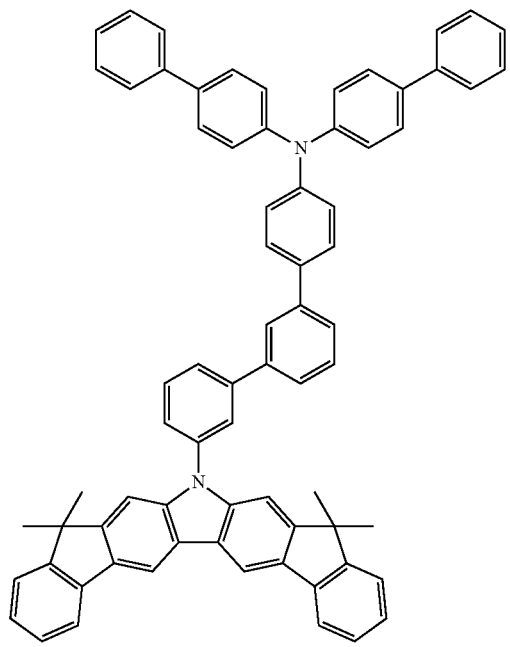 [SMILES: CC1(C)c2ccccc2-c2cc3c4cc5c(cc4n(-c4cccc(-c6cccc(-c7ccc(N(c8ccc(-c9ccccc9)cc8)c8ccc(-c9ccccc9)cc8)cc7)c6)c4)c3cc21)C(C)(C)c1ccccc1-5]
38

-continued
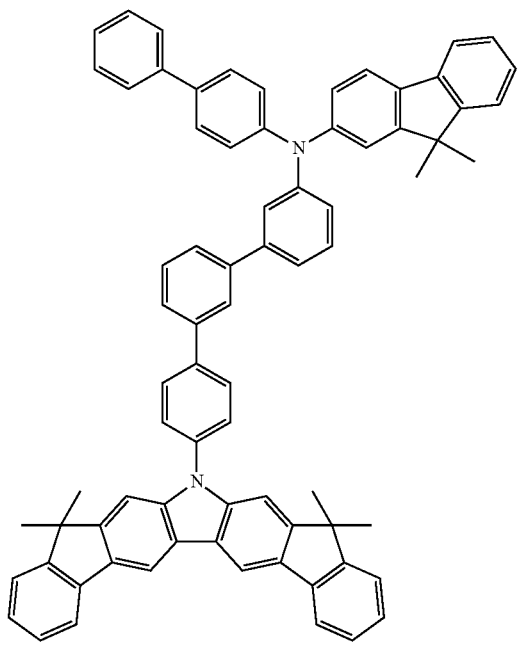 [SMILES: CC1(C)c2ccccc2-c2ccc(N(c3ccc(-c4ccccc4)cc3)c3cccc(-c4cccc(-c5ccc(-n6c7cc8c(cc7c7cc9c(cc76)C(C)(C)c6ccccc6-9)-c6ccccc6C8(C)C)cc5)c4)c3)cc21]
39
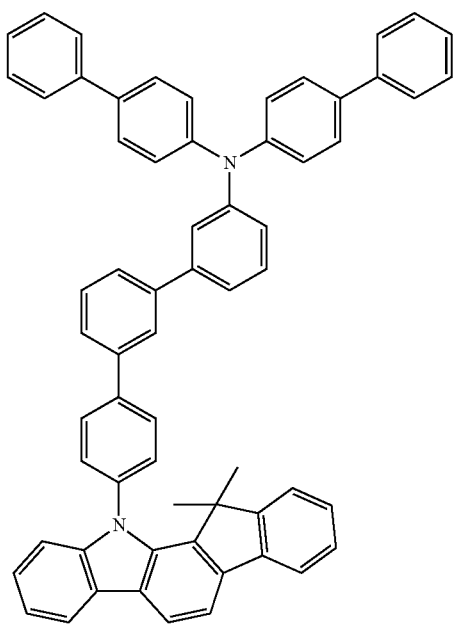 [SMILES: CC1(C)c2ccccc2-c2ccc3c4ccccc4n(-c4ccc(-c5cccc(-c6cccc(N(c7ccc(-c8ccccc8)cc7)c7ccc(-c8ccccc8)cc7)c6)c5)cc4)c3c21]
40

-continued
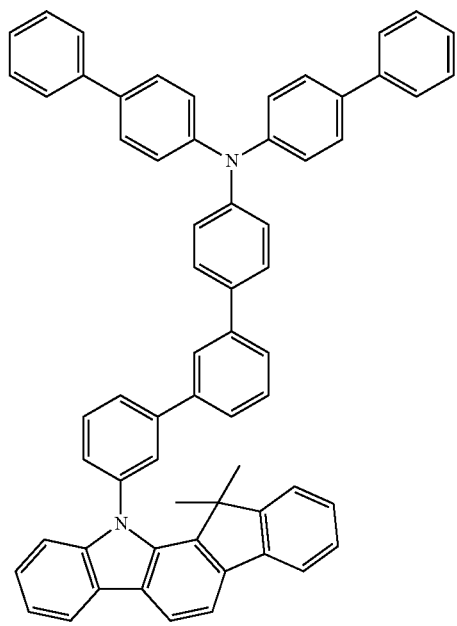 [SMILES: CC1(C)c2ccccc2-c2ccc3c4ccccc4n(-c4cccc(-c5cccc(-c6ccc(N(c7ccc(-c8ccccc8)cc7)c7ccc(-c8ccccc8)cc7)cc6)c5)c4)c3c21]
41
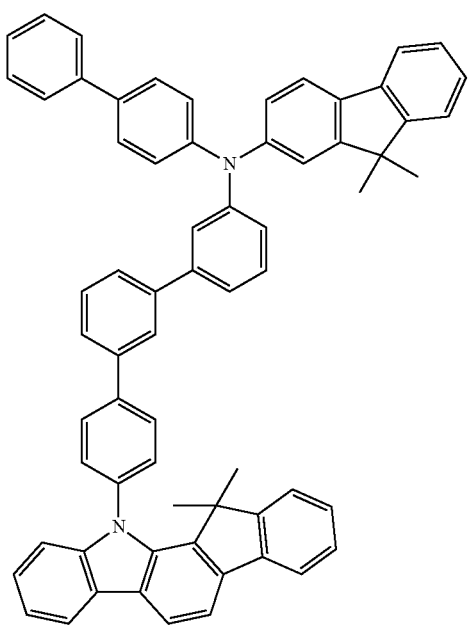 [SMILES: CC1(C)c2ccccc2-c2ccc(N(c3ccc(-c4ccccc4)cc3)c3cccc(-c4cccc(-c5ccc(-n6c7ccccc7c7ccc8c(c76)C(C)(C)c6ccccc6-8)cc5)c4)c3)cc21]
42

-continued
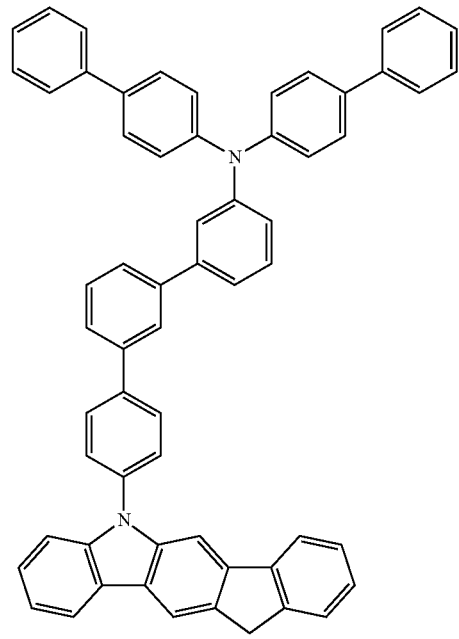 [SMILES: c1ccc(-c2ccc(N(c3ccc(-c4ccccc4)cc3)c3cccc(-c4cccc(-c5ccc(-n6c7ccccc7c7cc8c(cc76)-c6ccccc6C8)cc5)c4)c3)cc2)cc1]
43
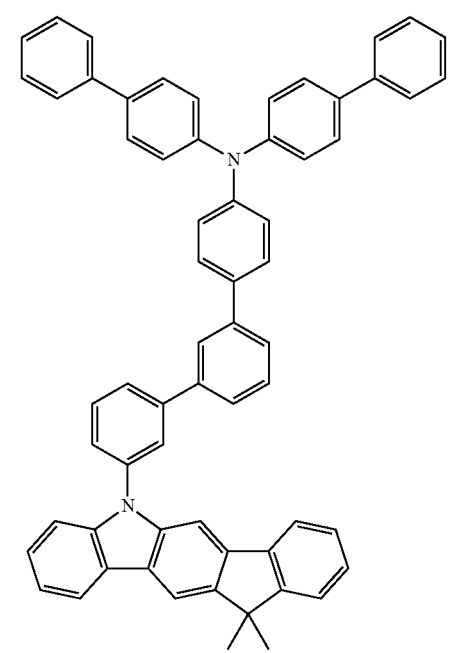 [SMILES: CC1(C)c2ccccc2-c2cc3c(cc21)c1ccccc1n3-c1cccc(-c2cccc(-c3ccc(N(c4ccc(-c5ccccc5)cc4)c4ccc(-c5ccccc5)cc4)cc3)c2)c1]
44

-continued
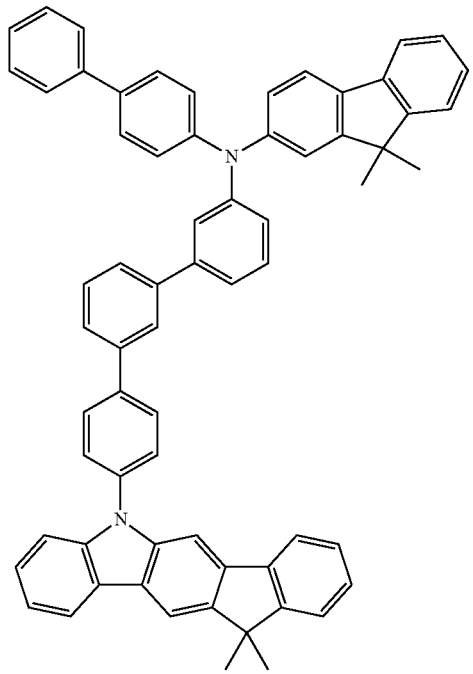 [SMILES: CC1(C)c2ccccc2-c2ccc(N(c3ccc(-c4ccccc4)cc3)c3cccc(-c4cccc(-c5ccc(-n6c7ccccc7c7cc8c(cc76)-c6ccccc6C8(C)C)cc5)c4)c3)cc21]
45
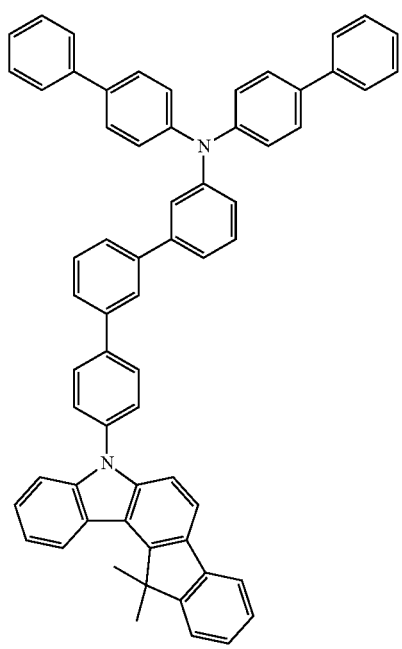 [SMILES: CC1(C)c2ccccc2-c2ccc3c(c21)c1ccccc1n3-c1ccc(-c2cccc(-c3cccc(N(c4ccc(-c5ccccc5)cc4)c4ccc(-c5ccccc5)cc4)c3)c2)cc1]
46

-continued
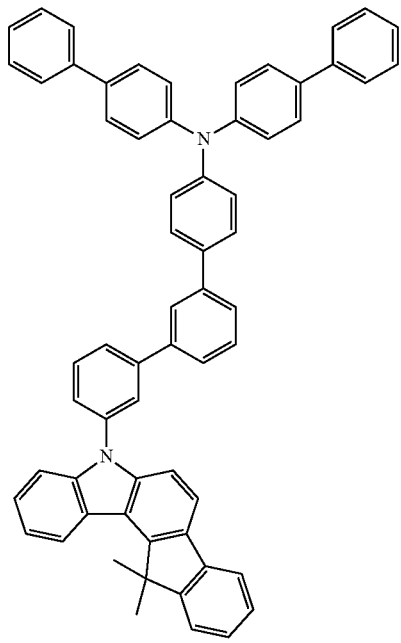 [SMILES: CC1(C)c2ccccc2-c2ccc3c(c21)c1ccccc1n3-c1cccc(-c2cccc(-c3ccc(N(c4ccc(-c5ccccc5)cc4)c4ccc(-c5ccccc5)cc4)cc3)c2)c1]
47
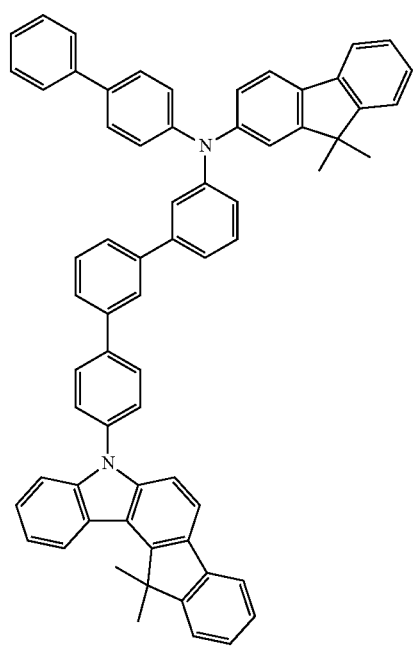 [SMILES: CC1(C)c2ccccc2-c2ccc(N(c3ccc(-c4ccccc4)cc3)c3cccc(-c4cccc(-c5ccc(-n6c7ccccc7c7c8c(ccc76)-c6ccccc6C8(C)C)cc5)c4)c3)cc21]
48

-continued
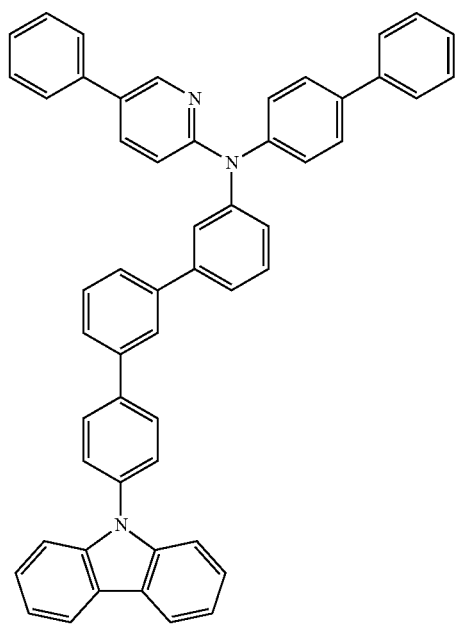
49
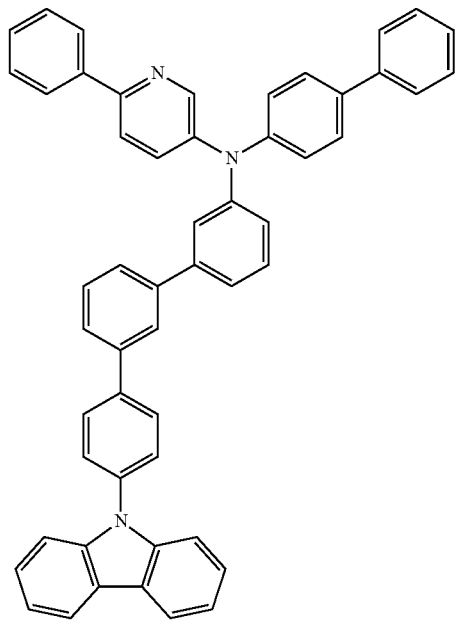 [SMILES: c1ccc(-c2ccc(N(c3ccc(-c4ccccc4)nc3)c3cccc(-c4cccc(-c5ccc(-n6c7ccccc7c7ccccc76)cc5)c4)c3)cc2)cc1]
50

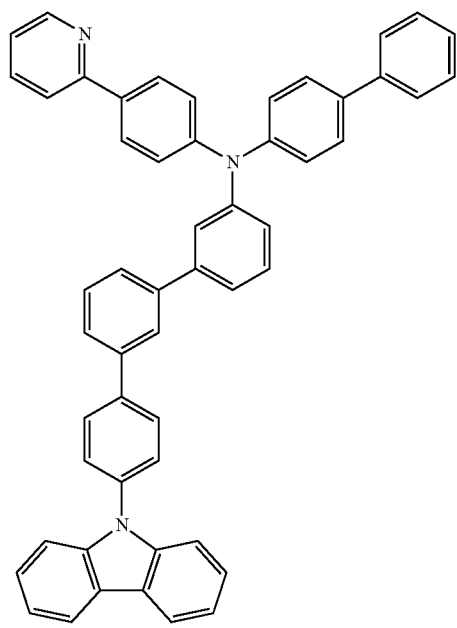 [SMILES: c1ccc(-c2ccc(N(c3ccc(-c4ccccn4)cc3)c3cccc(-c4cccc(-c5ccc(-n6c7ccccc7c7ccccc76)cc5)c4)c3)cc2)cc1]
51
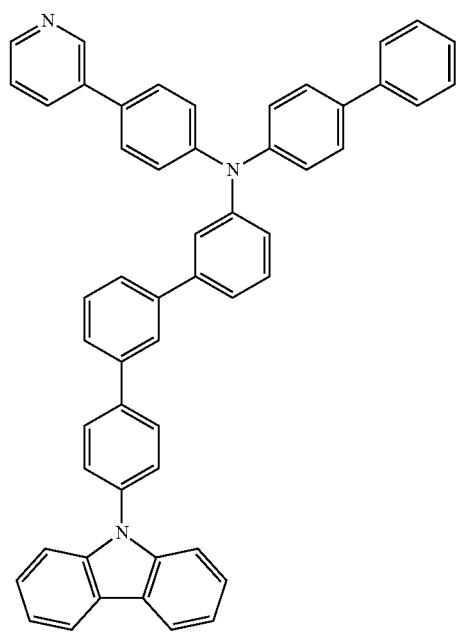 [SMILES: c1ccc(-c2ccc(N(c3ccc(-c4cccnc4)cc3)c3cccc(-c4cccc(-c5ccc(-n6c7ccccc7c7ccccc76)cc5)c4)c3)cc2)cc1]
52

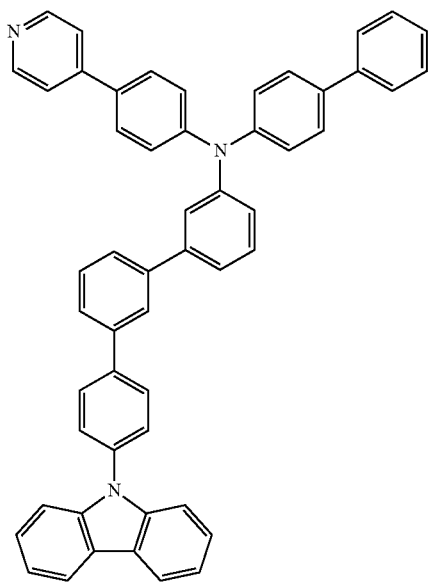 [SMILES: c1ccc(-c2ccc(N(c3ccc(-c4ccncc4)cc3)c3cccc(-c4cccc(-c5ccc(-n6c7ccccc7c7ccccc76)cc5)c4)c3)cc2)cc1]
53
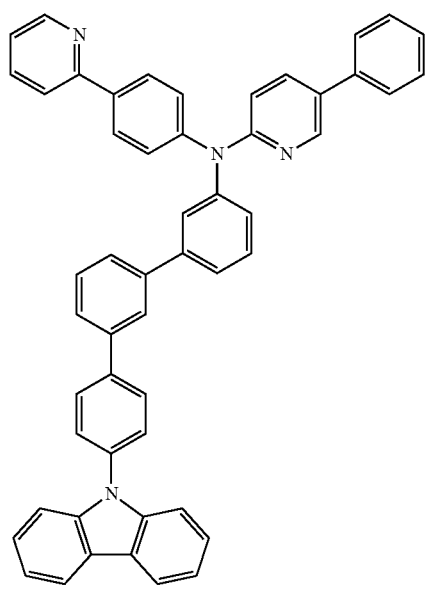 [SMILES: c1ccc(-c2ccc(N(c3ccc(-c4ccccn4)cc3)c3cccc(-c4cccc(-c5ccc(-n6c7ccccc7c7ccccc76)cc5)c4)c3)nc2)cc1]
54

-continued
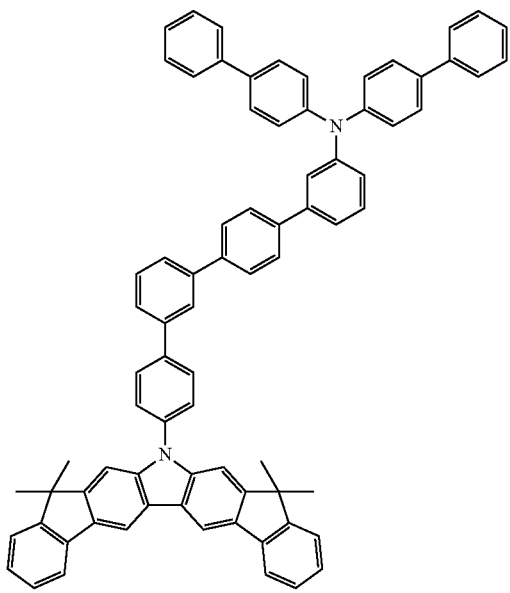 [SMILES: CC1(C)c2ccccc2-c2cc3c4cc5c(cc4n(-c4ccc(-c6cccc(-c7ccc(-c8cccc(N(c9ccc(-c%10ccccc%10)cc9)c9ccc(-c%10ccccc%10)cc9)c8)cc7)c6)cc4)c3cc21)C(C)(C)c1ccccc1-5]
55
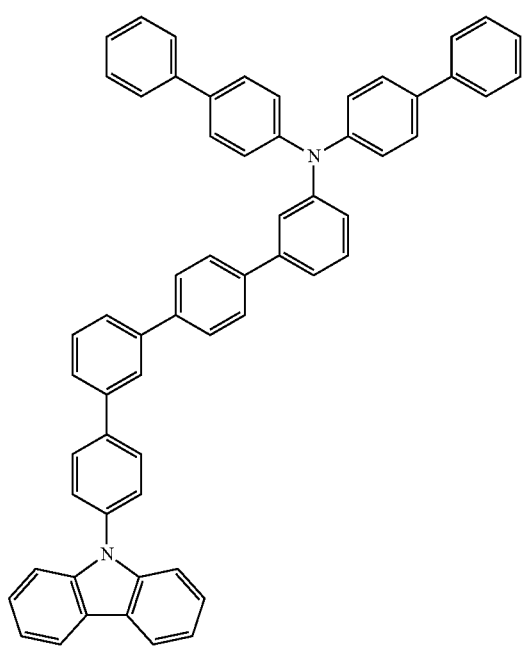 [SMILES: c1ccc(-c2ccc(N(c3ccc(-c4ccccc4)cc3)c3cccc(-c4ccc(-c5cccc(-c6ccc(-n7c8ccccc8c8ccccc87)cc6)c5)cc4)c3)cc2)cc1]
56

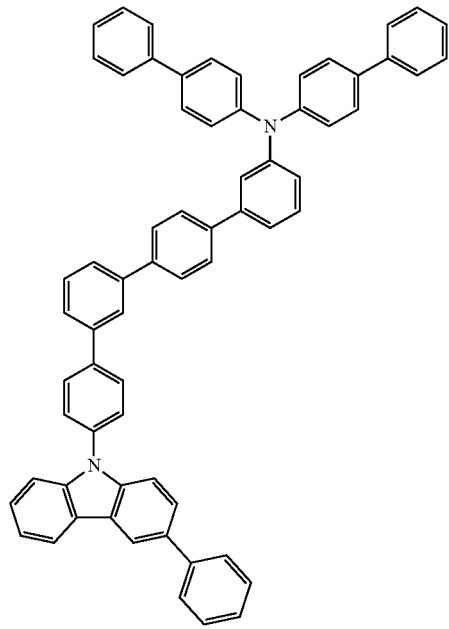 [SMILES: c1ccc(-c2ccc(N(c3ccc(-c4ccccc4)cc3)c3cccc(-c4ccc(-c5cccc(-c6ccc(-n7c8ccccc8c8cc(-c9ccccc9)ccc87)cc6)c5)cc4)c3)cc2)cc1]
57
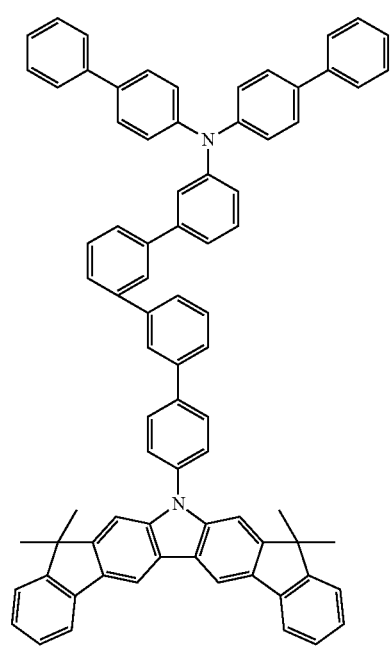 [SMILES: CC1(C)c2ccccc2-c2cc3c4cc5c(cc4n(-c4ccc(-c6cccc(-c7cccc(-c8cccc(N(c9ccc(-c%10ccccc%10)cc9)c9ccc(-c%10ccccc%10)cc9)c8)c7)c6)cc4)c3cc21)C(C)(C)c1ccccc1-5]
58

-continued
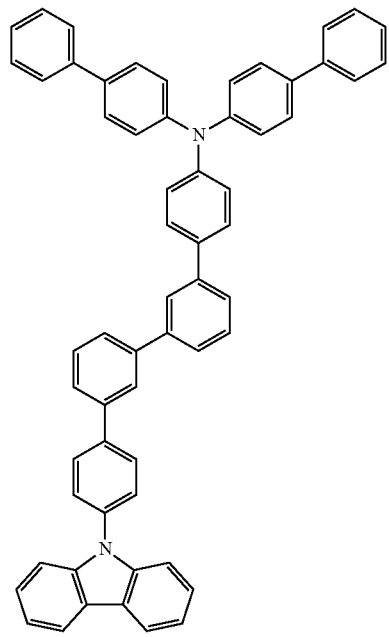 [SMILES: c1ccc(-c2ccc(N(c3ccc(-c4ccccc4)cc3)c3ccc(-c4cccc(-c5cccc(-c6ccc(-n7c8ccccc8c8ccccc87)cc6)c5)c4)cc3)cc2)cc1]
59
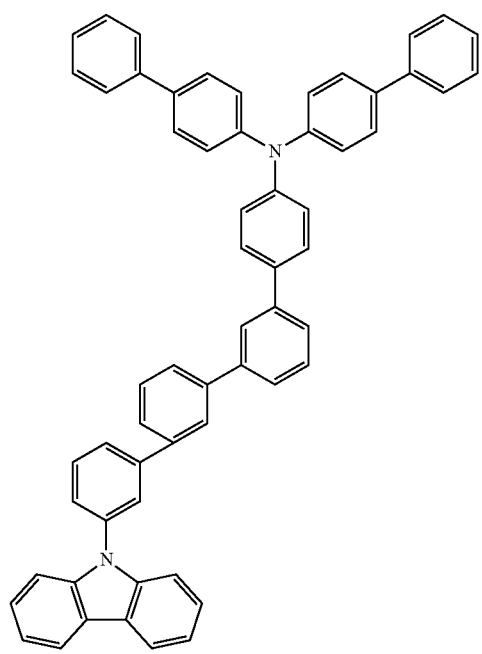 [SMILES: c1ccc(-c2ccc(N(c3ccc(-c4ccccc4)cc3)c3ccc(-c4cccc(-c5cccc(-c6cccc(-n7c8ccccc8c8ccccc87)c6)c5)c4)cc3)cc2)cc1]
60

-continued
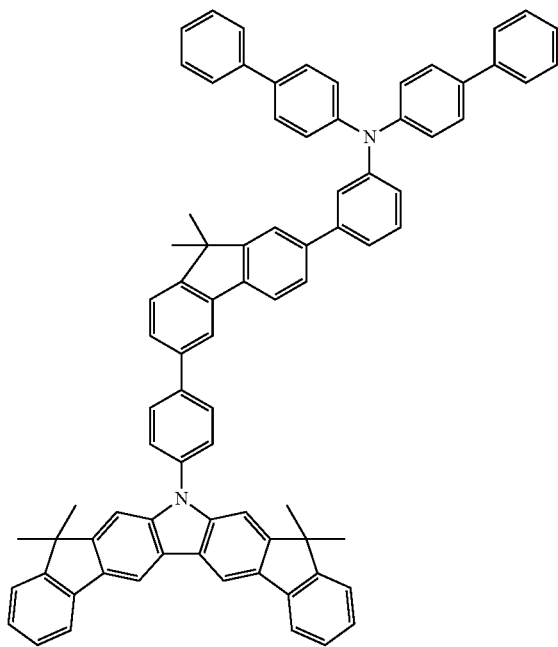 [SMILES: CC1(C)c2ccc(-c3ccc(-n4c5cc6c(cc5c5cc7c(cc54)C(C)(C)c4ccccc4-7)-c4ccccc4C6(C)C)cc3)cc2-c2ccc(-c3cccc(N(c4ccc(-c5ccccc5)cc4)c4ccc(-c5ccccc5)cc4)c3)cc21]
61
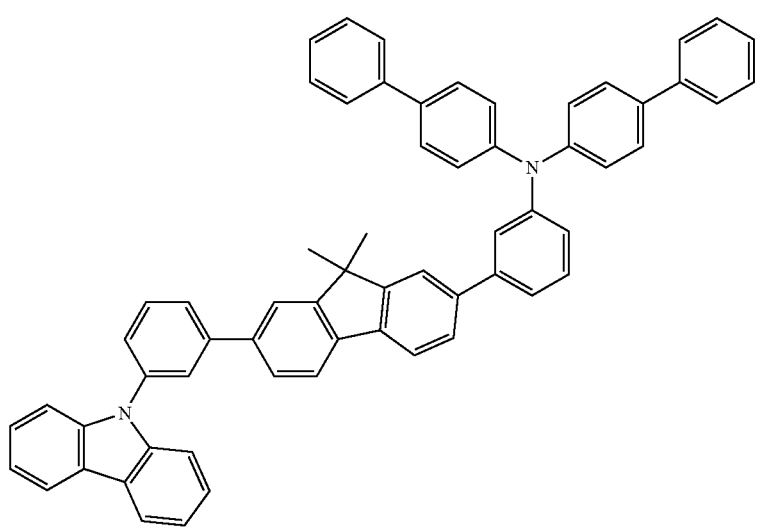 [SMILES: CC1(C)c2cc(-c3cccc(N(c4ccc(-c5ccccc5)cc4)c4ccc(-c5ccccc5)cc4)c3)ccc2-c2ccc(-c3cccc(-n4c5ccccc5c5ccccc54)c3)cc21]
62

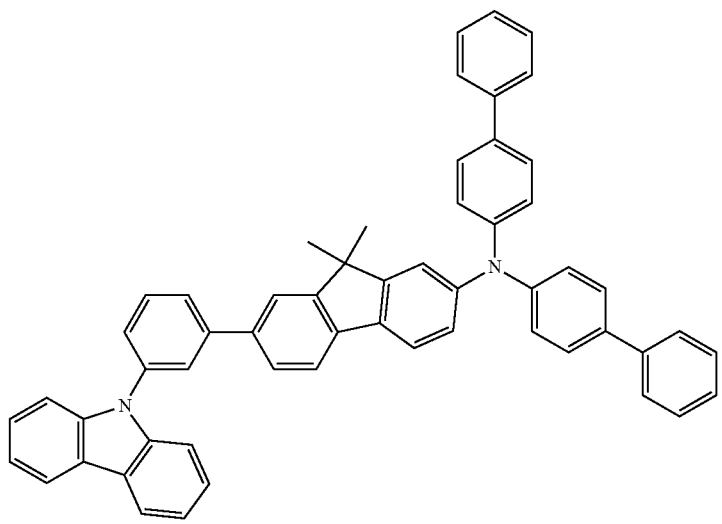 [SMILES: CC1(C)c2cc(-c3cccc(-n4c5ccccc5c5ccccc54)c3)ccc2-c2ccc(N(c3ccc(-c4ccccc4)cc3)c3ccc(-c4ccccc4)cc3)cc21]
63
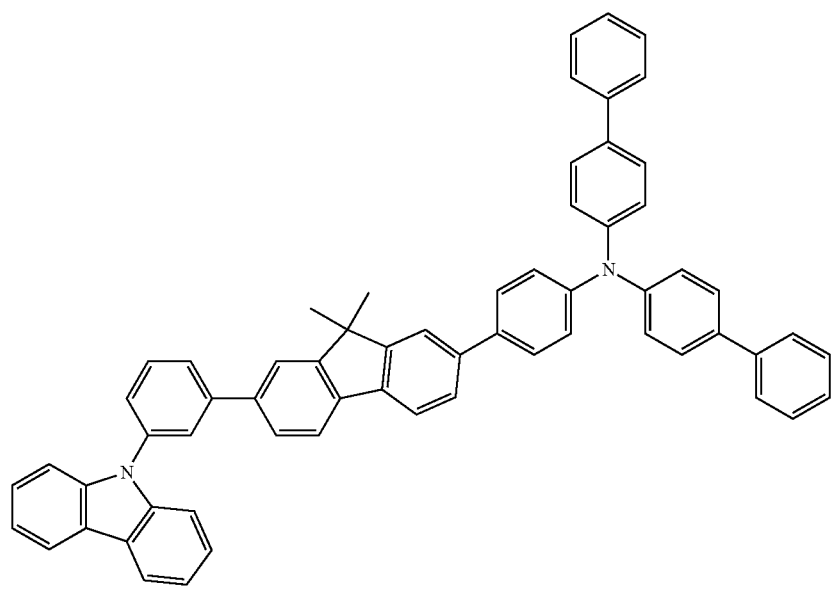 [SMILES: CC1(C)c2cc(-c3ccc(N(c4ccc(-c5ccccc5)cc4)c4ccc(-c5ccccc5)cc4)cc3)ccc2-c2ccc(-c3cccc(-n4c5ccccc5c5ccccc54)c3)cc21]
64
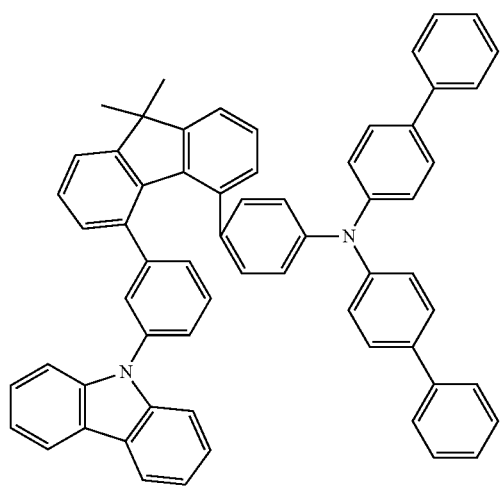 [SMILES: CC1(C)c2cccc(-c3ccc(N(c4ccc(-c5ccccc5)cc4)c4ccc(-c5ccccc5)cc4)cc3)c2-c2c(-c3cccc(-n4c5ccccc5c5ccccc54)c3)cccc21]
65

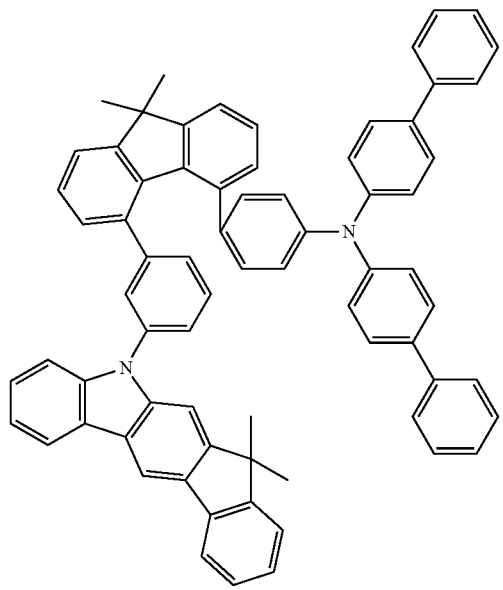 [SMILES: CC1(C)c2ccccc2-c2cc3c4ccccc4n(-c4cccc(-c5cccc6c5-c5c(-c7ccc(N(c8ccc(-c9ccccc9)cc8)c8ccc(-c9ccccc9)cc8)cc7)cccc5C6(C)C)c4)c3cc21]
66
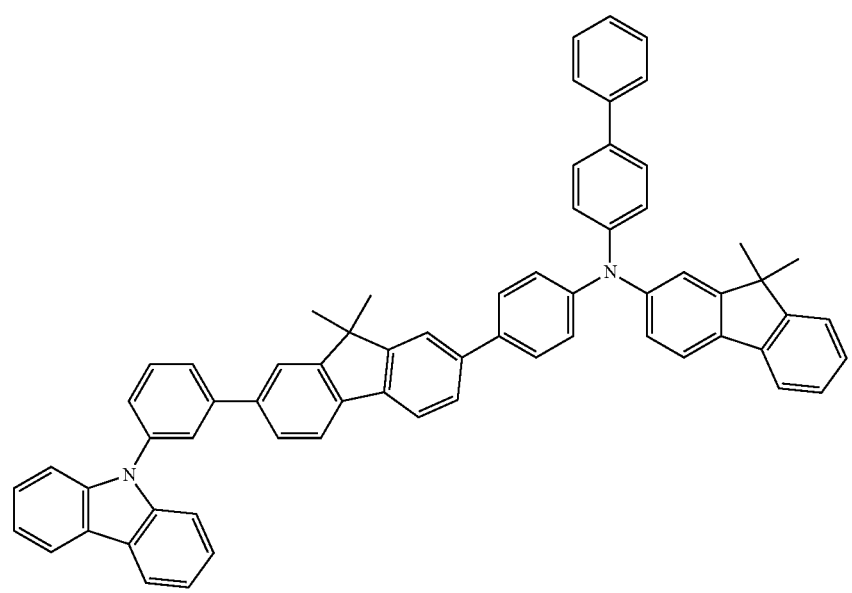 [SMILES: CC1(C)c2cc(-c3ccc(N(c4ccc(-c5ccccc5)cc4)c4ccc5c(c4)C(C)(C)c4ccccc4-5)cc3)ccc2-c2ccc(-c3cccc(-n4c5ccccc5c5ccccc54)c3)cc21]
67

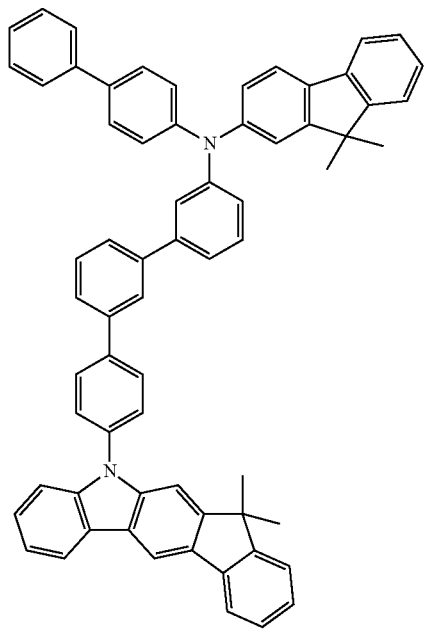 [SMILES: CC1(C)c2ccccc2-c2ccc(N(c3ccc(-c4ccccc4)cc3)c3cccc(-c4cccc(-c5ccc(-n6c7ccccc7c7cc8c(cc76)C(C)(C)c6ccccc6-8)cc5)c4)c3)cc21]
68
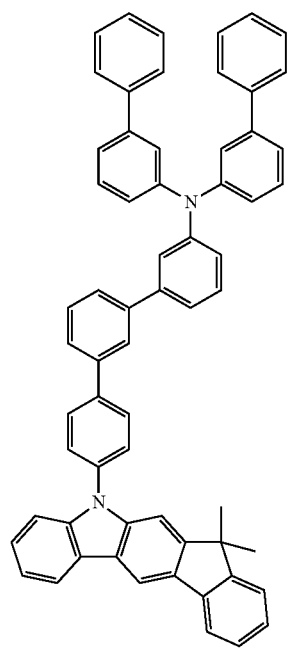 [SMILES: CC1(C)c2ccccc2-c2cc3c4ccccc4n(-c4ccc(-c5cccc(-c6cccc(N(c7cccc(-c8ccccc8)c7)c7cccc(-c8ccccc8)c7)c6)c5)cc4)c3cc21]
69

-continued
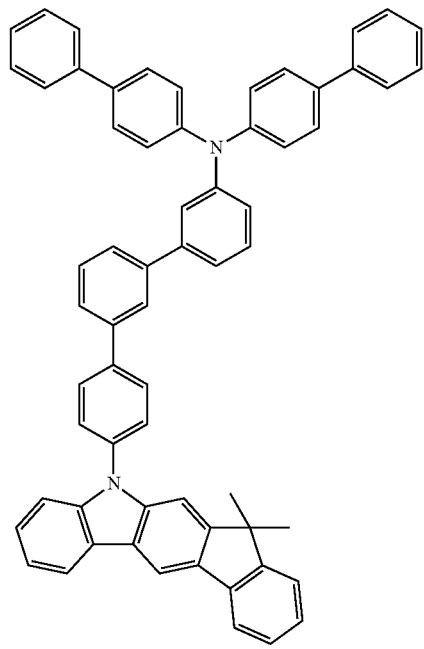 [SMILES: CC1(C)c2ccccc2-c2cc3c4ccccc4n(-c4ccc(-c5cccc(-c6cccc(N(c7ccc(-c8ccccc8)cc7)c7ccc(-c8ccccc8)cc7)c6)c5)cc4)c3cc21]
70
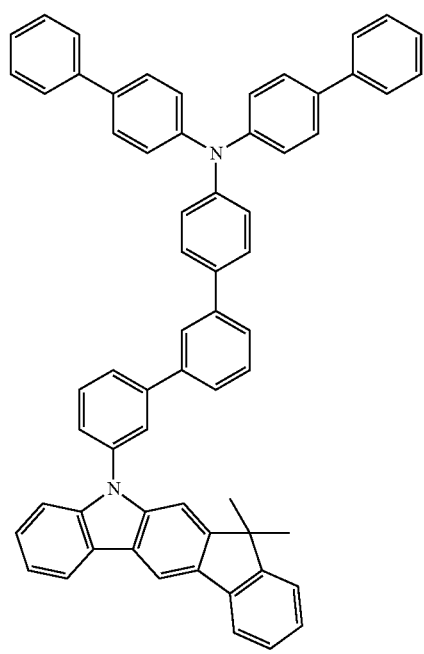 [SMILES: CC1(C)c2ccccc2-c2cc3c4ccccc4n(-c4cccc(-c5cccc(-c6ccc(N(c7ccc(-c8ccccc8)cc7)c7ccc(-c8ccccc8)cc7)cc6)c5)c4)c3cc21]
71

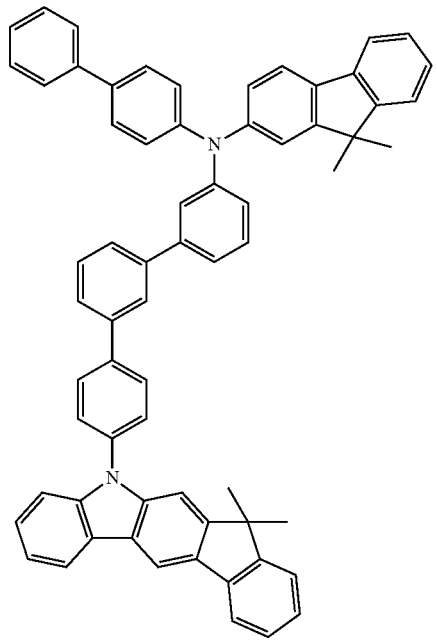 [SMILES: CC1(C)c2ccccc2-c2ccc(N(c3ccc(-c4ccccc4)cc3)c3cccc(-c4cccc(-c5ccc(-n6c7ccccc7c7cc8c(cc76)C(C)(C)c6ccccc6-8)cc5)c4)c3)cc21]

72

The compounds according to the invention can be prepared using generally known processes of organic synthetic chemistry, for example Buchwald coupling, Ullmann coupling and Suzuki coupling.

A preferred generally usable process for the preparation of compounds of the formula (I) is presented below (Scheme 1).

Scheme 1

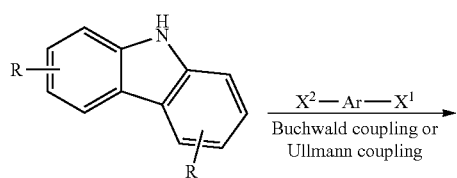

X¹/X² = reactive group, for example halide
R = any desired organic radical
Ar, Ar', Ar'' = any desired aromatic or heteroaromatic ring system

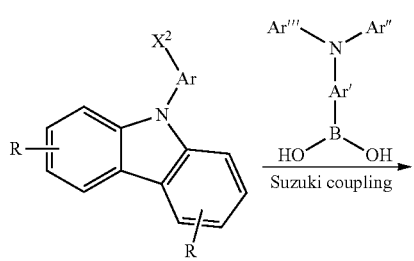

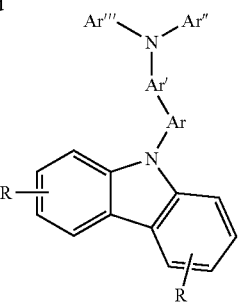

To this end, an N-arylcarbazole derivative is prepared starting from carbazole derivatives having a free N—H function in a coupling reaction, preferably a Buchwald coupling or an Ullmann coupling, with an aryl compound. The carbazole derivatives are either commercially available or can be prepared in a simple manner. Instead of simple carbazole, it is also possible to use, for example, indenocarbazole or other derivatives of carbazole.

The aryl compound with which the coupling reaction is carried out preferably contains two reactive functional groups, meaning that it can be reacted with an arylamino compound in a further coupling reaction, preferably in a Suzuki coupling. Aryl compounds of this type containing two reactive functional groups are likewise in many cases commercially available or can be prepared in a simple manner.

Finally, the compound of the formula (I) according to the invention can be obtained by the Suzuki coupling reaction. Further reaction steps may optionally follow, for example functionalisation reactions, in order to obtain the final compounds of the formula (I).

The illustrative process shown is particularly suitable for preparing compounds according to the invention. However, alternative processes are conceivable and possibly to be preferred in certain cases. Correspondingly, the person skilled in the art will be able to modify the process shown above within the scope of his general expert knowledge.

the invention thus furthermore relates to a process for the preparation of a compound of the formula (I), characterised in that a carbazole derivative is reacted with an aryl compound in a coupling reaction.

The coupling reaction is preferably a Buchwald coupling. The aryl compound is furthermore preferably a compound containing two reactive groups, one of which reacts in the first coupling reaction, while the other reacts in a second, subsequent coupling reaction. The second, subsequent coupling reaction is a preferably a reaction with an arylamino compound, preferably a Suzuki coupling reaction.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), where the bond(s) to the polymer, oligomer or dendrimer may be localised at any desired positions in formula (I) which are substituted by $R^1$ or $R^2$. Depending on the linking of the compound of the formula (I) the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) may be linked via a trivalent or polyvalent group, for example via a trivalent or polyvalent aromatic or heteroaromatic group, to form a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula ((I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecyl-benzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) according to the invention are suitable for use in electronic devices, in particular in organic electroluminescent devices (OLEDs). Depending on the substitution, the compounds are employed in different functions and layers.

The invention therefore furthermore relates to the use of a compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (I). The electronic device here is preferably selected from the devices mentioned above. Particular preference is given to an organic electroluminescent device comprising anode, cathode and at least one emitting layer, characterised in that at least one organic layer, which may be an emitting layer, a hole-transport layer or another layer, comprises at least one compound of the formula (I). The compound of the formula (I) is preferably present in a hole-transport layer, a hole-injection layer, an electron-blocking layer or in an emitting layer.

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or in-organic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the organic electroluminescent device is preferably the following: anode-hole-injection layer-hole-transport layer-emitting layer-electron-transport layer-electron-injection layer-cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). The compounds according to the invention may alternatively and/or additionally also be present in the hole-transport layer or in another layer.

It should be noted that, for the generation of white light, an emitter compound used individually which emits in a broad wavelength range may also be suitable instead of a plurality of emitter compounds emitting in colour.

It is preferred in accordance with the invention if the compound of the formula (I) is employed in an electronic device comprising one or more phosphorescent dopants. The compound can be used in various layers here, preferably in a hole-transport layer, a hole-injection layer, an electron-blocking layer or in an emitting layer.

The term phosphorescent dopants typically encompasses compounds in which the light emission takes place through a spin-forbidden transition, for example a transition from an excited triplet state or a state having a higher spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able, without inventive step, to employ further phosphorescent complexes in combination with the compounds of the formula (I) in organic electroluminescent devices.

Explicit examples of suitable phosphorescent emitter compounds can be obtained from a table below.

However, the compound of the formula (I) can also be employed in accordance with the invention in an electronic device comprising one or more fluorescent dopants.

In a preferred embodiment of the invention, the compounds of the formula (I) are employed as hole-transport material. The compounds are then preferably employed in a hole-transport layer, an electron-blocking layer or a hole-injection layer.

A hole-transport layer in accordance with the present application is a layer having a hole-transporting function which is located between anode and emitting layer.

Hole-injection layers and electron-blocking layers in the sense of the present invention are taken to be specific embodiments of hole-transport layers. In the case of a plurality of hole-transport layers between anode and emitting layer, a hole-injection layer is a hole-transport layer which is directly adjacent to the anode or is only separated therefrom by a single coating of the anode. In the case of a plurality of hole-transport layers between anode and emitting layer, an electron-blocking layer is the hole-transport layer which is directly adjacent to the emitting layer on the anode side.

If the compound of the formula (I) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) then additionally comprises one or more p-dopants. In accordance with the present invention, the p-dopants employed are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600 and WO 2012/095143.

In a further preferred embodiment of the invention, the compound of the formula (I) is used as hole-transport material in combination with a hexaazatriphenylene derivative, as described in US 2007/0092755. The hexaazatriphenylene derivative here is particularly preferably employed in a separate layer.

In a further embodiment of the present invention, the compounds of the formula (I) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the larger.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopants is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the larger. In individual cases, however, the proportion of an individual matrix material in the system may be smaller than the proportion of an individual dopant.

In a further preferred embodiment of the invention, the compounds of the formula (I) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

The mixed-matrix systems may comprise one or more dopants, preferably one or more phosphorescent dopants. In general, mixed-matrix systems are preferably employed in phosphorescent organic electroluminescent devices.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant compound is employed in the mixed-matrix system.

Preferred phosphorescent dopants for use in mixed-matrix systems are the phosphorescent dopants shown above and in a following table.

Materials preferably employed in the devices according to the invention are shown below, arranged in accordance with their use and function.

Explicit examples of phosphorescent dopants are shown in the following table.

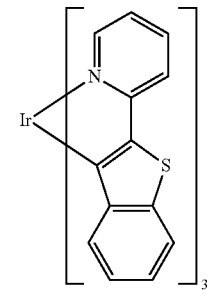

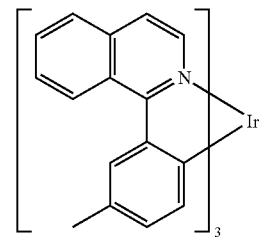

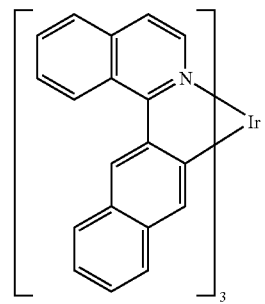

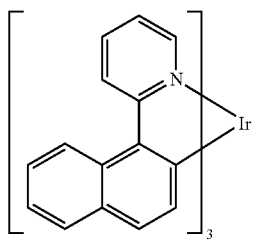
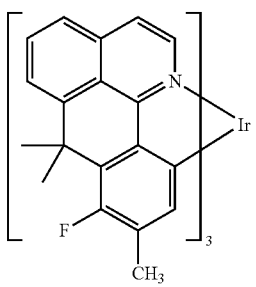
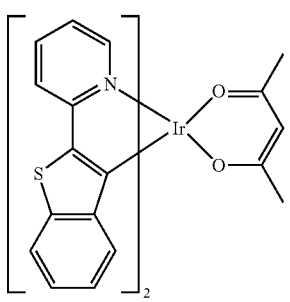
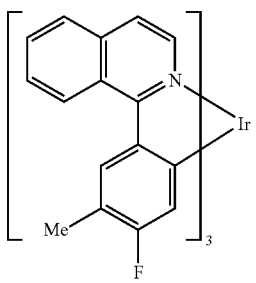
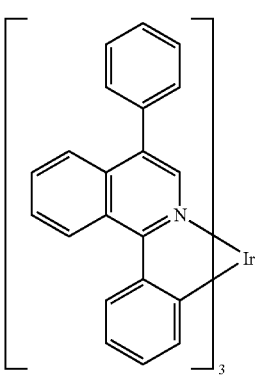
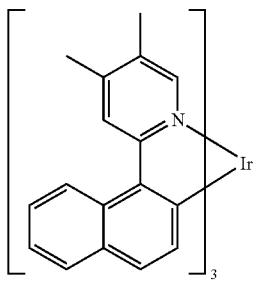
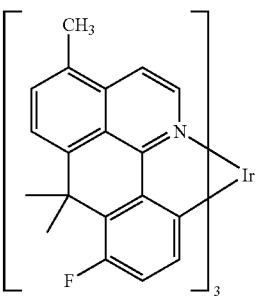
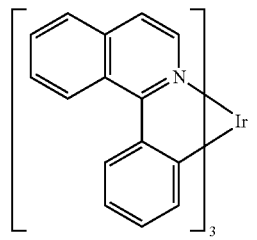
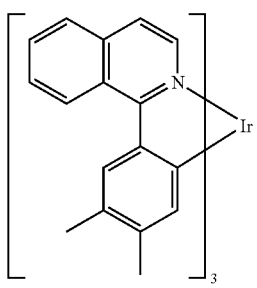
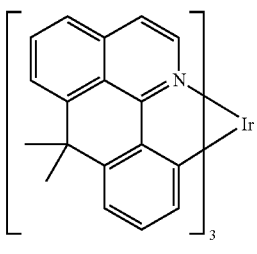
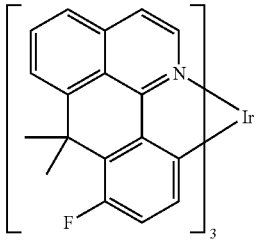

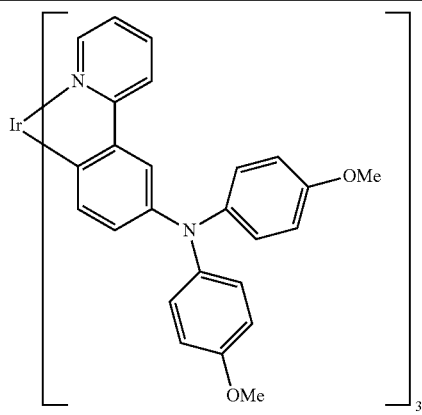
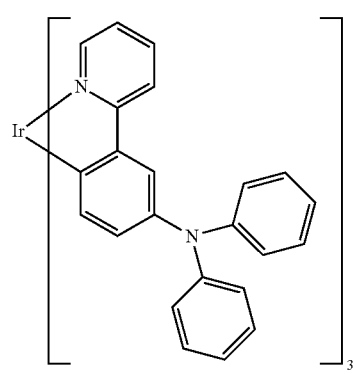
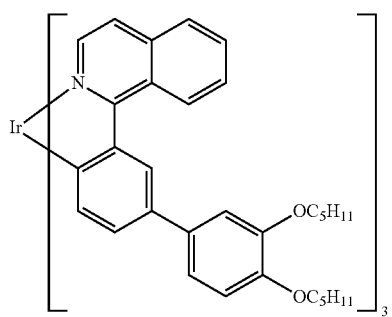
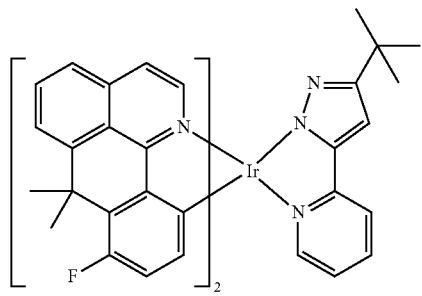
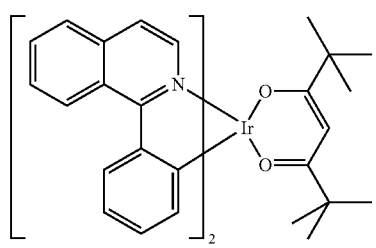
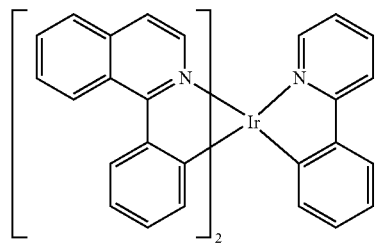
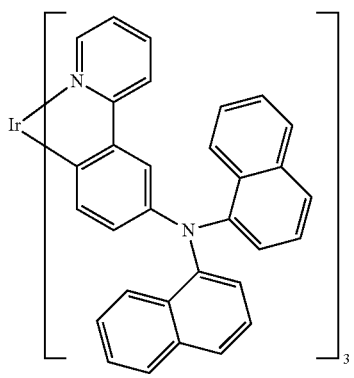
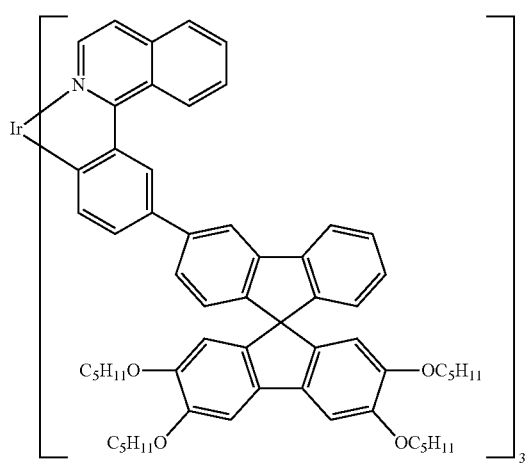
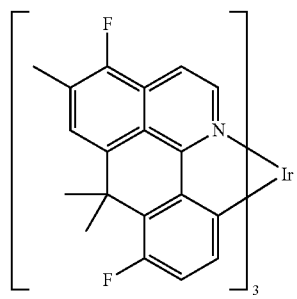
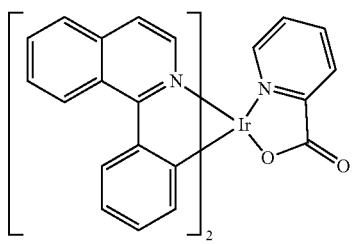

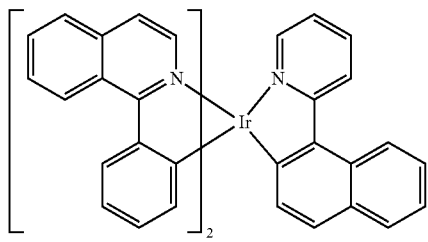
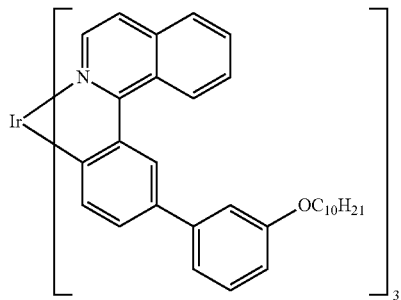
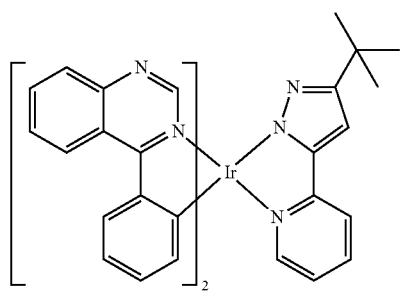
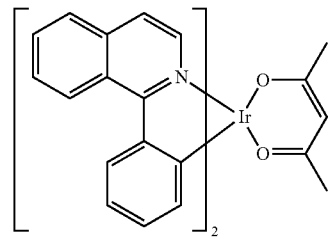
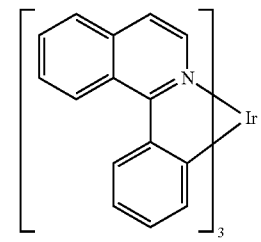
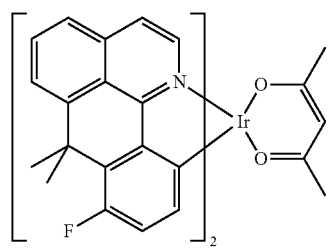
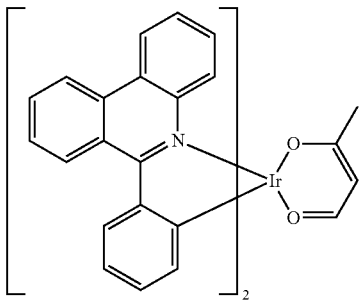
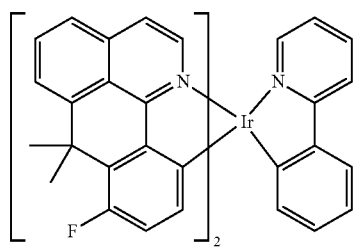
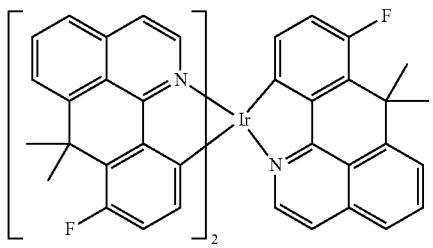
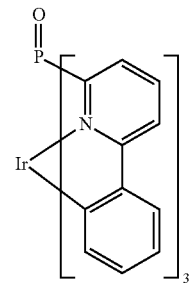
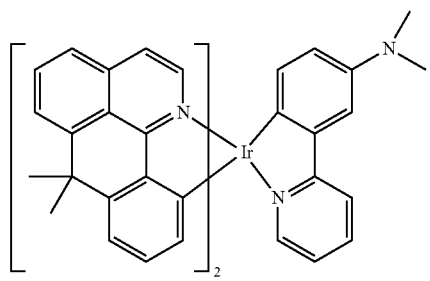
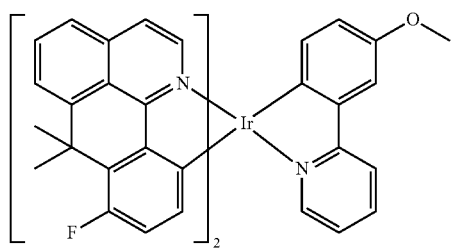

-continued
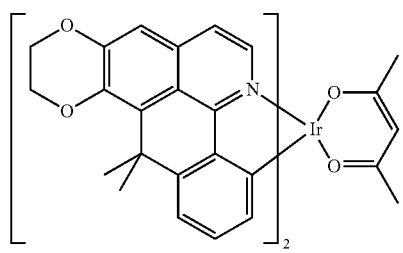
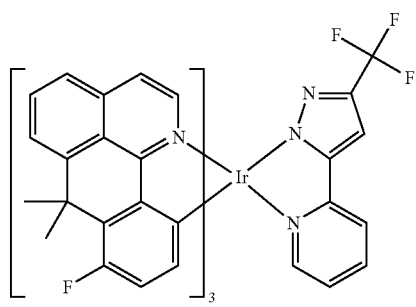
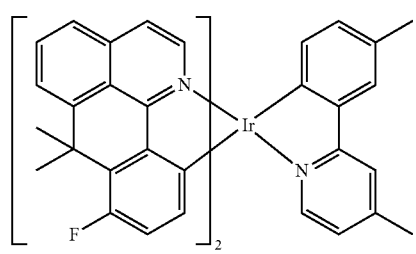
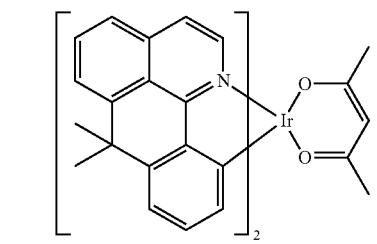
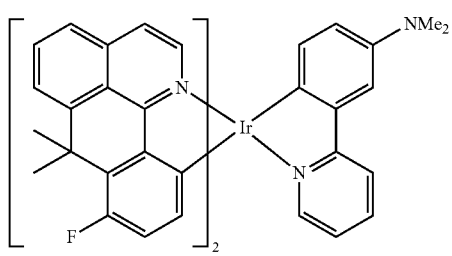
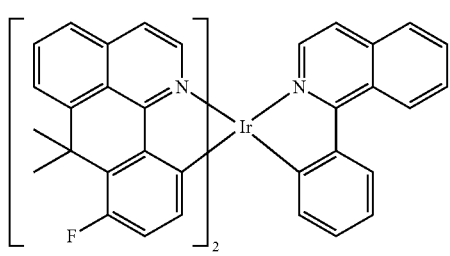
-continued
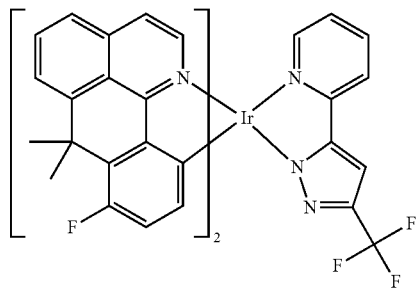
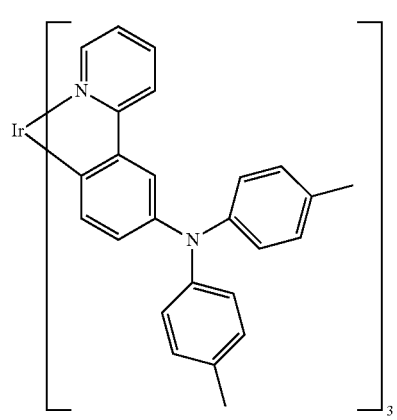
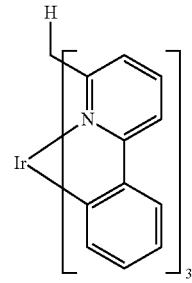
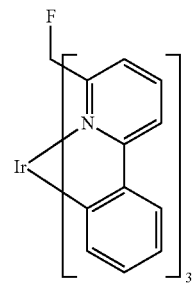
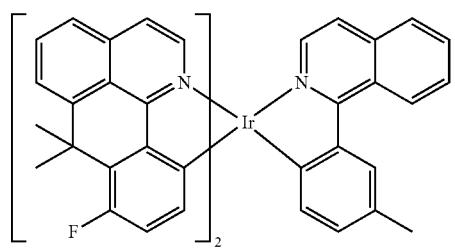

-continued
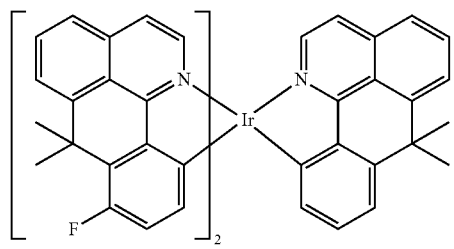
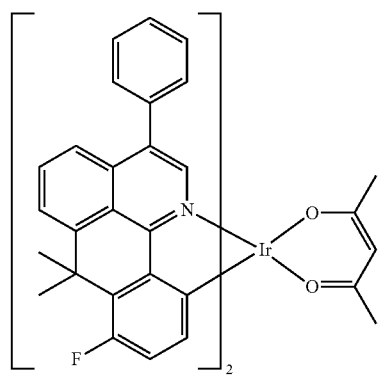
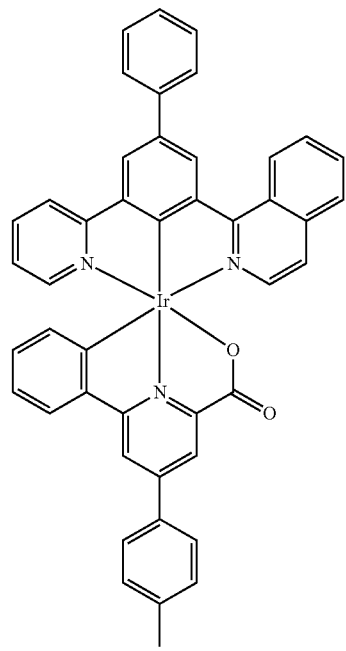
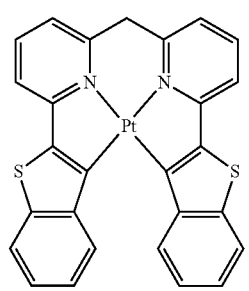
-continued
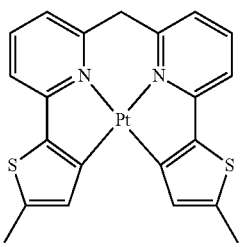
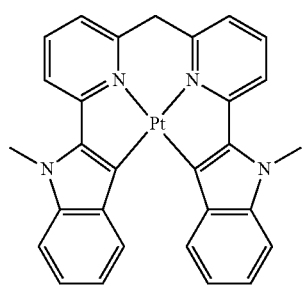
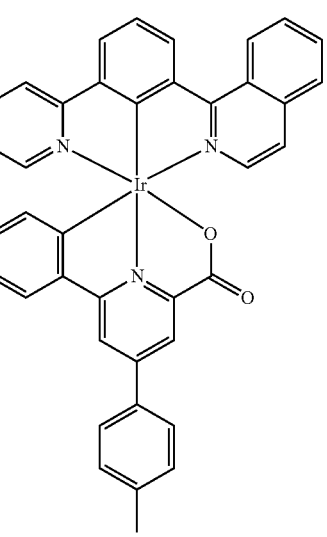
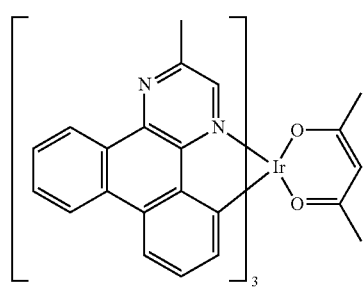

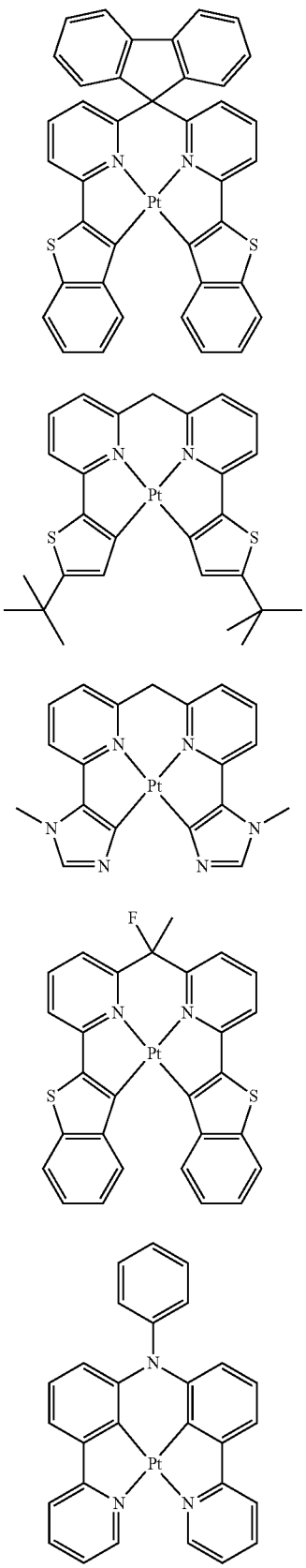
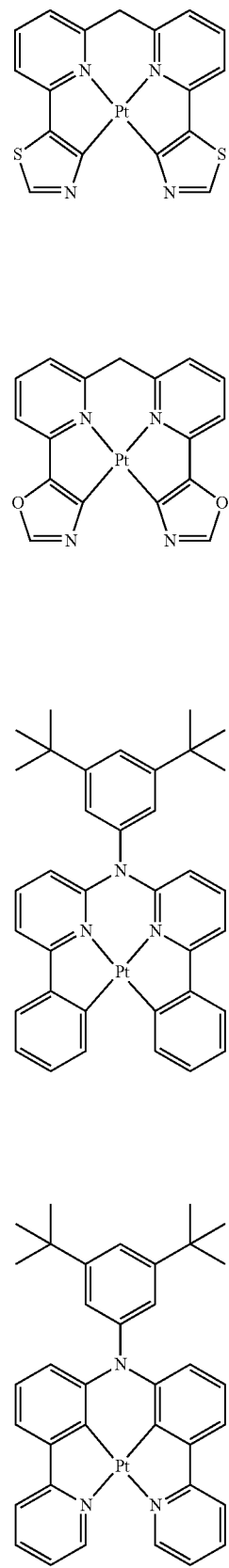

101
-continued
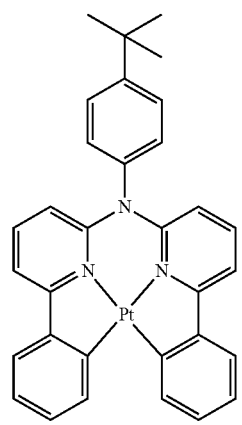
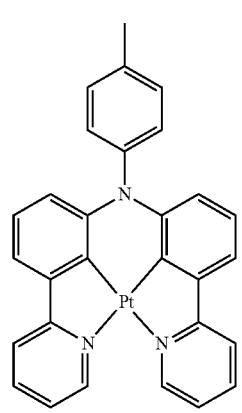
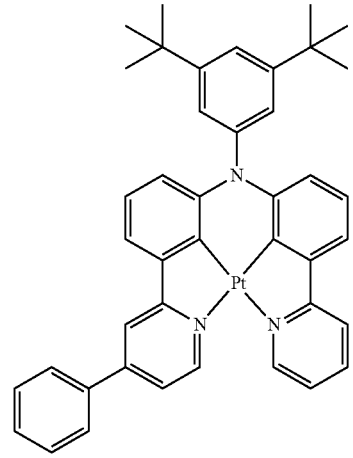
102
-continued
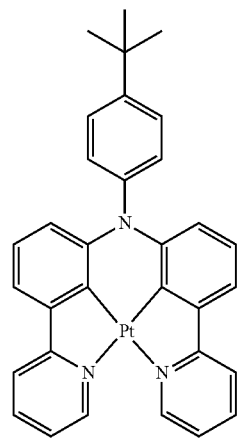
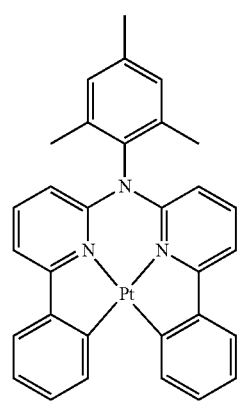
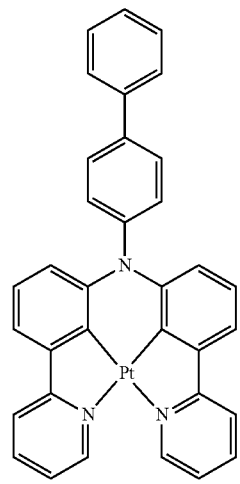

| 103 -continued | 104 -continued |
|---|---|
| 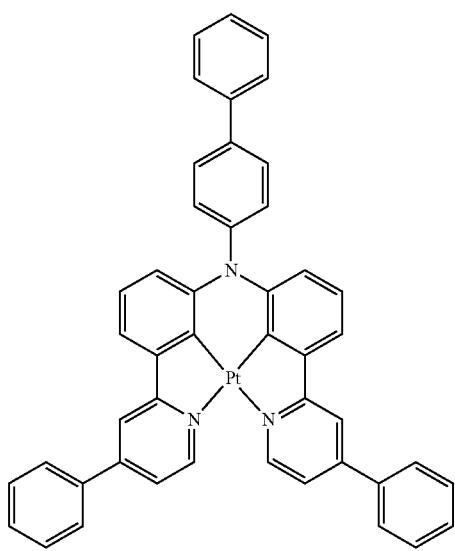 | 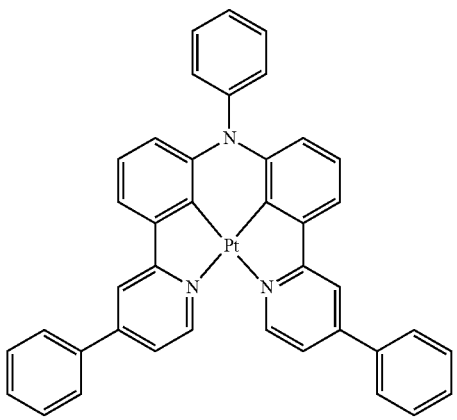 |
| 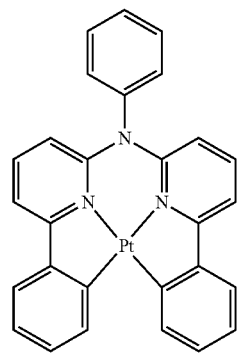 | 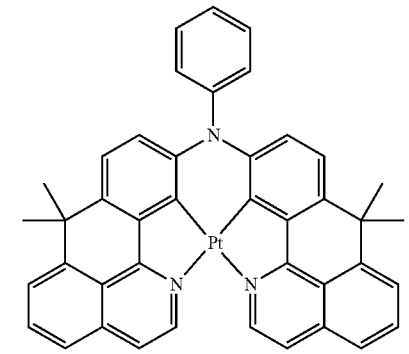 |
| | 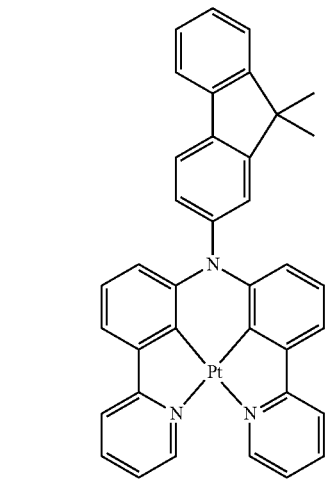 |
| 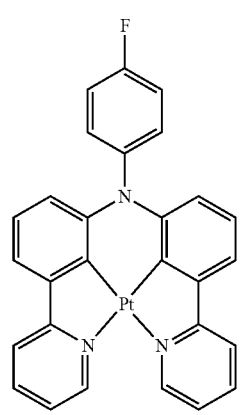 | 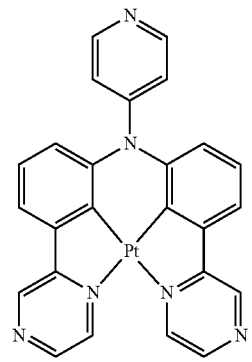 |

105
-continued
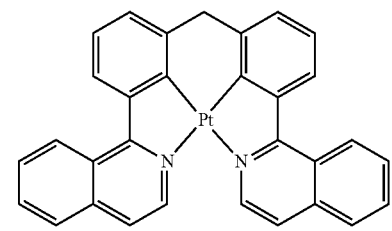
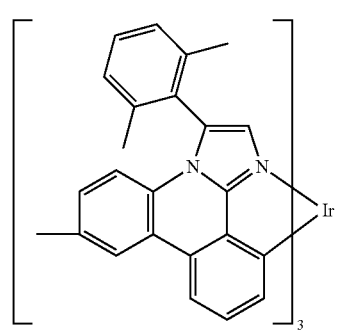
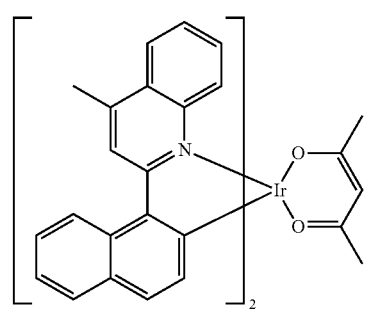
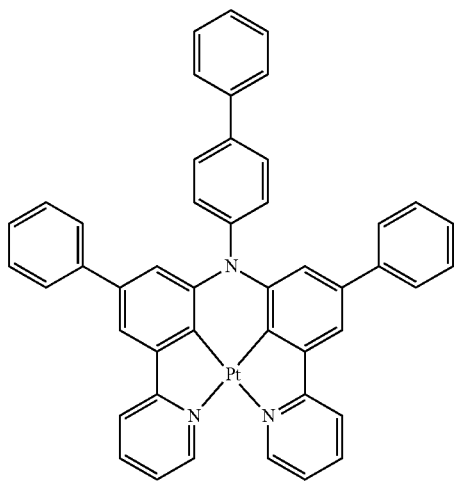
106
-continued
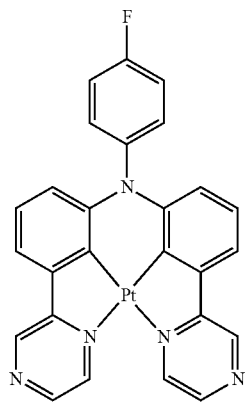
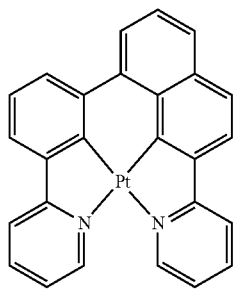
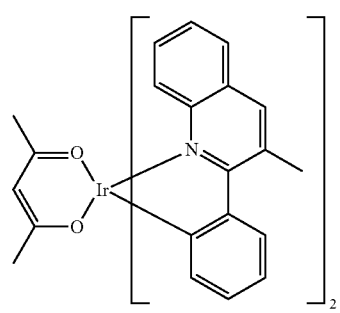
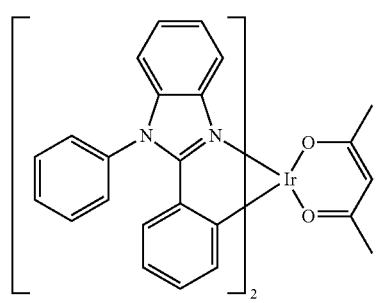

-continued
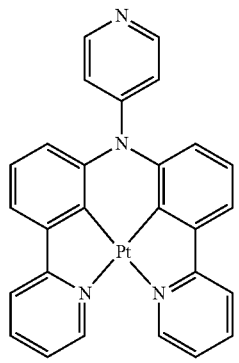
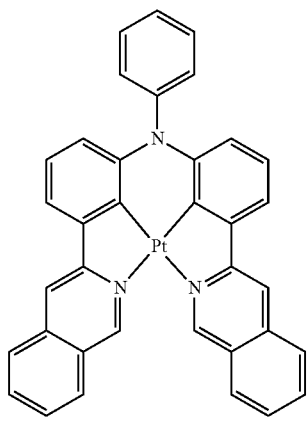
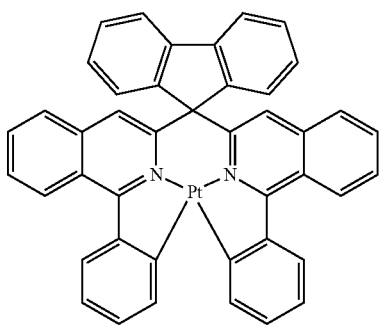
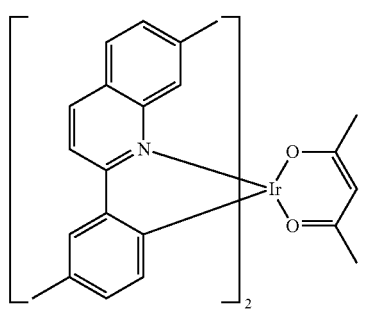
-continued
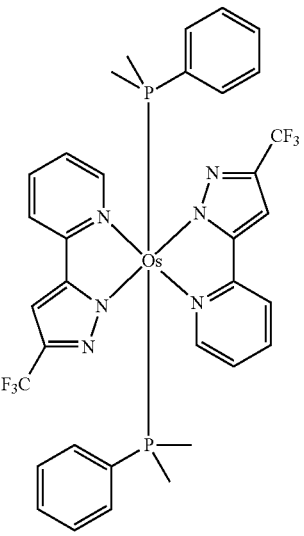
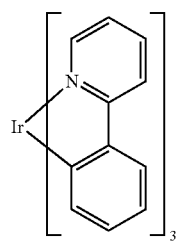
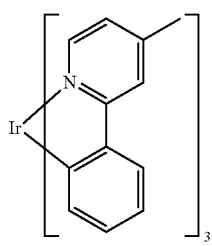
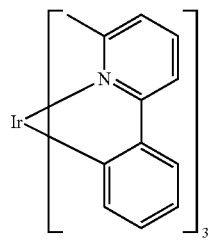
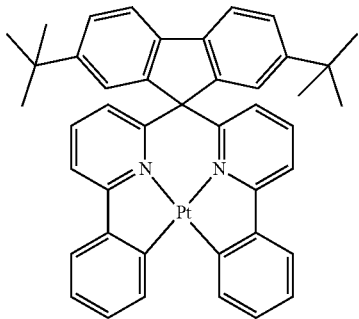

109
-continued
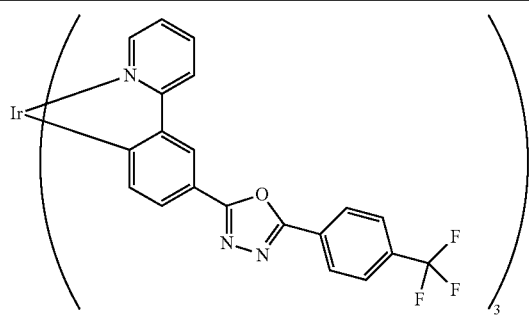
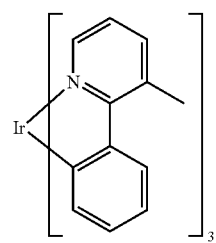
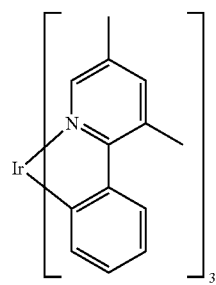
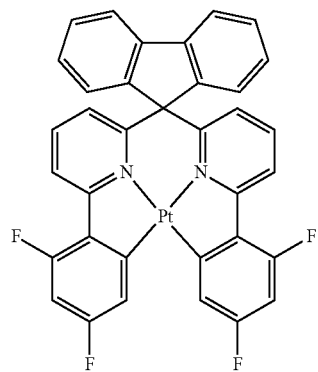
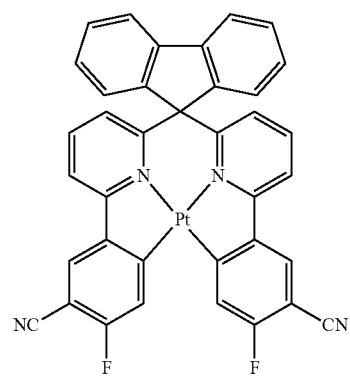
110
-continued
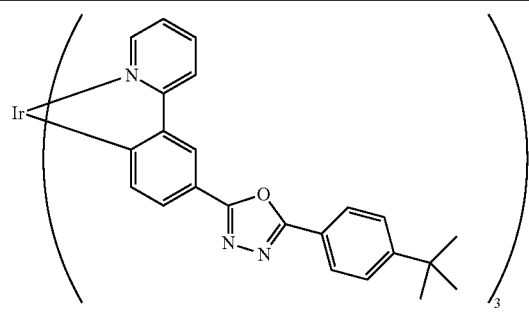
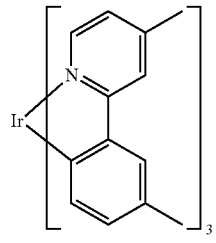
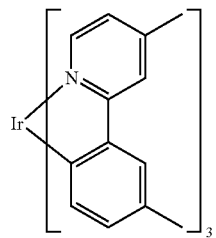
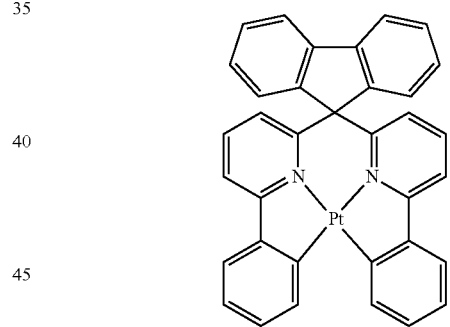
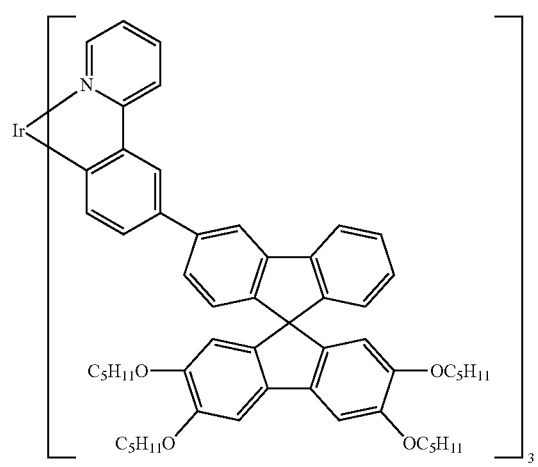

111
-continued
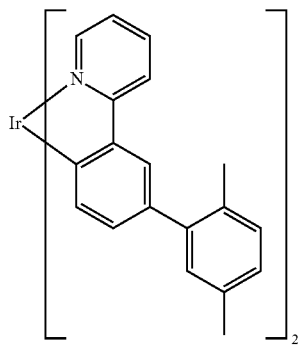
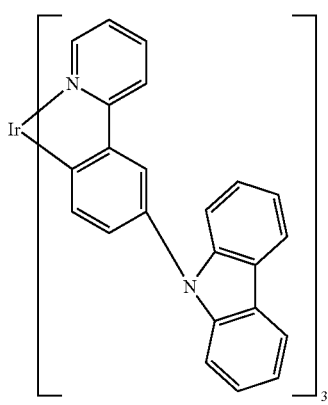
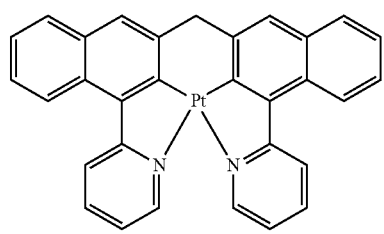
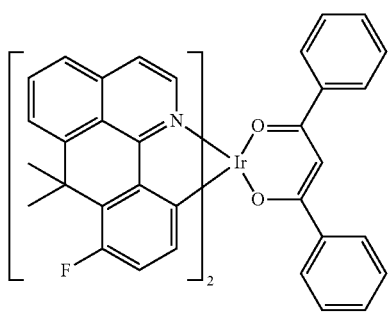
112
-continued
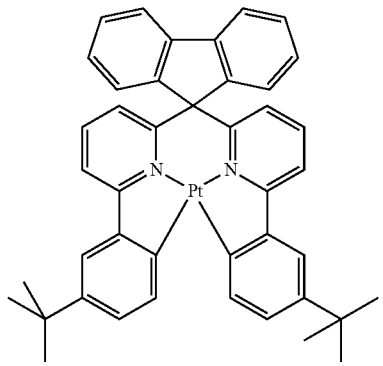
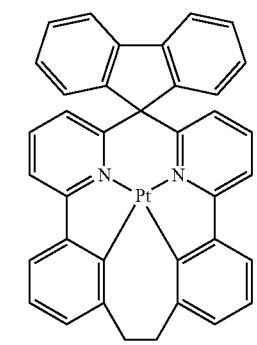
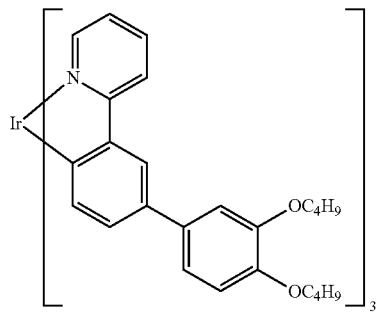
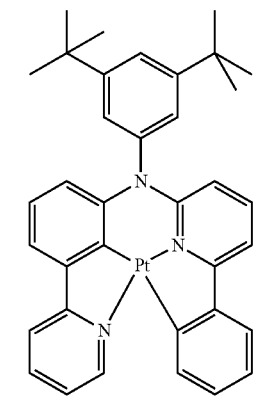

113
-continued
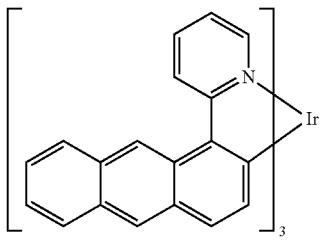
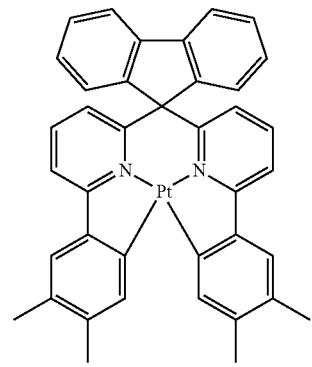
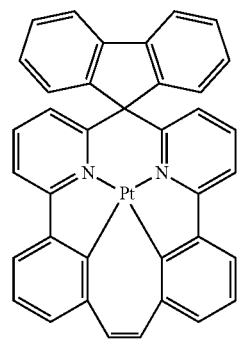
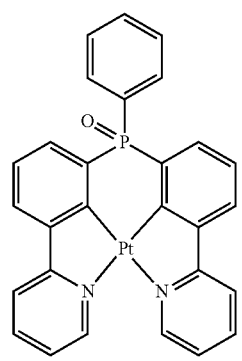
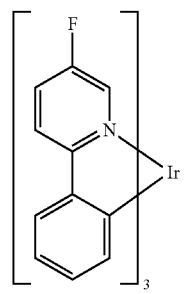
114
-continued
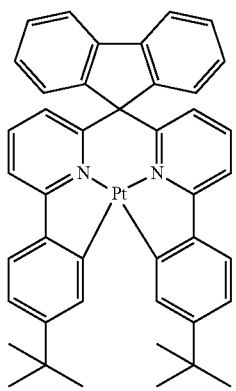
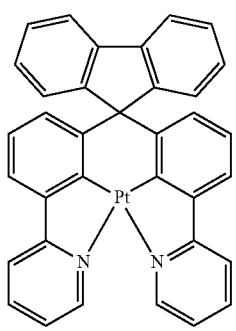
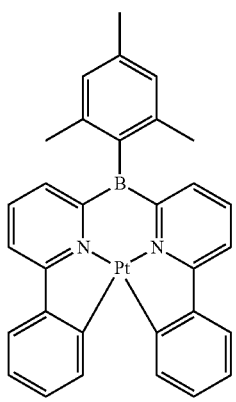
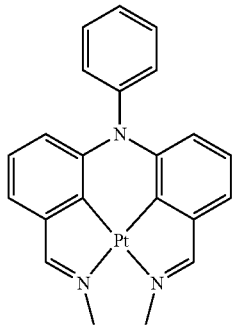

| 115 -continued | 116 -continued |
|---|---|
| 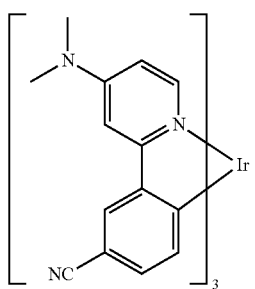 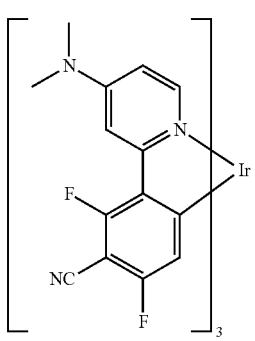 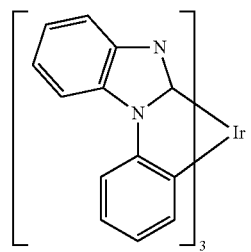 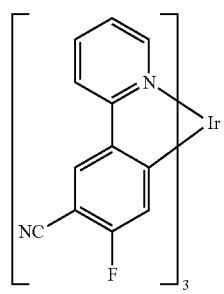 | 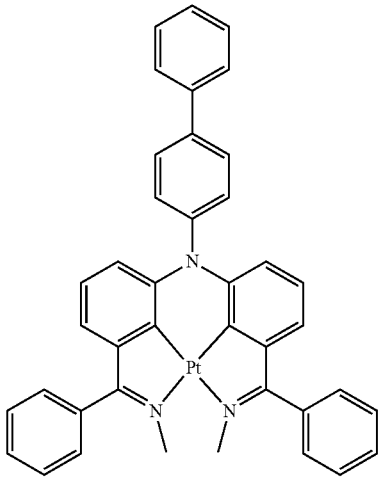 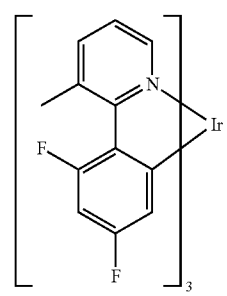 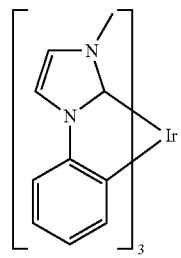 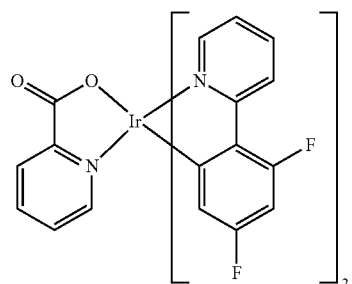 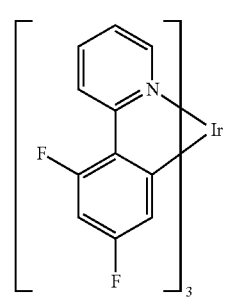 |

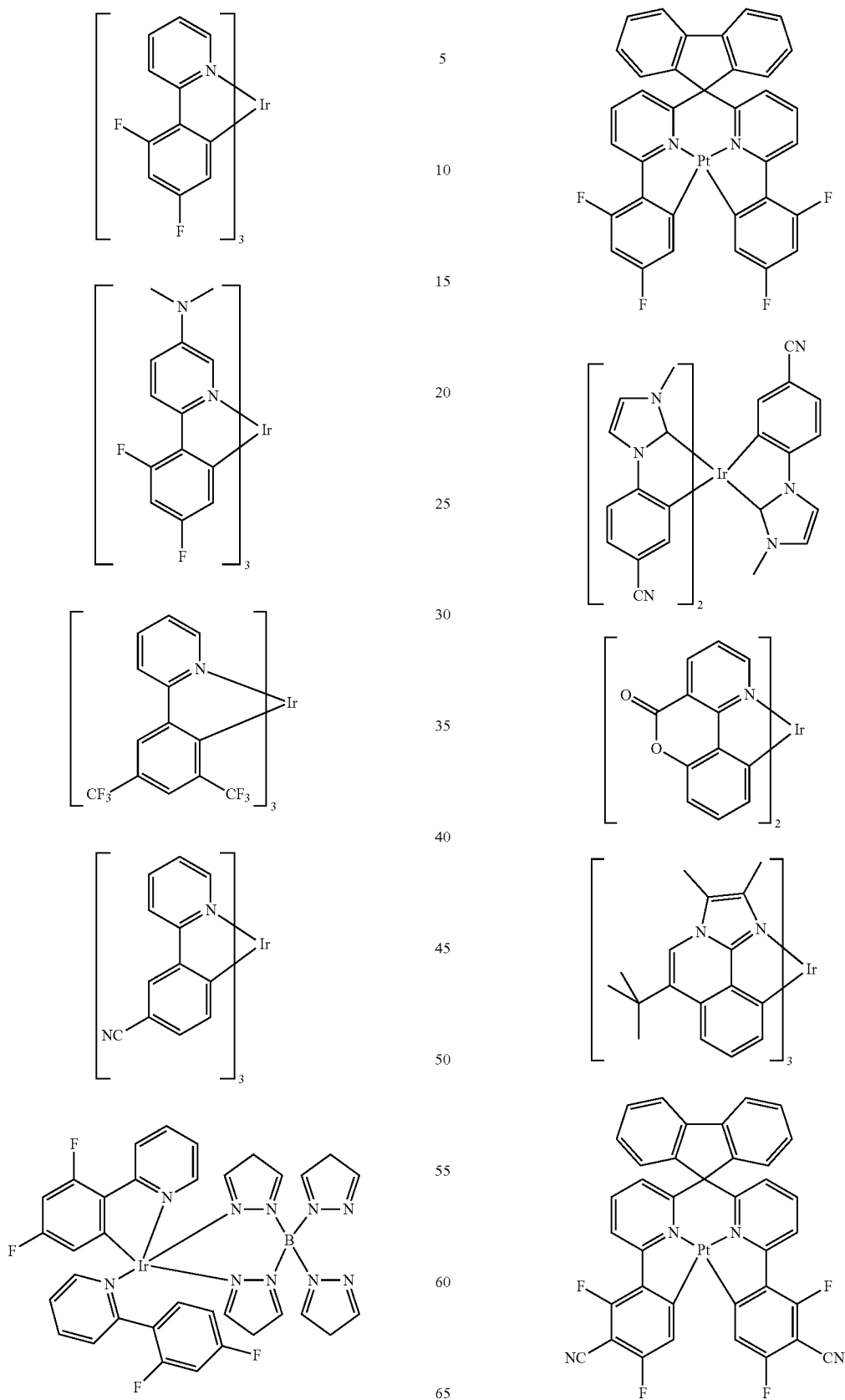

119
-continued
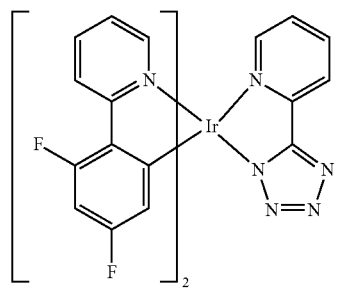
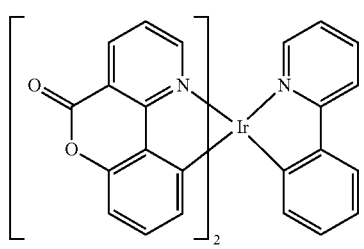
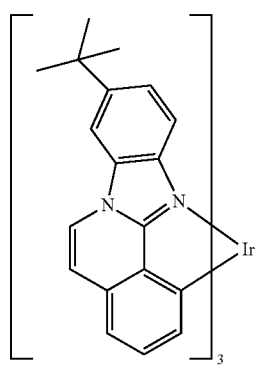
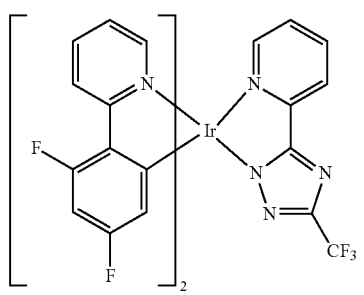
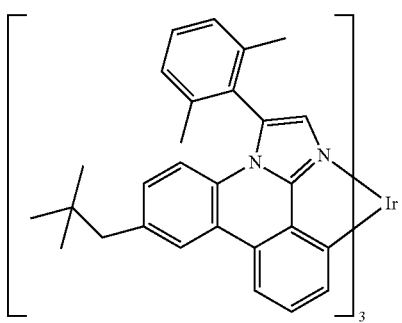
120
-continued
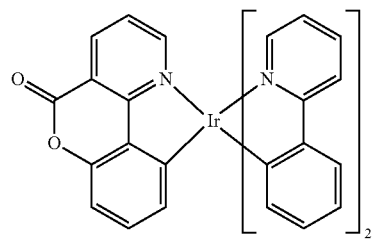
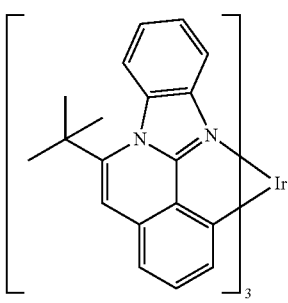
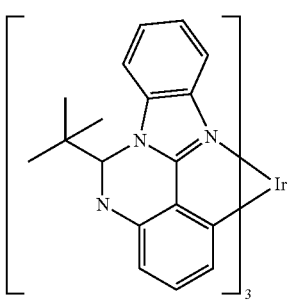
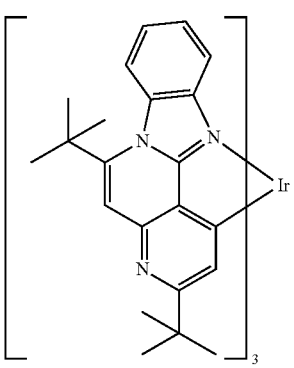
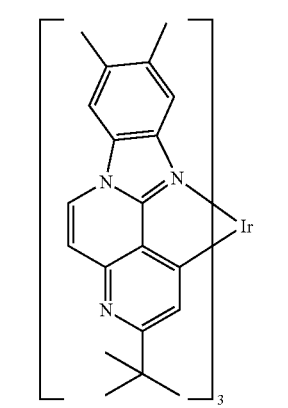

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and the as yet unpublished EP 12004426.8. Preference is likewise given to the benzoindenofluorenamines disclosed in the as yet unpublished EP 12006239.3 and the benzofluorenamines disclosed in the as yet unpublished EP 13000012.8.

Suitable matrix materials, preferably for fluorescent emitters, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is furthermore given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and also the pyrene compounds disclosed in EP 1749809, EP 1905754 and US 2012/0187826.

Preferred matrix materials for phosphorescent emitters, besides the compounds according to the invention, are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Suitable materials are, for example, the materials shown in the following table. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001). In particular, the compounds according to the invention can be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

Furthermore, the compounds of the formula (I) can be selected so that they can be fixed in a layer applied from solution, for example by crosslinking to give a polymer network. The polymer network is subsequently virtually or totally insoluble in the solvents commonly used in the case of application from solution. In this way, a plurality of layers can be applied from solution without the preceding layer being re-dissolved and mixing taking place during application of a subsequent layer from solution. A process of this type is disclosed in general terms, for example, in EP 0637899 and U.S. Pat. No. 6,107,452. In order that the compounds of the formula (I) are crosslinkable, they preferably contain at least one, preferably at least two crosslinkable groups. Crosslinkable group in the sense of the present application means a functional group which is capable of undergoing a reaction, preferably a polymerisation reaction, and thus forming an insoluble compound. The crosslinkable group is thus preferably a polymerisable group. As a result of the reaction of the crosslinkable group, a corresponding crosslinked compound and thus a sparingly soluble or insoluble layer is obtained. The crosslinking reaction can be supported, for example, by heat or by UV, microwave, X-ray or electron radiation, optionally in the presence of an initiator. Preferred crosslinkable groups are chemical groups containing terminal or cyclic alkenyl or terminal alkynyl groups, oxetanes, oxiranes or silanes. Particularly preferred crosslinkable groups are the crosslinkable groups disclosed in WO 2013/007348.

In accordance with the invention, the electronic devices comprising one or more compounds of the formula (I) can be employed in displays, as light sources in lighting applications and as light sources in medical and/or cosmetic applications (for example light therapy).

WORKING EXAMPLES

A) Synthesis Examples

The following syntheses are carried out, unless indicated otherwise, in dried solvents under a protective-gas atmosphere. The metal complexes are additionally handled with exclusion of light. The solvents and reagents can be purchased, for example, from Sigma-ALDRICH or ABCR. The numbers in square brackets for chemical compounds which are known from the literature refer to the CAS numbers.

Example 1:
9-(3'-Chlorobiphenyl-3-yl)-9H-carbazole

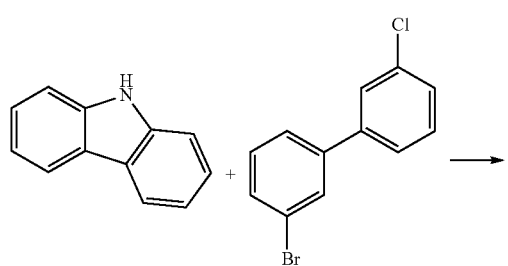

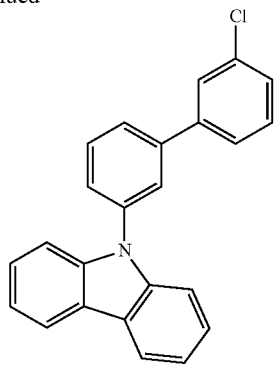

8.36 g (50 mmol) of carbazole and 14.72 g (55 mmol) of 3-bromo-3'-chloro-biphenyl are dissolved in toluene and degassed by passing in a protective gas. 4.90 ml (4.9 mmol, 1 M solution in toluene) of tri-tert-butylphosphine, 633.70 mg (2.82 mmol) of Pd(OAc)$_2$ and 10.21 g (105.87 mmol) of t-BuONa are subsequently added. The solids are degassed in advance, the reaction mixture is degassed afterwards and subsequently stirred under reflux for 12 h. The warm solution is filtered through aluminium oxide B (activity grade 1), washed with water, dried and evaporated. The residue is recrystallised from toluene. The yield is 15.92 g (45 mmol), corresponding to 90% of theory.

The following compounds can be obtained analogously:

| | Starting material 1 | Starting material 2 | Product | Yield |
|---|---|---|---|---|
| 1a | [103012-26-6] | [844856-42-4] | | 79% |
| 1b | [56525-79-2] | [844856-42-4] | | 85% |

-continued
| | Starting material 1 | Starting material 2 | Product | Yield |
|---|---|---|---|---|
| 1c | 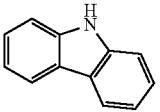<br>[86-74-8] | 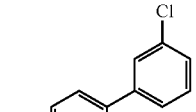<br>[91354-09-5] | 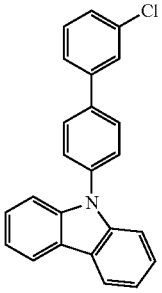 [SMILES: Clc1cccc(-c2ccc(-n3c4ccccc4c4ccccc43)cc2)c1] | 75% |
| 1d | 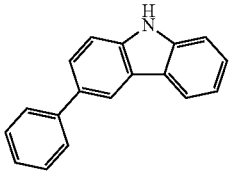<br>[103012-26-6] | 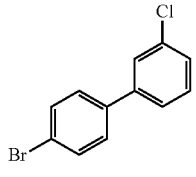<br>[91354-09-5] | 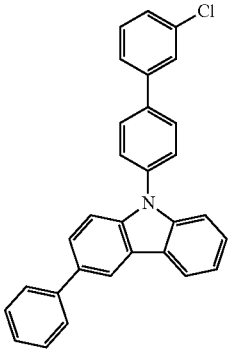 [SMILES: Clc1cccc(-c2ccc(-n3c4ccccc4c4cc(-c5ccccc5)ccc43)cc2)c1] | 71% |
| 1e | 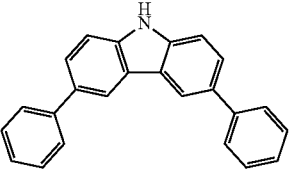<br>[56525-79-2] | 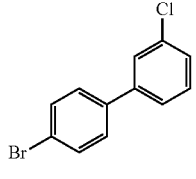<br>[91354-09-5] | 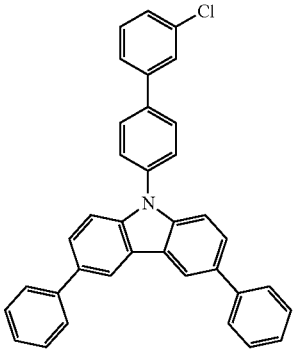 [SMILES: Clc1cccc(-c2ccc(-n3c4ccc(-c5ccccc5)cc4c4cc(-c5ccccc5)ccc43)cc2)c1] | 82% |
| 1f | 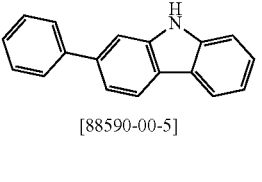 [SMILES: c1ccc(-c2ccc3c(c2)[nH]c2ccccc23)cc1]<br>[88590-00-5] | 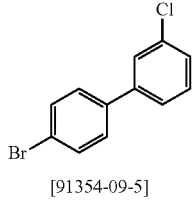 [SMILES: Clc1cccc(-c2ccc(Br)cc2)c1]<br>[91354-09-5] | 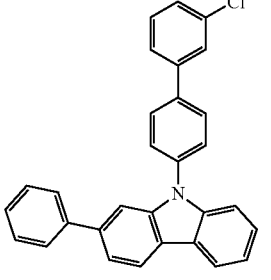 | 78% |
| 1g | 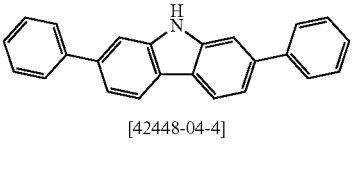 [SMILES: c1ccc(-c2ccc3c(c2)[nH]c2cc(-c4ccccc4)ccc23)cc1]<br>[42448-04-4] | 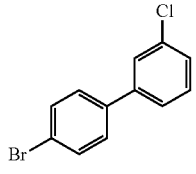<br>[91354-09-5] | 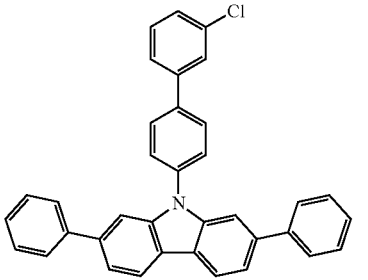 [SMILES: Clc1cccc(-c2ccc(-n3c4cc(-c5ccccc5)ccc4c4ccc(-c5ccccc5)cc43)cc2)c1] | 70% |

-continued
| | Starting material 1 | Starting material 2 | Product | Yield |
|---|---|---|---|---|
| 1h | 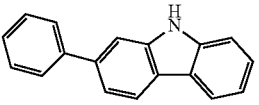 [88590-00-5] | 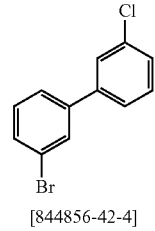 [SMILES: Clc1cccc(-c2cccc(Br)c2)c1] [844856-42-4] | 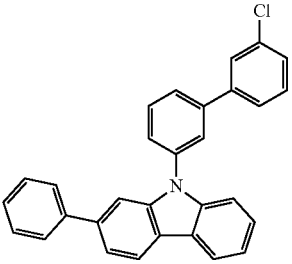 [SMILES: Clc1cccc(-c2cccc(-n3c4ccccc4c4ccc(-c5ccccc5)cc43)c2)c1] | 78% |
| 1i | 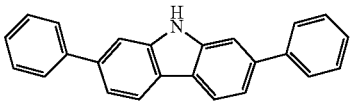 [42448-04-4] | 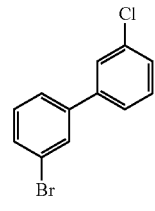 [844856-42-4] | 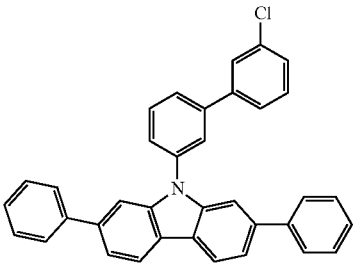 [SMILES: Clc1cccc(-c2cccc(-n3c4cc(-c5ccccc5)ccc4c4ccc(-c5ccccc5)cc43)c2)c1] | 83% |
| 1j | 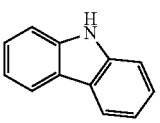 [86-74-8] | 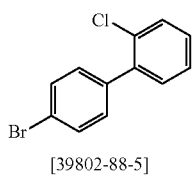 [SMILES: Clc1ccccc1-c1ccc(Br)cc1] [39802-88-5] | 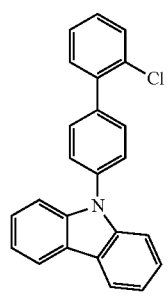 [SMILES: Clc1ccccc1-c1ccc(-n2c3ccccc3c3ccccc32)cc1] | 72% |
| 1k | 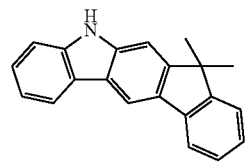 [1257220-47-5] | 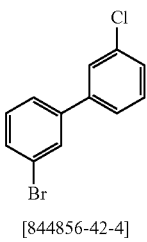 [SMILES: Clc1cccc(-c2cccc(Br)c2)c1] [844856-42-4] | 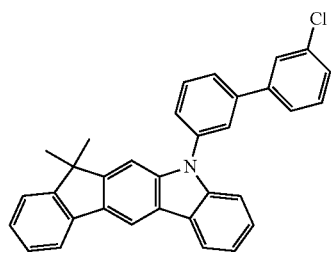 [SMILES: CC1(C)c2ccccc2-c2cc3c4ccccc4n(-c4cccc(-c5cccc(Cl)c5)c4)c3cc21] | 79% |

| | Starting material 1 | Starting material 2 | Product | Yield |
|---|---|---|---|---|
| 1l | [86-74-8] | [28320-32-3] | | 55% |
| 1m | [86-74-8] | [108-36-1] | | 65% |

Example 2: Bisbiphenyl-4-yl-(3-carbazol-9-yl-[1,1';3',1'']terphenyl-4''-yl)-amine

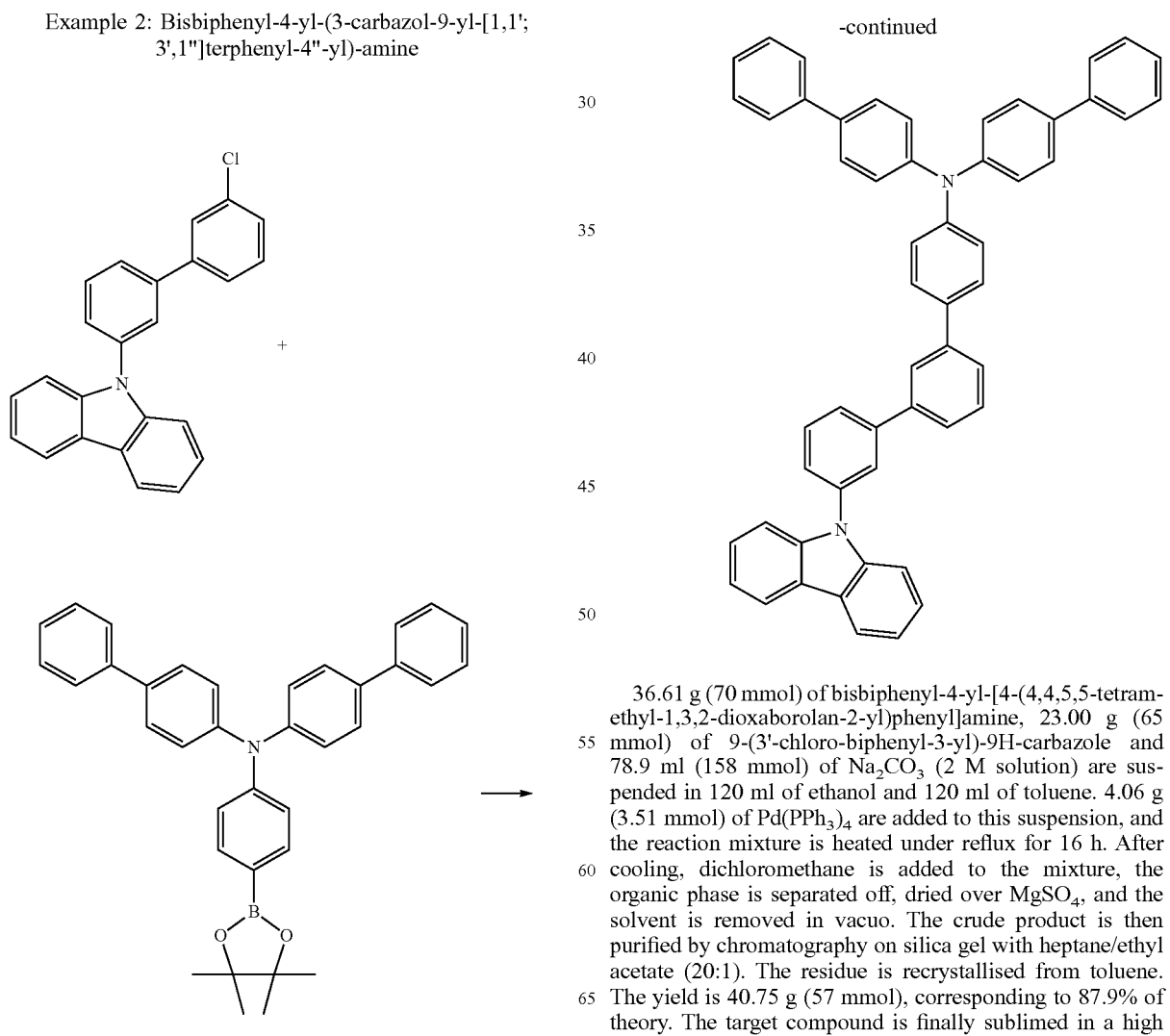

36.61 g (70 mmol) of bisbiphenyl-4-yl-[4-(4,4,5,5-tetramethyl-1,3,2-dioxaborolan-2-yl)phenyl]amine, 23.00 g (65 mmol) of 9-(3'-chloro-biphenyl-3-yl)-9H-carbazole and 78.9 ml (158 mmol) of $Na_2CO_3$ (2 M solution) are suspended in 120 ml of ethanol and 120 ml of toluene. 4.06 g (3.51 mmol) of $Pd(PPh_3)_4$ are added to this suspension, and the reaction mixture is heated under reflux for 16 h. After cooling, dichloromethane is added to the mixture, the organic phase is separated off, dried over $MgSO_4$, and the solvent is removed in vacuo. The crude product is then purified by chromatography on silica gel with heptane/ethyl acetate (20:1). The residue is recrystallised from toluene. The yield is 40.75 g (57 mmol), corresponding to 87.9% of theory. The target compound is finally sublimed in a high vacuum ($p=5\times10^6$ mbar). The purity is 99.9%.

The following compounds can be obtained analogously:
| Starting material 1 | Starting material 2 |
|---|---|
| 2a 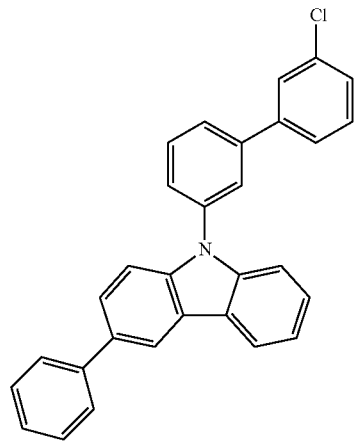 [SMILES: Clc1cccc(-c2cccc(-n3c4ccccc4c4cc(-c5ccccc5)ccc43)c2)c1] | 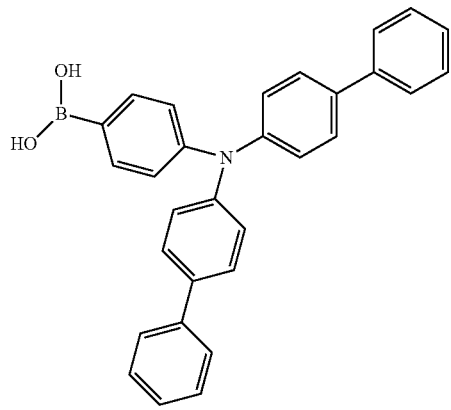 [943836-24-6] |
| 2b 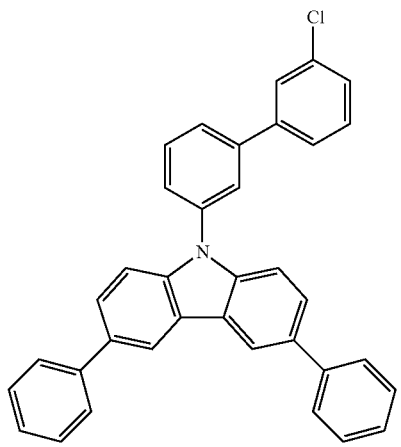 [SMILES: Clc1cccc(-c2cccc(-n3c4ccc(-c5ccccc5)cc4c4cc(-c5ccccc5)ccc43)c2)c1] | 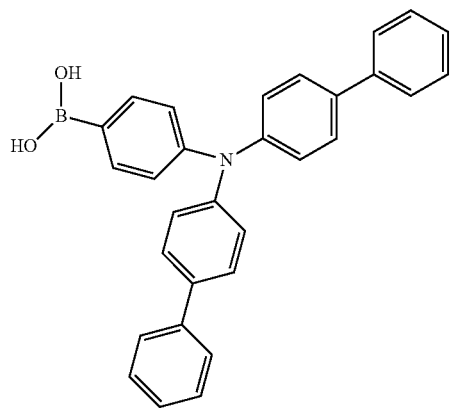 [943836-24-6] |
| 2c 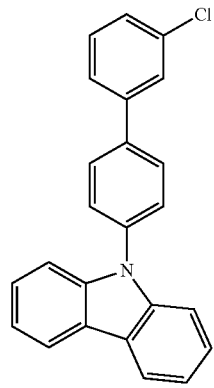 [SMILES: Clc1cccc(-c2ccc(-n3c4ccccc4c4ccccc43)cc2)c1] | 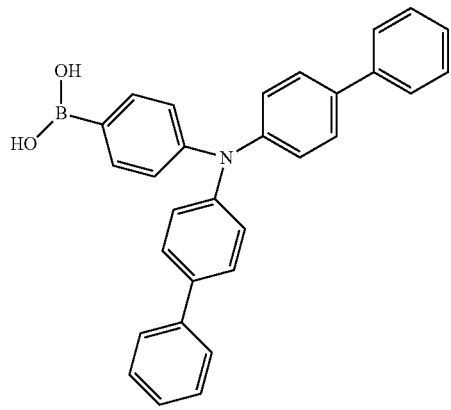 [943836-24-6] |

| | | |
|---|---|---|
| 2d | 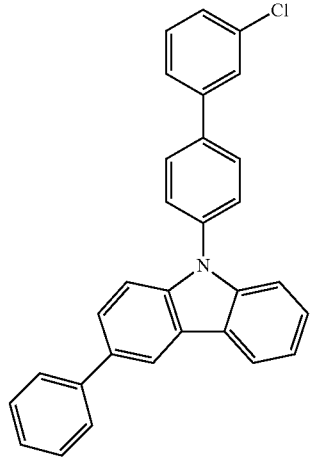 [SMILES: Clc1cccc(-c2ccc(-n3c4ccccc4c4cc(-c5ccccc5)ccc43)cc2)c1] | 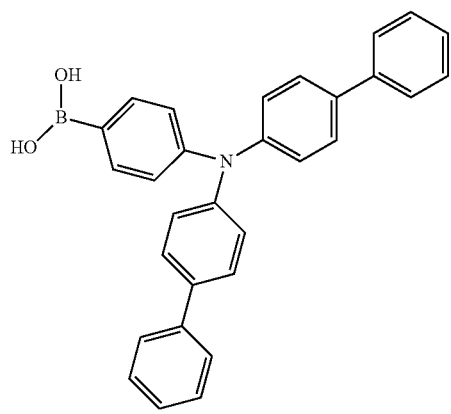<br>[943836-24-6] |
| 2e | 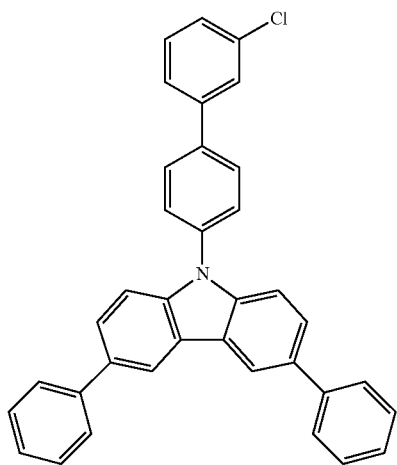 [SMILES: Clc1cccc(-c2ccc(-n3c4ccc(-c5ccccc5)cc4c4cc(-c5ccccc5)ccc43)cc2)c1] | 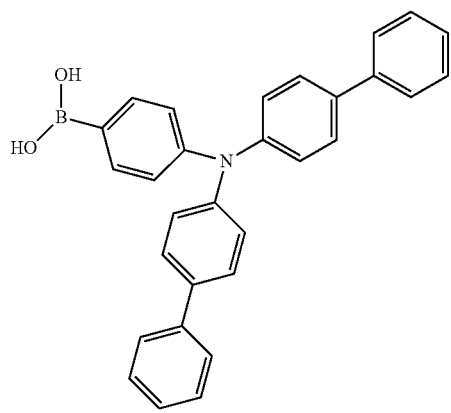<br>[943836-24-6] |
| 2f | 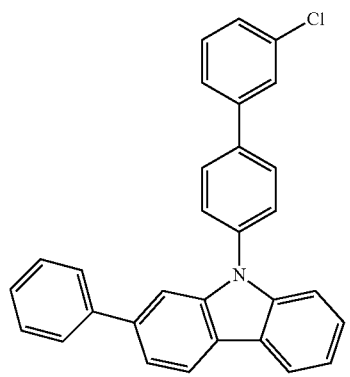 [SMILES: Clc1cccc(-c2ccc(-n3c4ccccc4c4ccc(-c5ccccc5)cc43)cc2)c1] | 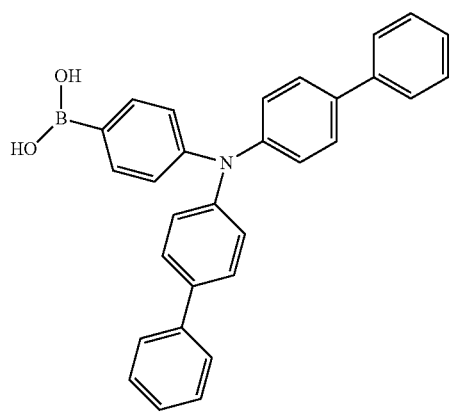<br>[943836-24-6] |

-continued
2g
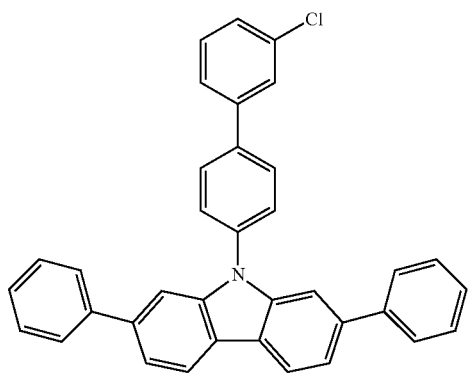 [SMILES: Clc1cccc(-c2ccc(-n3c4cc(-c5ccccc5)ccc4c4ccc(-c5ccccc5)cc43)cc2)c1]
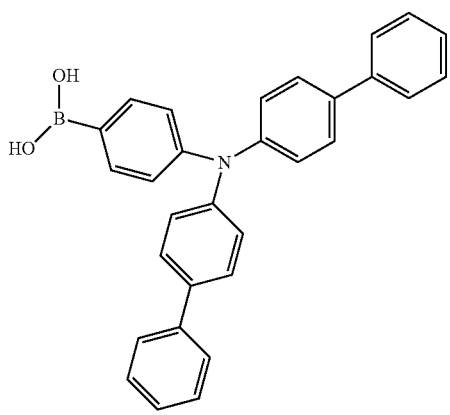
[943836-24-6]
2h
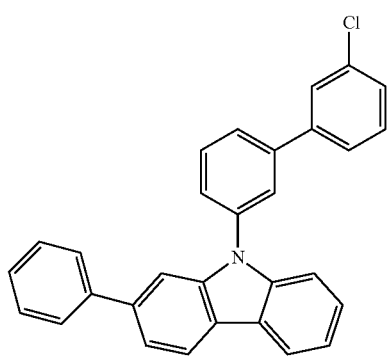 [SMILES: Clc1cccc(-c2cccc(-n3c4ccccc4c4ccc(-c5ccccc5)cc43)c2)c1]
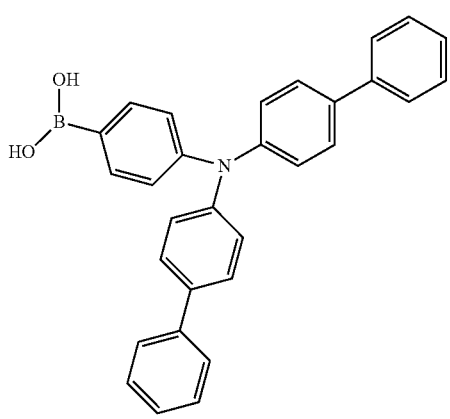
[943836-24-6]
2i
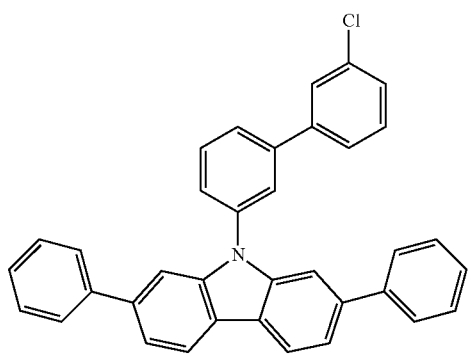 [SMILES: Clc1cccc(-c2cccc(-n3c4cc(-c5ccccc5)ccc4c4ccc(-c5ccccc5)cc43)c2)c1]
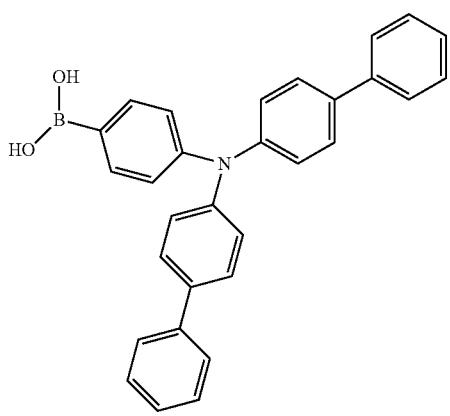
[943836-24-6]

-continued
2k 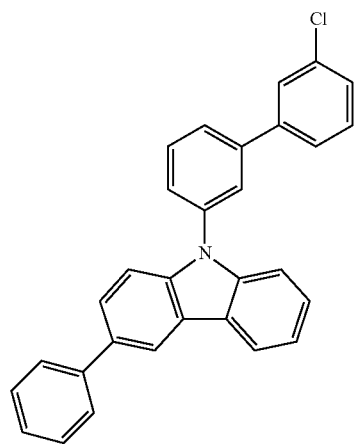 [SMILES: Clc1cccc(-c2cccc(-n3c4ccccc4c4cc(-c5ccccc5)ccc43)c2)c1] 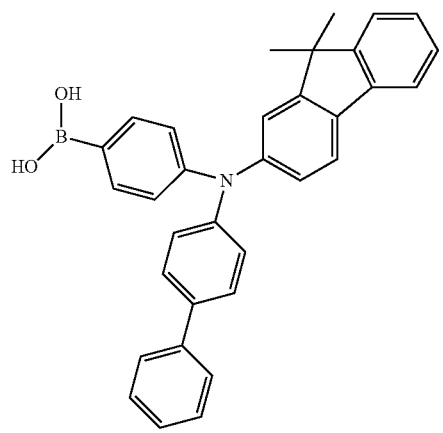
[1265177-27-4]
2l 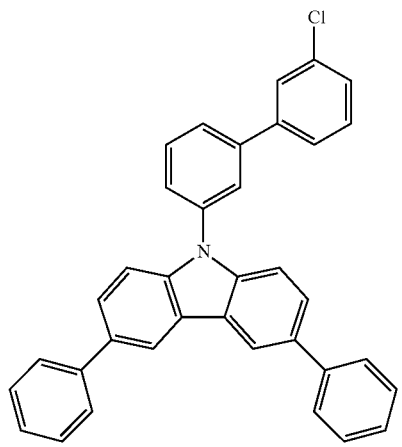 [SMILES: Clc1cccc(-c2cccc(-n3c4ccc(-c5ccccc5)cc4c4cc(-c5ccccc5)ccc43)c2)c1] 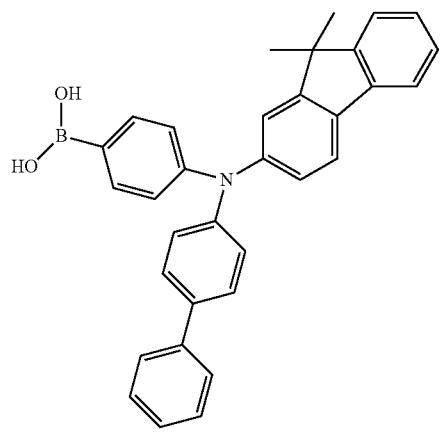
[1265177-27-4]
2m 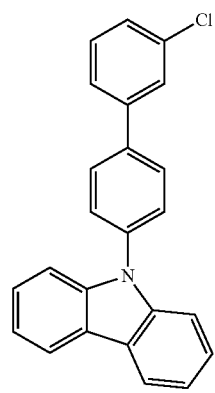 [SMILES: Clc1cccc(-c2ccc(-n3c4ccccc4c4ccccc43)cc2)c1] 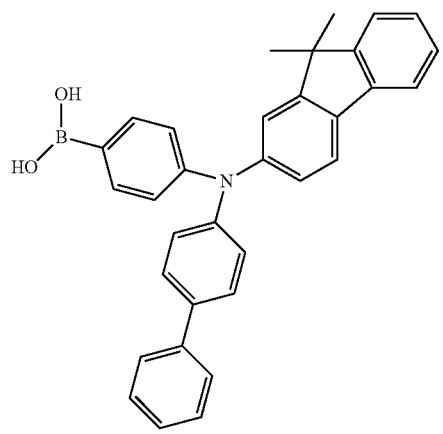
[1265177-27-4]

| | | |
|---|---|---|
| 2n | 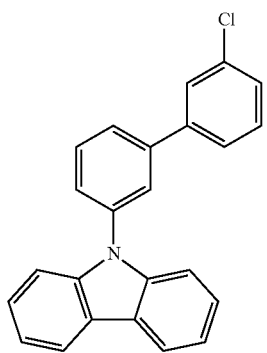 [SMILES: Clc1cccc(-c2cccc(-n3c4ccccc4c4ccccc43)c2)c1] | 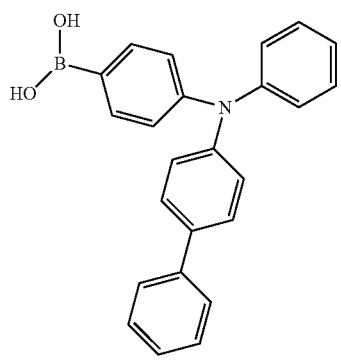 [SMILES: OB(O)c1ccc(N(c2ccccc2)c2ccc(-c3ccccc3)cc2)cc1] |
| 2o | 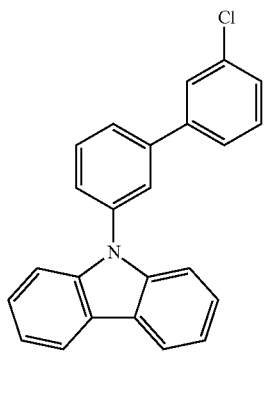 [SMILES: Clc1cccc(-c2cccc(-n3c4ccccc4c4ccccc43)c2)c1] | 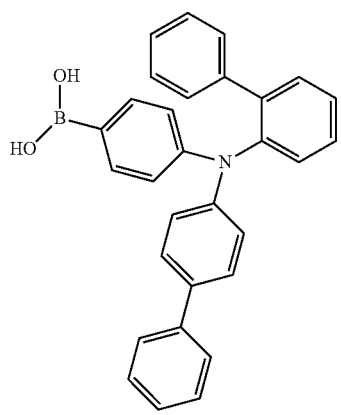 [SMILES: OB(O)c1ccc(N(c2ccc(-c3ccccc3)cc2)c2ccccc2-c2ccccc2)cc1] |
| 2p | 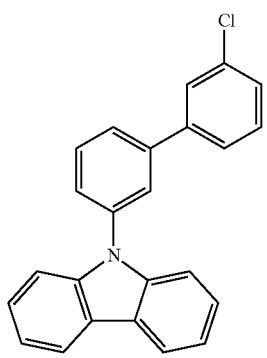 [SMILES: Clc1cccc(-c2cccc(-n3c4ccccc4c4ccccc43)c2)c1] | 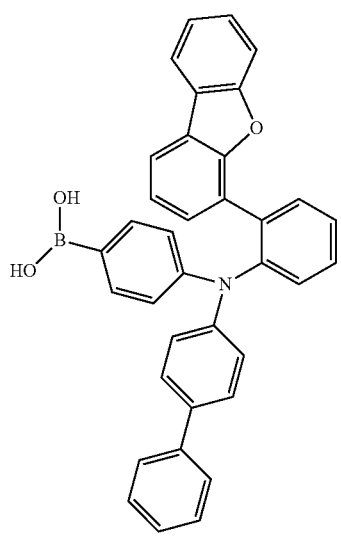 [SMILES: OB(O)c1ccc(N(c2ccc(-c3ccccc3)cc2)c2ccccc2-c2cccc3c2oc2ccccc23)cc1] |

-continued
2r
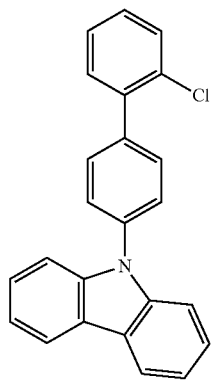 [SMILES: Clc1ccccc1-c1ccc(-n2c3ccccc3c3ccccc32)cc1]
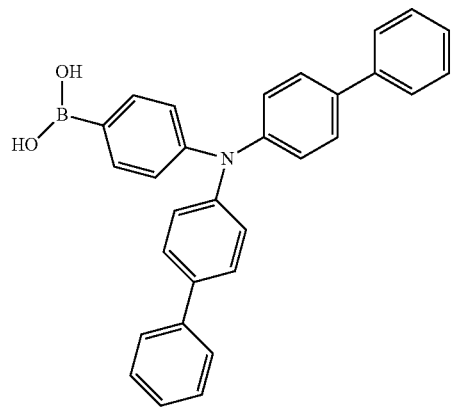
[943836-24-6]
2m
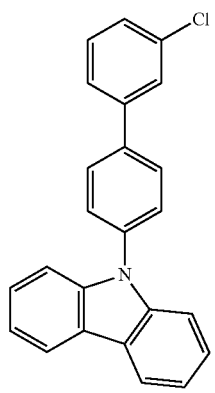 [SMILES: Clc1cccc(-c2ccc(-n3c4ccccc4c4ccccc43)cc2)c1]
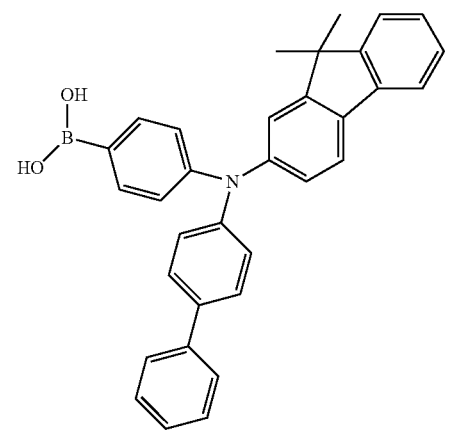
[1265177-27-4]
2s
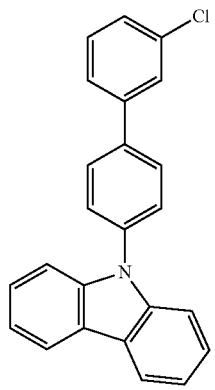 [SMILES: Clc1cccc(-c2ccc(-n3c4ccccc4c4ccccc43)cc2)c1]
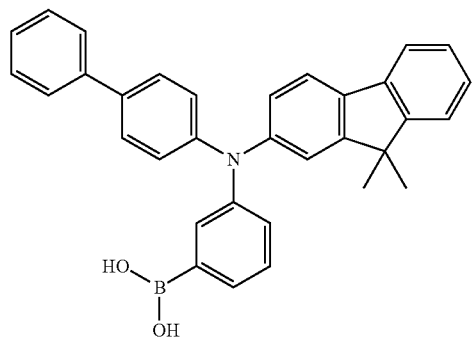 [SMILES: CC1(C)c2ccccc2-c2ccc(N(c3ccc(-c4ccccc4)cc3)c3cccc(B(O)O)c3)cc21]

2t
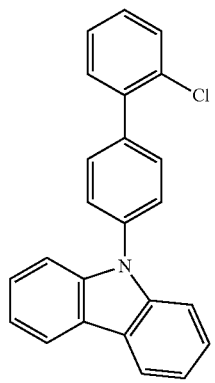 [SMILES: Clc1ccccc1-c1ccc(-n2c3ccccc3c3ccccc32)cc1]
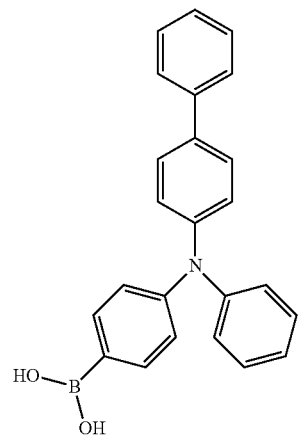
[1084334-86-0]
2u
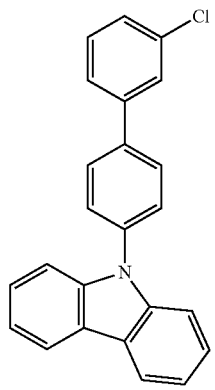 [SMILES: Clc1cccc(-c2ccc(-n3c4ccccc4c4ccccc43)cc2)c1]
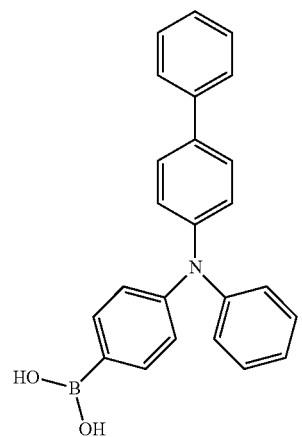
[1084334-86-0]
2v
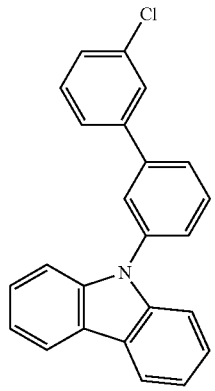 [SMILES: Clc1cccc(-c2cccc(-n3c4ccccc4c4ccccc43)c2)c1]
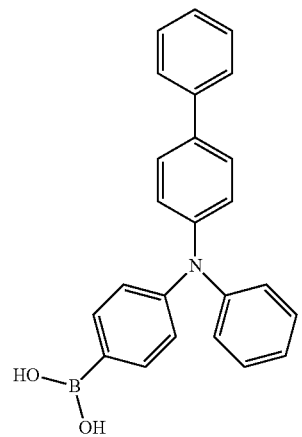
[1084334-86-0]

-continued
2w 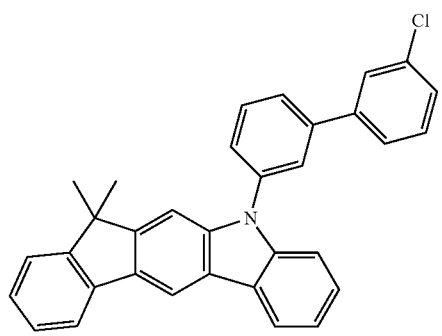 [SMILES: CC1(C)c2ccccc2-c2cc3c4ccccc4n(-c4cccc(-c5cccc(Cl)c5)c4)c3cc21] 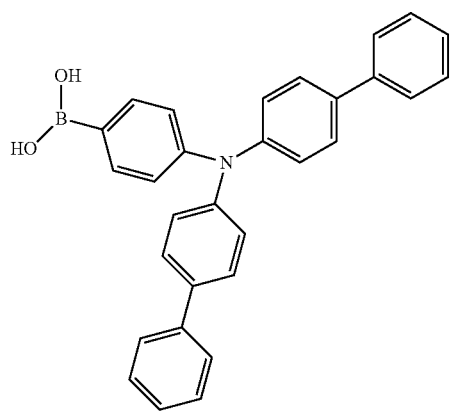
[943836-24-6]
2y 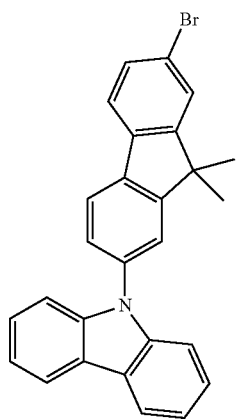 [SMILES: CC1(C)c2cc(Br)ccc2-c2ccc(-n3c4ccccc4c4ccccc43)cc21] 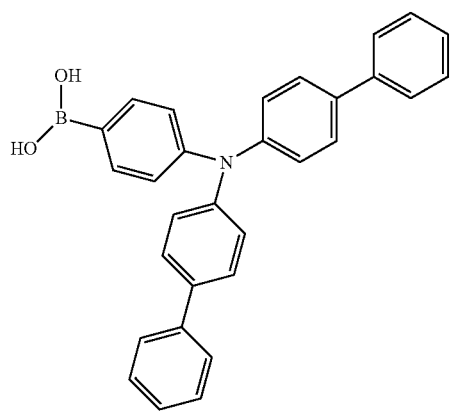
[943836-24-6]
2z 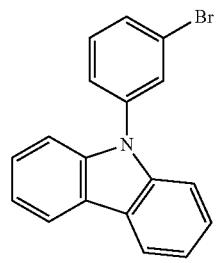 [SMILES: Brc1cccc(-n2c3ccccc3c3ccccc32)c1] 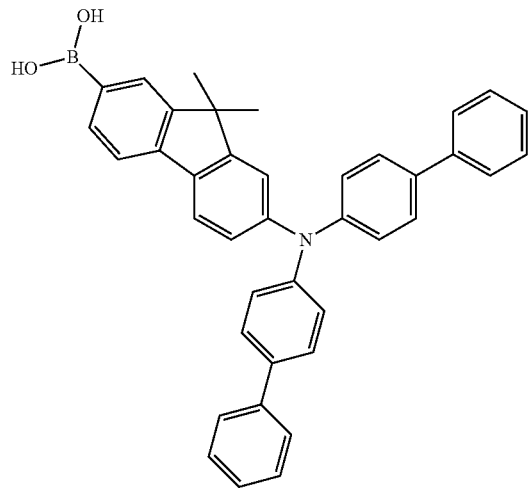 [SMILES: CC1(C)c2cc(B(O)O)ccc2-c2ccc(N(c3ccc(-c4ccccc4)cc3)c3ccc(-c4ccccc4)cc3)cc21]

-continued

| | Product | Yield |
|---|---|---|
| 2a | | 79% |
| 2b | | 85% |

| | | |
|---|---|---|
| 2c | 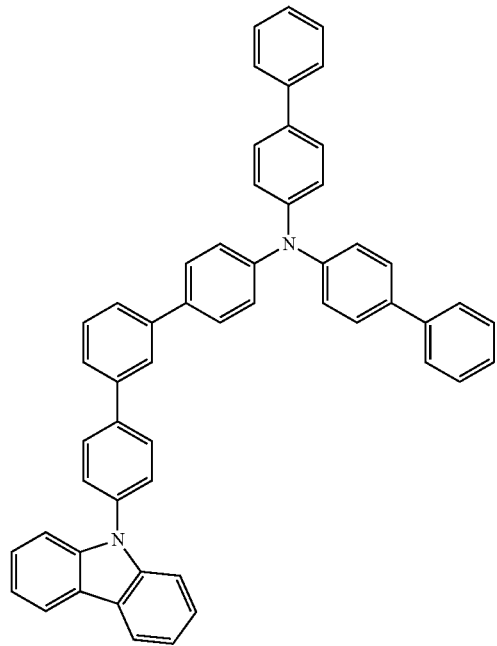 [SMILES: c1ccc(-c2ccc(N(c3ccc(-c4ccccc4)cc3)c3ccc(-c4cccc(-c5ccc(-n6c7ccccc7c7ccccc76)cc5)c4)cc3)cc2)cc1] | 75% |
| 2d | 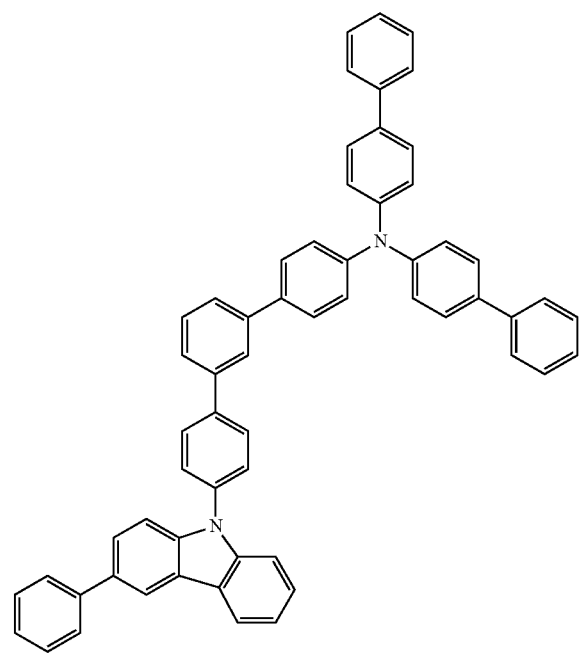 [SMILES: c1ccc(-c2ccc(N(c3ccc(-c4ccccc4)cc3)c3ccc(-c4cccc(-c5ccc(-n6c7ccccc7c7cc(-c8ccccc8)ccc76)cc5)c4)cc3)cc2)cc1] | 71% |

| | | |
|---|---|---|
| 2e | 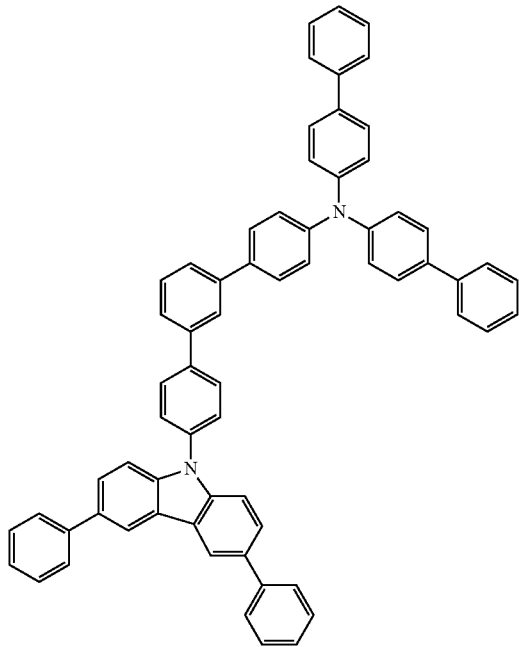 [SMILES: c1ccc(-c2ccc(N(c3ccc(-c4ccccc4)cc3)c3ccc(-c4cccc(-c5ccc(-n6c7ccc(-c8ccccc8)cc7c7cc(-c8ccccc8)ccc76)cc5)c4)cc3)cc2)cc1] | 82% |
| 2f | 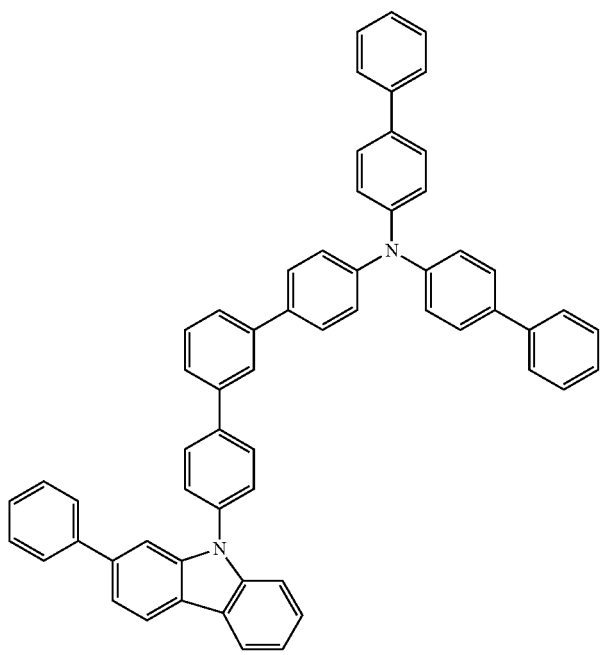 [SMILES: c1ccc(-c2ccc(N(c3ccc(-c4ccccc4)cc3)c3ccc(-c4cccc(-c5ccc(-n6c7ccccc7c7ccc(-c8ccccc8)cc76)cc5)c4)cc3)cc2)cc1] | 78% |

2g 70%
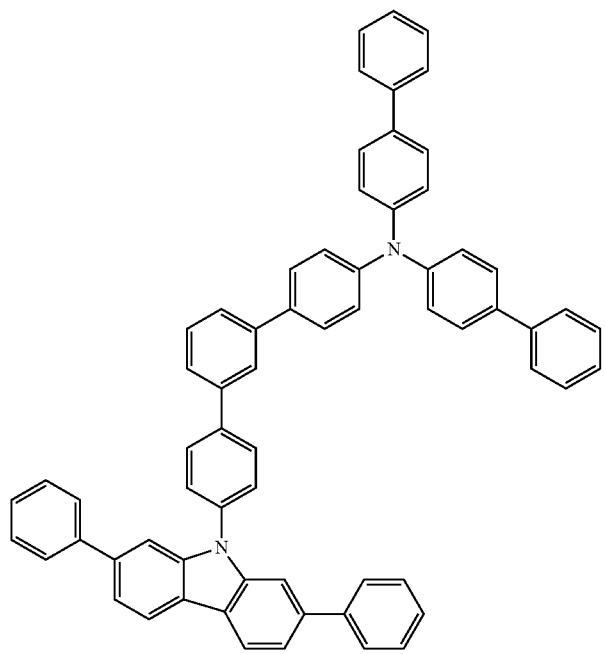 [SMILES: c1ccc(-c2ccc(N(c3ccc(-c4ccccc4)cc3)c3ccc(-c4cccc(-c5ccc(-n6c7cc(-c8ccccc8)ccc7c7ccc(-c8ccccc8)cc76)cc5)c4)cc3)cc2)cc1]
2h 78%
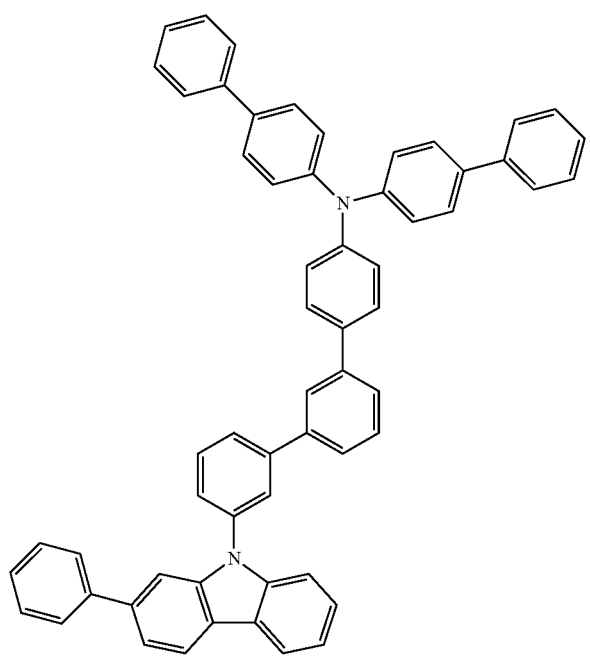 [SMILES: c1ccc(-c2ccc(N(c3ccc(-c4ccccc4)cc3)c3ccc(-c4cccc(-c5cccc(-n6c7ccccc7c7ccc(-c8ccccc8)cc76)c5)c4)cc3)cc2)cc1]

-continued
| 2i | 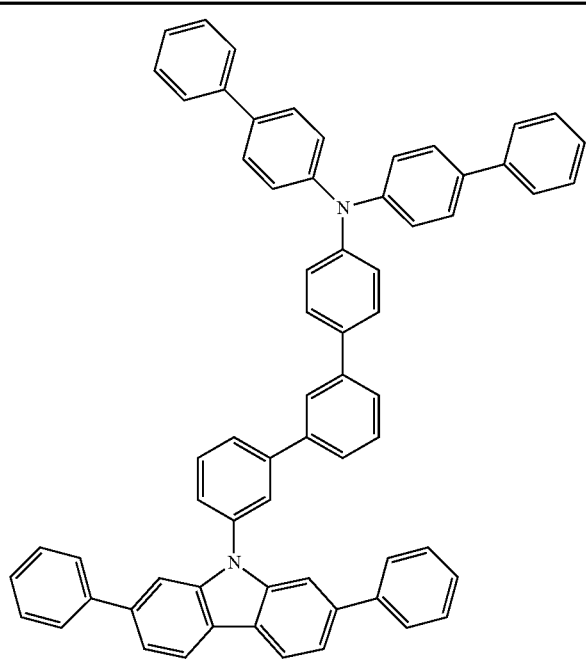 | 83% |
| 2k | 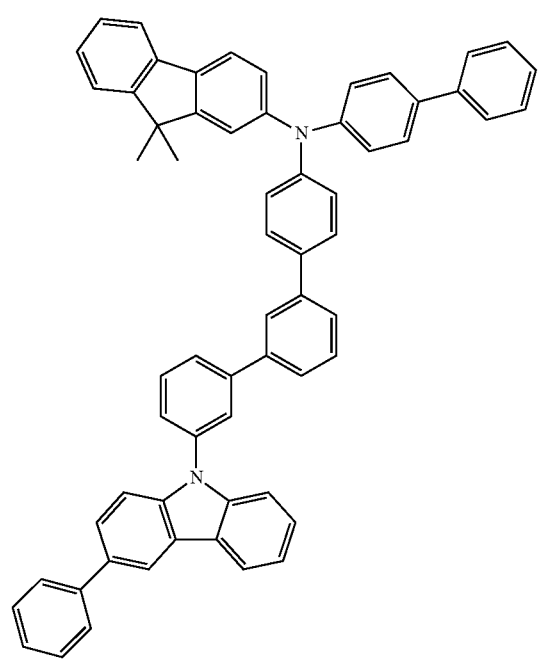 [SMILES: CC1(C)c2ccccc2-c2ccc(N(c3ccc(-c4ccccc4)cc3)c3ccc(-c4cccc(-c5cccc(-n6c7ccccc7c7cc(-c8ccccc8)ccc76)c5)c4)cc3)cc21] | 79% |

| | | |
|---|---|---|
| 2l | 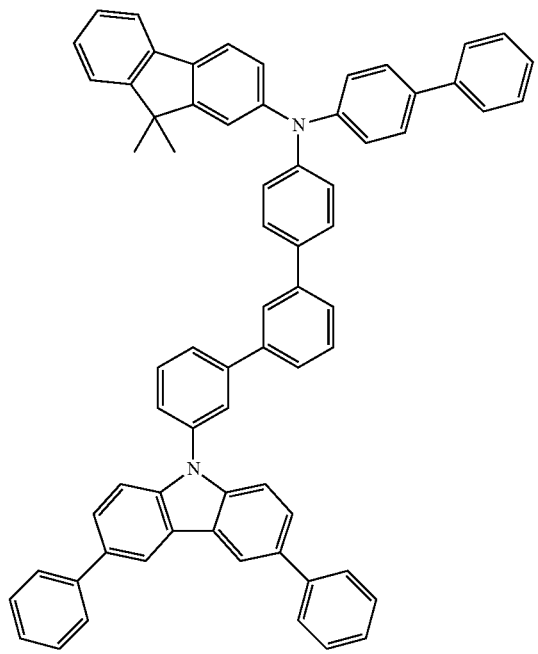 [SMILES: CC1(C)c2ccccc2-c2ccc(N(c3ccc(-c4ccccc4)cc3)c3ccc(-c4cccc(-c5cccc(-n6c7ccc(-c8ccccc8)cc7c7cc(-c8ccccc8)ccc76)c5)c4)cc3)cc21] | 85% |
| 2m | 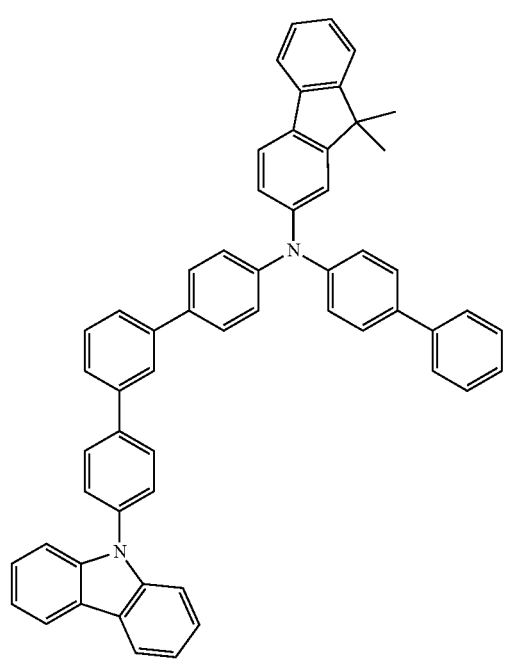 [SMILES: CC1(C)c2ccccc2-c2ccc(N(c3ccc(-c4ccccc4)cc3)c3ccc(-c4cccc(-c5ccc(-n6c7ccccc7c7ccccc76)cc5)c4)cc3)cc21] | 75% |

-continued
| | | |
|---|---|---|
| 2n | 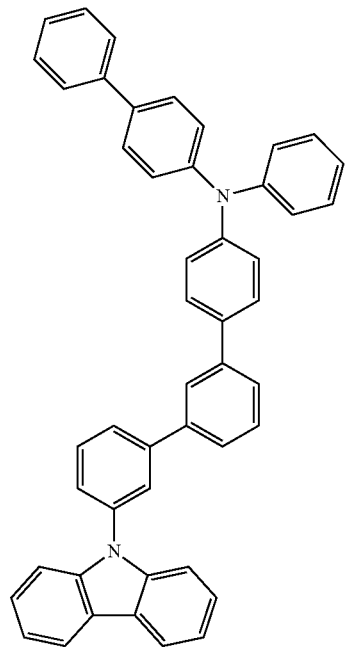 [SMILES: c1ccc(-c2ccc(N(c3ccccc3)c3ccc(-c4cccc(-c5cccc(-n6c7ccccc7c7ccccc76)c5)c4)cc3)cc2)cc1] | 79% |
| 2o | 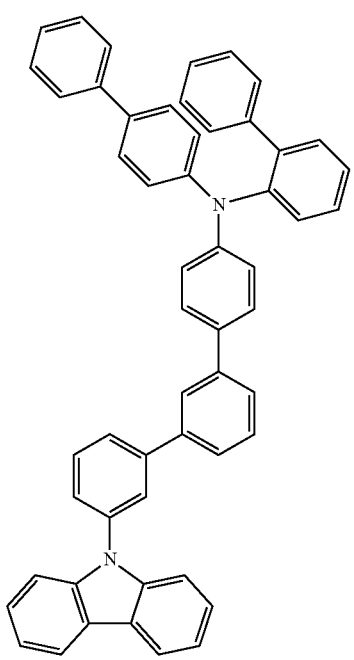 [SMILES: c1ccc(-c2ccc(N(c3ccc(-c4cccc(-c5cccc(-n6c7ccccc7c7ccccc76)c5)c4)cc3)c3ccccc3-c3ccccc3)cc2)cc1] | 82% |

2p 74%
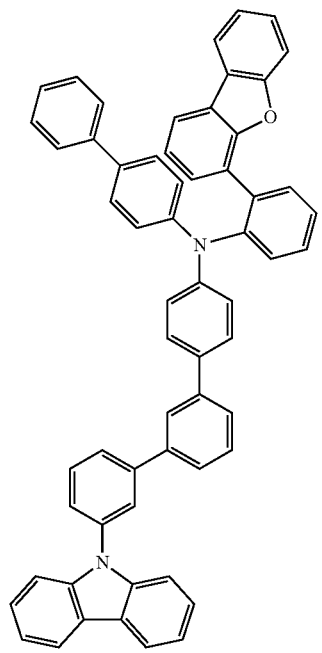 [SMILES: c1ccc(-c2ccc(N(c3ccc(-c4cccc(-c5cccc(-n6c7ccccc7c7ccccc76)c5)c4)cc3)c3ccccc3-c3cccc4c3oc3ccccc34)cc2)cc1]
2r 70%
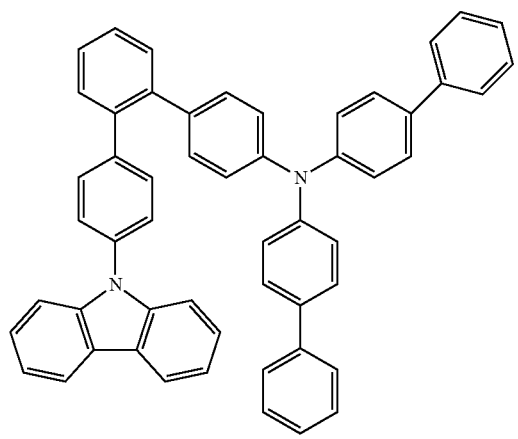 [SMILES: c1ccc(-c2ccc(N(c3ccc(-c4ccccc4)cc3)c3ccc(-c4ccccc4-c4ccc(-n5c6ccccc6c6ccccc65)cc4)cc3)cc2)cc1]

2m 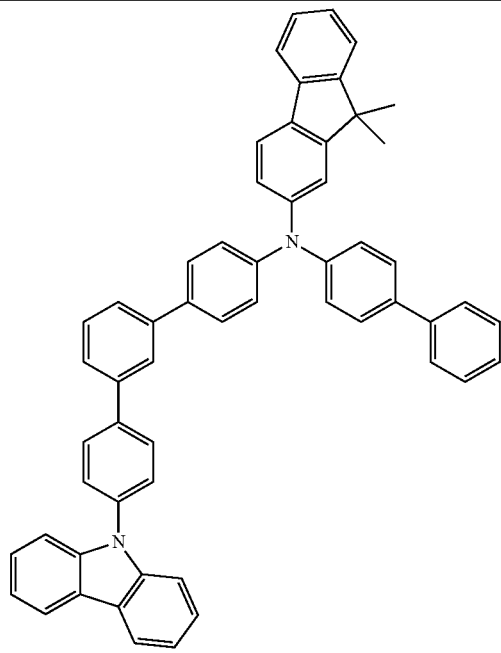 75%
2s 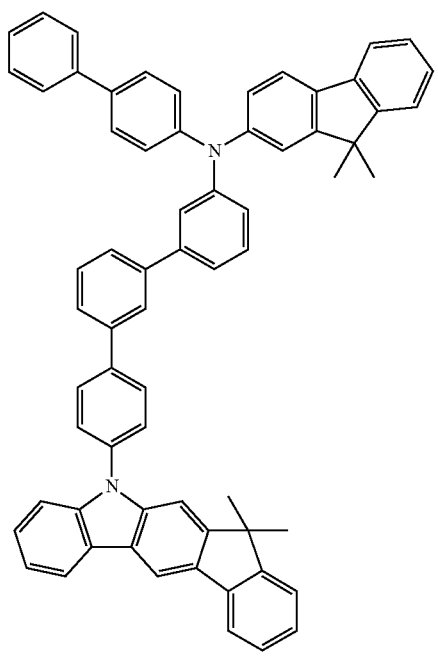 [SMILES: CC1(C)c2ccccc2-c2ccc(N(c3ccc(-c4ccccc4)cc3)c3cccc(-c4cccc(-c5ccc(-n6c7ccccc7c7cc8c(cc76)C(C)(C)c6ccccc6-8)cc5)c4)c3)cc21] 68%
2t 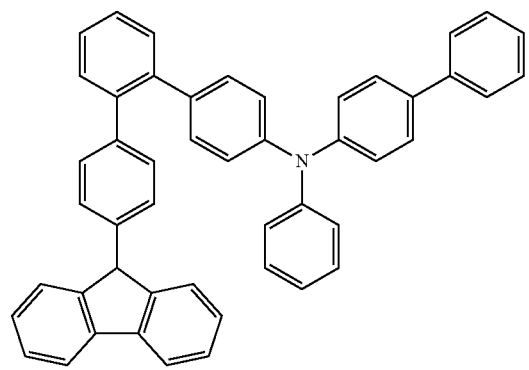 [SMILES: c1ccc(-c2ccc(N(c3ccccc3)c3ccc(-c4ccccc4-c4ccc(C5c6ccccc6-c6ccccc65)cc4)cc3)cc2)cc1] 61%

2u 74%
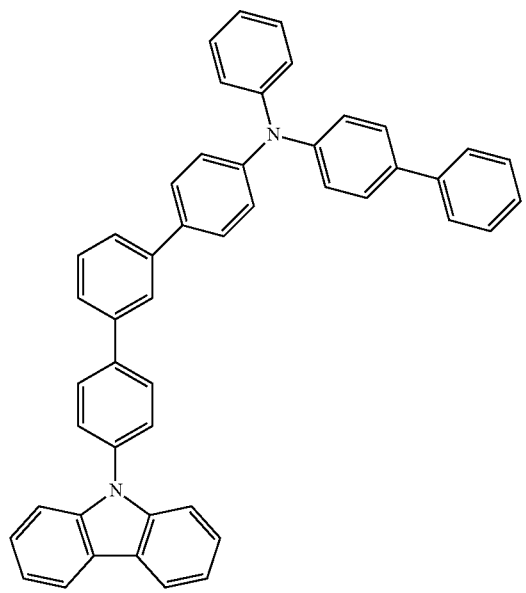 [SMILES: c1ccc(-c2ccc(N(c3ccccc3)c3ccc(-c4cccc(-c5ccc(-n6c7ccccc7c7ccccc76)cc5)c4)cc3)cc2)cc1]
2v 75%
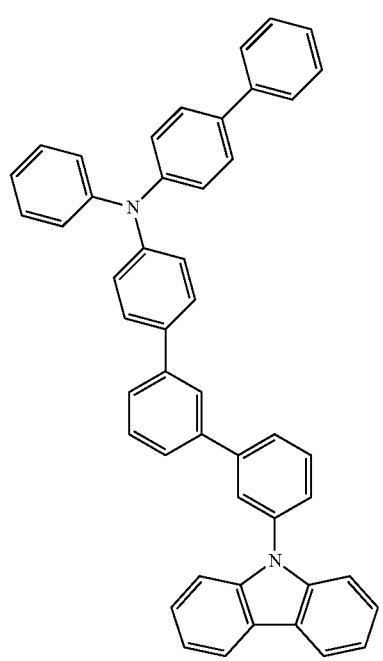 [SMILES: c1ccc(-c2ccc(N(c3ccccc3)c3ccc(-c4cccc(-c5cccc(-n6c7ccccc7c7ccccc76)c5)c4)cc3)cc2)cc1]

2w 68%
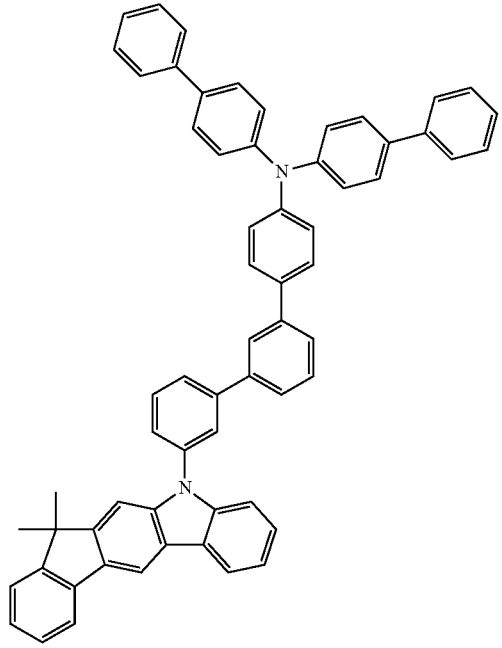 [SMILES: CC1(C)c2ccccc2-c2cc3c4ccccc4n(-c4cccc(-c5cccc(-c6ccc(N(c7ccc(-c8ccccc8)cc7)c7ccc(-c8ccccc8)cc7)cc6)c5)c4)c3cc21]
2y 68%
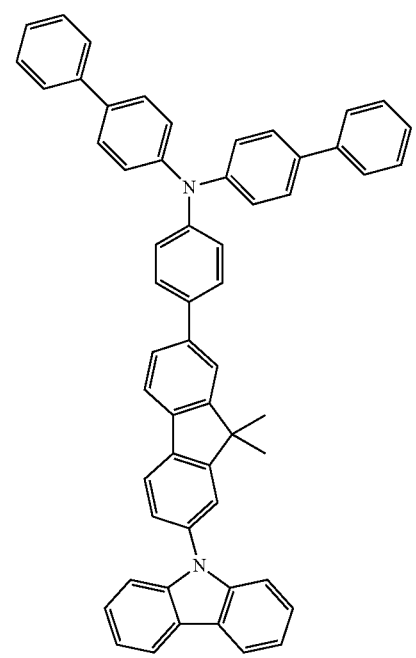 [SMILES: CC1(C)c2cc(-c3ccc(N(c4ccc(-c5ccccc5)cc4)c4ccc(-c5ccccc5)cc4)cc3)ccc2-c2ccc(-n3c4ccccc4c4ccccc43)cc21]

2z 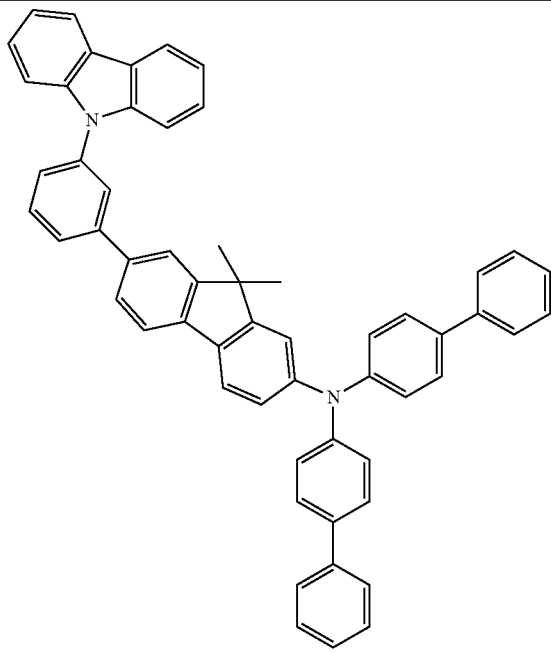 70

B) Device Examples

OLEDs according to the invention and OLEDs in accordance with the prior art are produced by a general process in accordance with WO 04/058911, which is adapted to the circumstances described here (layer-thickness variation, materials).

The data of various OLEDs are presented in the following Examples E1 to E9 according to the application and in Reference Examples V1-V6. The substrates used are glass plates coated with structured ITO (indium tin oxide) in a thickness of 50 nm. The OLEDs have in principle the following layer structure: substrate/p-doped hole-transport layer (HTL1)/hole-transport layer (HTL2)/p-doped hole-transport layer (HTL3)/hole-transport layer (HTL4)/emission layer (EML)/electron-transport layer (ETL)/electron-injection layer (EIL) and finally a cathode. The cathode is formed by an aluminium layer with a thickness of 100 nm. The materials required for the production of the OLEDs are shown in Table 1, the precise structures of the devices produced are shown in Table 2.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (95%:5%) here means that material H1 is present in the layer in a proportion by volume of 95% and SEB1 is present in the layer in a proportion of 5%. Analogously, the electron-transport layers or the hole-transport layers may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE @ 10 mA/cm$^2$ denotes the external quantum efficiency at a current density of 10 mA/cm$^2$. LT80 @ 50 mA/cm$^2$ is the lifetime until the OLED has dropped to 80% of the initial intensity at an initial luminance at constant current of 50 mA/cm$^2$.

TABLE 1

Structures of the materials used

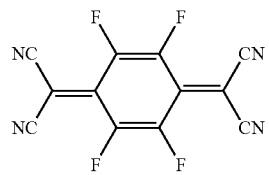 [SMILES: N#CC(C#N)=c1c(F)c(F)c(=C(C#N)C#N)c(F)c1F]

F4TCNQ

TABLE 1-continued
Structures of the materials used
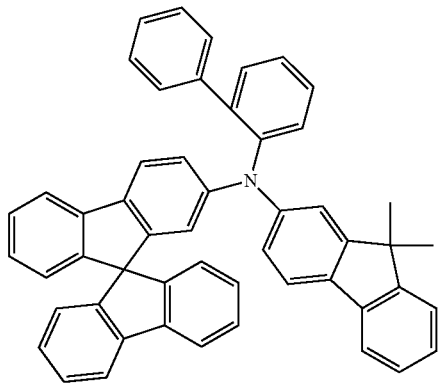 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HIL
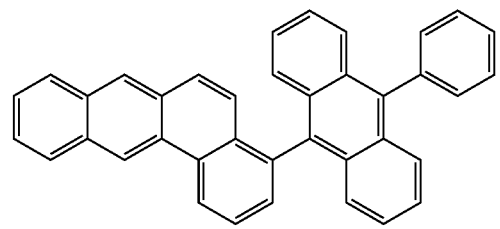 [SMILES: c1ccc(-c2c3ccccc3c(-c3cccc4c3ccc3cc5ccccc5cc34)c3ccccc23)cc1]
H1
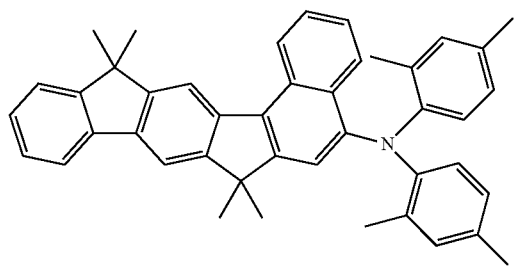 [SMILES: Cc1ccc(N(c2ccc(C)cc2C)c2cc3c(c4ccccc24)-c2cc4c(cc2C3(C)C)-c2ccccc2C4(C)C)c(C)c1]
SEB
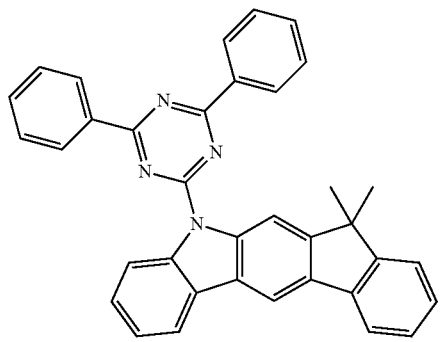 [SMILES: CC1(C)c2ccccc2-c2cc3c4ccccc4n(-c4nc(-c5ccccc5)nc(-c5ccccc5)n4)c3cc21]
H2

TABLE 1-continued
Structures of the materials used
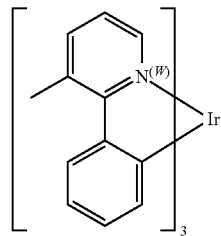
TEG
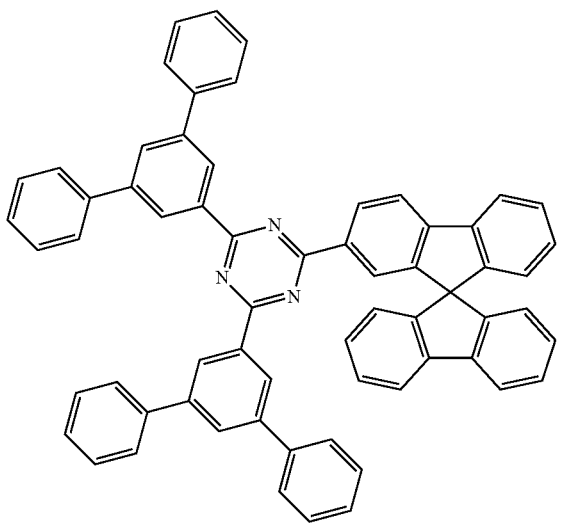 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM
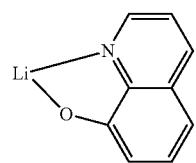
LiQ
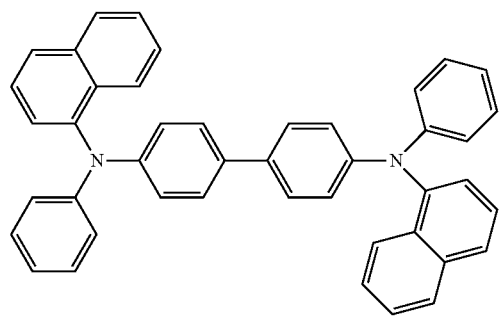 [SMILES: c1ccc(N(c2ccc(-c3ccc(N(c4ccccc4)c4cccc5ccccc45)cc3)cc2)c2cccc3ccccc23)cc1]
NPB TABLE 1-continued
Structures of the materials used
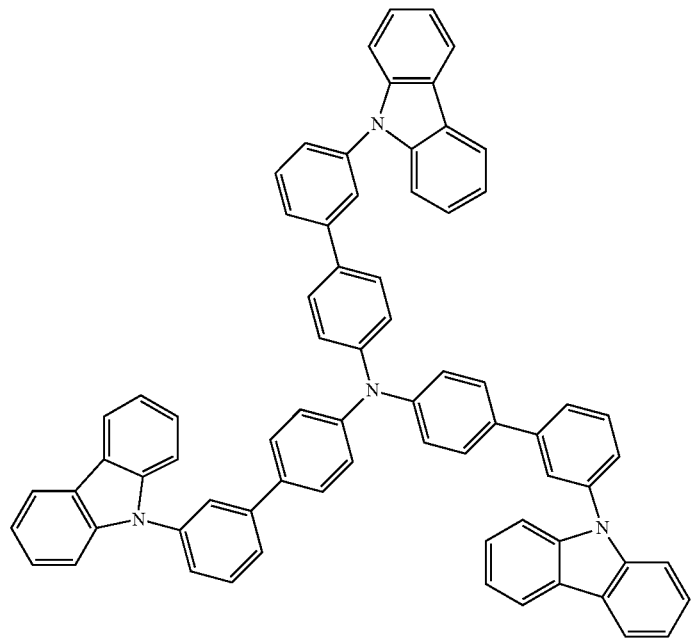 [SMILES: c1cc(-c2ccc(N(c3ccc(-c4cccc(-n5c6ccccc6c6ccccc65)c4)cc3)c3ccc(-c4cccc(-n5c6ccccc6c6ccccc65)c4)cc3)cc2)cc(-n2c3ccccc3c3ccccc32)c1]
HTMV1
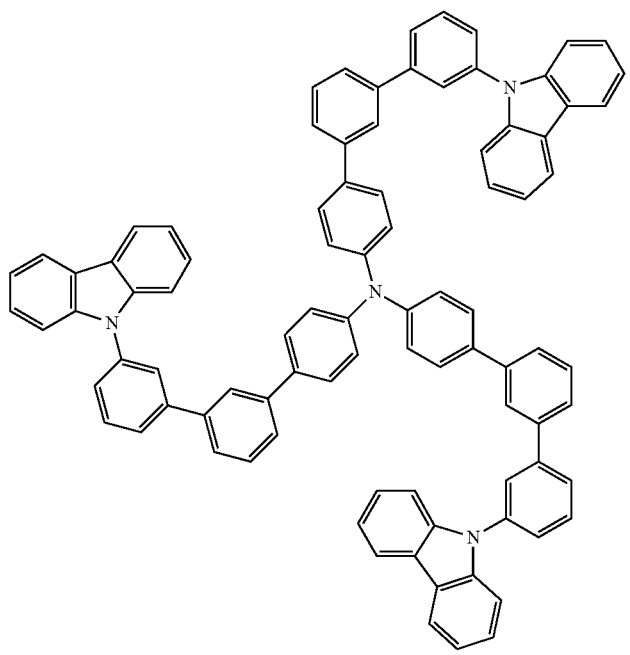 [SMILES: c1cc(-c2ccc(N(c3ccc(-c4cccc(-c5cccc(-n6c7ccccc7c7ccccc76)c5)c4)cc3)c3ccc(-c4cccc(-c5cccc(-n6c7ccccc7c7ccccc76)c5)c4)cc3)cc2)cc(-c2cccc(-n3c4ccccc4c4ccccc43)c2)c1]
HTMV2

TABLE 1-continued
Structures of the materials used
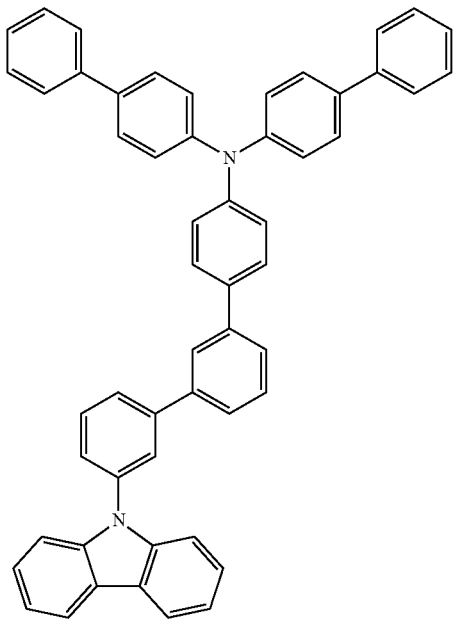 [SMILES: c1ccc(-c2ccc(N(c3ccc(-c4ccccc4)cc3)c3ccc(-c4cccc(-c5cccc(-n6c7ccccc7c7ccccc76)c5)c4)cc3)cc2)cc1]
HTM1
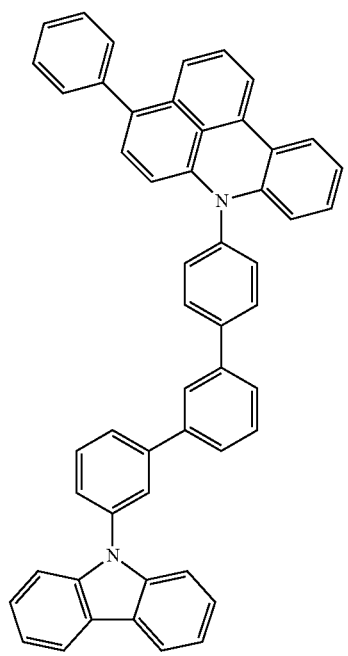
HTM2

TABLE 1-continued
Structures of the materials used
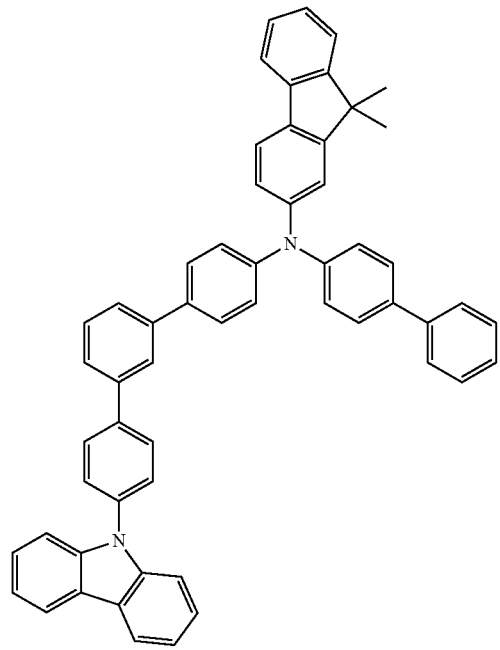 [SMILES: CC1(C)c2ccccc2-c2ccc(N(c3ccc(-c4ccccc4)cc3)c3ccc(-c4cccc(-c5ccc(-n6c7ccccc7c7ccccc76)cc5)c4)cc3)cc21]
HTM3
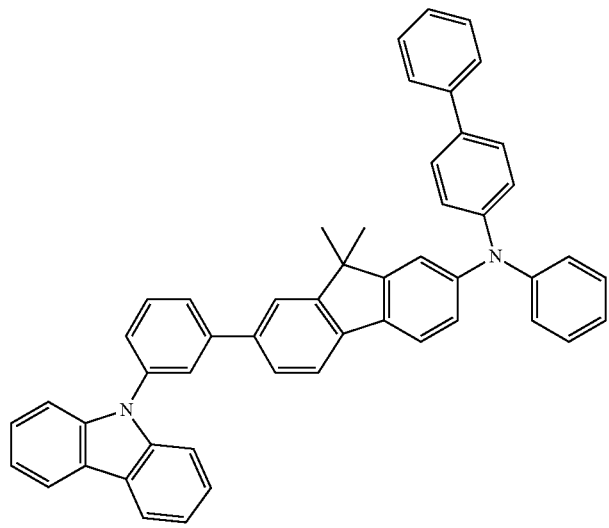 [SMILES: CC1(C)c2cc(-c3cccc(-n4c5ccccc5c5ccccc54)c3)ccc2-c2ccc(N(c3ccccc3)c3ccc(-c4ccccc4)cc3)cc21]
HTM4

TABLE 1-continued

Structures of the materials used

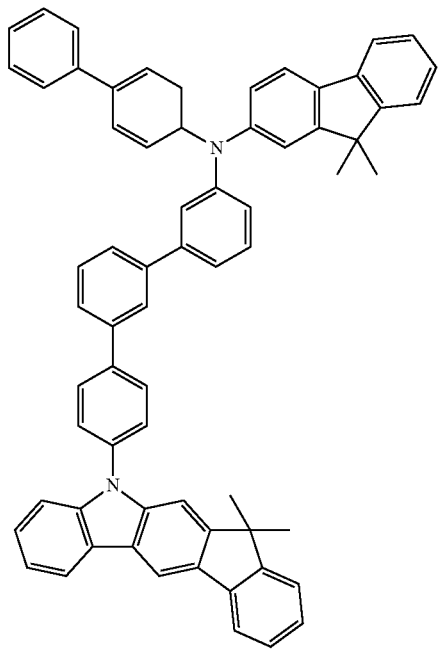 [SMILES: CC1(C)c2ccccc2-c2ccc(N(c3cccc(-c4cccc(-c5ccc(-n6c7ccccc7c7cc8c(cc76)C(C)(C)c6ccccc6-8)cc5)c4)c3)C3C=CC(c4ccccc4)=CC3)cc21]

HTM5

TABLE 2

Structure of the electronic devices

| Ex. | HTL1 Thickness/nm | HTL2 Thickness/nm | HTL3 Thickness/nm | HTL4 Thickness/nm | EML Thickness/nm | ETL Thickness/nm | EIL Thickness/nm |
|---|---|---|---|---|---|---|---|
| V1 | HIM1:F4TCNQ(3%) 20 nm | HIM1 155 nm | NPB:F4TCNQ(3%) 20 nm | NPB 20 nm | H1:SEB1(5%) 20 nm | ETM(50%):LiQ(50%) 30 nm | LiQ 1 nm |
| V2 | HIM1:F4TCNQ(3%) 20 nm | HIM1 155 nm | HTMV1:F4TCNQ(3%) 20 nm | HTMV1 20 nm | H1:SEB1(5%) 20 nm | ETM(50%):LiQ(50%) 30 nm | LiQ 1 nm |
| V3 | HIM1:F4TCNQ(3%) 20 nm | HIM1 155 nm | HTM2:F4TCNQ(3%) 20 nm | HTMV2 20 nm | H1:SEB1(5%) 20 nm | ETM(50%):LiQ(50%) 30 nm | LiQ 1 nm |
| E1 | HIM1:F4TCNQ(3%) 20 nm | HIM1 155 nm | HTM1:F4TCNQ(3%) 20 nm | HTM1 20 nm | H1:SEB1(5%) 20 nm | ETM(50%):LiQ(50%) 30 nm | LiQ 1 nm |
| E2 | HIM1:F4TCNQ(3%) 20 nm | HIM1 155 nm | HTM2:F4TCNQ(3%) 20 nm | HTM2 20 nm | H1:SEB1(5%) 20 nm | ETM(50%):LiQ(50%) 30 nm | LiQ 1 nm |
| E3 | HIM1:F4TCNQ(3%) 20 nm | HIM1 155 nm | HTM3:F4TCNQ(3%) 20 nm | HTM3 20 nm | H1:SEB1(5%) 20 nm | ETM(50%):LiQ(50%) 30 nm | LiQ 1 nm |
| E4 | HIM1:F4TCNQ(3%) 20 nm | HIM1 155 nm | HTM4:F4TCNQ(3%) 20 nm | HTM4 20 nm | H1:SEB1(5%) 20 nm | ETM(50%):LiQ(50%) 30 nm | LiQ 1 nm |
| E5 | HIM1:F4TCNQ(3%) 20 nm | HIM1 155 nm | HTM5:F4TCNQ(3%) 20 nm | HTM5 20 nm | H1:SEB1(5%) 20 nm | ETM(50%):LiQ(50%) 30 nm | LiQ 1 nm |
| V4 | HIM1:F4TCNQ(3%) 20 nm | HIM1 210 nm | NPB:F4TCNQ(3%) 20 nm | NPB 20 nm | H2:TEG(10%) 30 nm | ETM(50%):LiQ(50%) 40 nm | LiQ 1 nm |
| V5 | HIM1:F4TCNQ(3%) 20 nm | HIM1 210 nm | HTMV1:F4TCNQ(3%) 20 nm | HTMV1 20 nm | H2:TEG(10%) 30 nm | ETM(50%):LiQ(50%) 40 nm | LiQ 1 nm |
| V6 | HIM1:F4TCNQ(3%) 20 nm | HIM1 210 nm | HTMV2:F4TCNQ(3%) 20 nm | HTMV2 20 nm | H2:TEG(10%) 30 nm | ETM(50%):LiQ(50%) 40 nm | LiQ 1 nm |
| E6 | HIM1:F4TCNQ(3%) 20 nm | HIM1 210 nm | HTM1:F4TCNQ(3%) 20 nm | HTM1 20 nm | H2:TEG(10%) 30 nm | ETM(50%):LiQ(50%) 40 nm | LiQ 1 nm |
| E7 | HIM1:F4TCNQ(3%) 20 nm | HIM1 210 nm | HTM2:F4TCNQ(3%) 20 nm | HTM2 20 nm | H2:TEG(10%) 30 nm | ETM(50%):LiQ(50%) 40 nm | LiQ 1 nm |
| E8 | HIM1:F4TCNQ(3%) 20 nm | HIM1 210 nm | HTM3:F4TCNQ(3%) 20 nm | HTM3 20 nm | H2:TEG(10%) 30 nm | ETM(50%):LiQ(50%) 40 nm | LiQ 1 nm |
| E9 | HIM1:F4TCNQ(3%) 20 nm | HIM1 210 nm | HTM5:F4TCNQ(3%) 20 nm | HTM5 20 nm | H2:TEG(10%) 30 nm | ETM(50%):LiQ(50%) 40 nm | LiQ 1 nm |

Devices comprising compounds HTM1 to HTM5 according to the invention are produced (E1-E9). Furthermore, devices comprising compounds NPB, HTMV1 and HTMV2 known from the prior art are produced as reference (V1-V6).

The compounds are used as hole-transport materials or as electron-blocking materials in a corresponding layer. In the case of the use as hole-transport material, the compounds in the present examples are doped with a p-dopant.

However, the compounds can also be used in other functions, for example as hole-transport materials without p-doping or as host materials for phosphorescent emitters.

Examples V1-V3 and E1-E5

In a fluorescent OLED, the samples according to the invention E1 with 7.7%, E2 with 7.9%, E3 with 8.2%, E4 with 8.5% and E5 with 7.6% exhibit a higher quantum efficiency at 10 mA/cm$^2$ compared with the reference samples V1 (6.2%), V2 (7.2%) and V3 (6.9%).

The lifetime LT80 at 50 mA/cm$^2$ is also significantly better in the case of all samples according to the invention E1 (260 h), E2 (285 h), E3 (290 h), E4 (290 h) and E5 (300 h) than in the case of the reference samples V1 (135 h), V2 (210 h) and V3 (160 h).

Examples V4-V6 and E6-E9

In a phosphorescent OLED (green emission), reference samples V4 (11.7%), V5 (17.6%) and V6 (17.4%) exhibit somewhat lower or the same quantum efficiencies at 2 mA/cm$^2$ compared with the samples according to the invention E6 (17.7%), E7 (18.2%), E8 (20.6%) and E9 (19.1%).

The lifetimes at 20 mA/cm$^2$ of the samples according to the invention E6 (185 h), E7 (230 h), E8 (230 h), E9 (210 h) are also significantly longer than in the case of the reference samples V4 (80 h), V5 (125 h) and V6 (115 h).

In summary, the examples according to the invention exhibit very good values for the quantum efficiency and for the lifetime, both in the case of fluorescent OLEDs and also in the case of phosphorescent OLEDs. Furthermore, the examples according to the invention exhibit advantages in the aspects mentioned compared with OLEDs which comprise compounds known from the prior art as functional materials.

The invention claimed is:

1. A compound of formula (I)

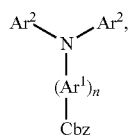

formula (I)

where:
Cbz is a carbazole group, which is optionally substituted by one or more radicals $R^1$, and which is bonded via the carbazole nitrogen atom;
$Ar^1$ is on each occurrence, identically or differently, an aryl group having 6 aromatic ring atoms, which is optionally substituted by one or more radicals $R^2$, where individual groups $Ar^1$ are optionally connected to one another via radicals $R^2$;
$Ar^2$ is on each occurrence, identically or differently, selected from the group consisting of biphenyl, naphthyl, terphenyl, fluorenyl, spirobifluorene, indenofluorenyl, dibenzofuran, and dibenzothiophene, each of which is optionally substituted by one or more radicals $R^2$;
$R^1$ and $R^2$ is on each occurrence, identically or differently, H, D, Si($R^3$)$_3$, a straight-chain alkyl or alkoxy group having 1 to 20 C atoms or a branched or cyclic alkyl group having 3 to 20 C atoms or an alkenyl or alkynyl group having 2 to 20 C atoms, where the above-mentioned groups may each be substituted by one or more radicals $R^3$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which is optionally substituted by one or more radicals $R^3$, where two or more radicals $R^1$ or $R^2$ are optionally linked to one another and may form a ring;
$R^3$ is on each occurrence, identically or differently, H, D, Si($R^4$)$_3$, N($R^4$)$_2$, a straight-chain alkyl group having 1 to 20 C atoms or a branched or cyclic alkyl group having 3 to 20 C atoms or an alkenyl or alkynyl group having 2 to 20 C atoms, where the above-mentioned groups may each be substituted by one or more radicals $R^4$, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which is optionally substituted by one or more radicals $R^4$, where two or more radicals $R^3$ are optionally linked to one another and may form a ring;
$R^4$ is on each occurrence, identically or differently, H, D, F or an aliphatic, aromatic or heteroaromatic organic radical having 1 to 20 C atoms, in which, in addition, one or more H atoms is optionally replaced by D or F; two or more substituents $R^4$ here are optionally linked to one another and may form a ring;
n is 3;
where the compound of the formula (I) contains no further carbazole group besides the group Cbz; and
wherein at least one group $Ar^1$ is selected from ortho-phenylene or meta-phenylene, where the groups are optionally substituted by one or more radicals $R^2$.

2. The compound according to claim 1, wherein the compound of the formula (I) contains no further arylamino group besides the arylamino group shown.

3. The compound according to claim 1, wherein the group Cbz is selected from groups of the formula (Cbz)

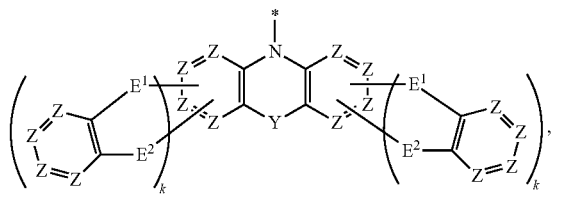

formula (Cbz)

where:

Z is on each occurrence, identically or differently, $CR^1$ or N, where Z is equal to C if a group $E^1$ or $E^2$ is bonded;

$E^1$, $E^2$ is selected on each occurrence, identically or differently, from a single bond, $C(R^1)_2$, $Si(R^1)_2$, C=O, O, S, S=O, $SO_2$ and $NR^1$, where $E^1$ and $E^2$ cannot both be a single bond;

Y is a single bond, $C(R^1)_2$, $Si(R^1)_2$, O, or S;

k is on each occurrence, identically or differently, 0 or 1; where the group of the formula (Cbz) is bonded via the bond labelled with *.

4. The compound according to claim 3, wherein Y in the group of the formula (Cbz) is a single bond.

5. The compound according to claim 3, wherein one of $E^1$ and $E^2$ in the group of the formula (Cbz) within a unit in brackets with index k is a single bond, and the other is selected from $C(R^1)_2$, $Si(R^1)_2$, C=O, O, S, S=O, $SO_2$ and $NR^1$.

6. A process for the preparation of a compound of the formula (I) according to claim 1, which comprises reacting a carbazole derivative with an aryl compound in a coupling reaction.

7. A formulation comprising at least one compound of the formula (I) according to claim 1 and at least one solvent.

8. An electronic device comprising at least one compound of the formula (I) according to claim 1.

9. The electronic device according to claim 8, wherein the device is selected from the group consisting of an organic integrated circuit (OIC), an organic field-effect transistor (OFET), an organic thin-film transistor (OTFT), an organic light-emitting transistor (OLET), an organic solar cell (OSC), an organic optical detector, an organic photoreceptor, an organic field-quench device (OFQD), an organic light-emitting electrochemical cell (OLEC), an organic laser diode (O-laser) and an organic electroluminescent device (OLED).

10. An organic electroluminescent device comprising the compound of the formula (I) according to claim 1 in a hole-transport layer, an electron-blocking layer, a hole-injection layer or in an emitting layer.

11. An organic electroluminescent device comprising a compound of formula (I)

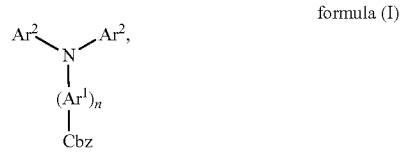

formula (I)

where:

Cbz is a carbazole group, which is optionally substituted by one or more radicals $R^1$, and which is bonded via the carbazole nitrogen atom;

$Ar^1$ is on each occurrence, identically or differently, an aryl group having 6 aromatic ring atoms, which is optionally substituted by one or more radicals $R^2$, where individual groups $Ar^1$ are optionally connected to one another via radicals $R^2$;

$Ar^2$ is on each occurrence, identically or differently, selected from the group consisting of biphenyl, naphthyl, terphenyl, fluorenyl, spirobifluorene, indenofluorenyl, dibenzofuran, and dibenzothiophene, each of which is optionally substituted by one or more radicals $R^2$;

$R^1$ and $R^2$ is on each occurrence, identically or differently, H, D, F, Cl, Br, I, C(=O)$R^3$, CN, Si($R^3$)$_3$, P(=O)($R^3$)$_2$, S(=O)$R^3$, S(=O)$_2$$R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups is optionally replaced by —$R^3$C=C$R^3$—, —C≡C—, Si($R^3$)$_2$, C=O, C=S, C=$NR^3$, —C(=O)O—, —C(=O)$NR^3$—, $NR^3$, P(=O)($R^3$), —O—, —S—, SO or $SO_2$ and where one or more H atoms in the above-mentioned groups is optionally replaced by D, F, Cl, Br, I or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which is optionally substituted by one or more radicals $R^3$, where two or more radicals $R^1$ or $R^2$ are optionally linked to one another and may form a ring;

$R^3$ is on each occurrence, identically or differently, H, D, F, Cl, Br, I, C(=O)$R^4$, CN, Si($R^4$)$_3$, N($R^4$)$_2$, P(=O)($R^4$)$_2$, S(=O)$R^4$, S(=O)$_2$$R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups is optionally replaced by —$R^4$C=C$R^4$—, —C≡C—, Si($R^4$)$_2$, C=O, C=$NR^4$, —C(=O)O—, —C(=O)$NR^4$—, $NR^4$, P(=O)($R^4$), —O—, —S—, SO or $SO_2$ and where one or more H atoms in the above-mentioned groups is optionally replaced by D, F, Cl, Br, I or CN, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which is optionally substituted by one or more radicals $R^4$, where two or more radicals $R^3$ are optionally linked to one another and may form a ring;

$R^4$ is on each occurrence, identically or differently, H, D, F or an aliphatic, aromatic or heteroaromatic organic radical having 1 to 20 C atoms, in which, in addition, one or more H atoms is optionally replaced by D or F; two or more substituents $R^4$ here are optionally linked to one another and may form a ring;

n is 3;

where the compound of the formula (I) contains no further carbazole group besides the group Cbz; and wherein at least one group $Ar^1$ is selected from ortho-phenylene or meta-phenylene, where the groups is optionally substituted by one or more radicals $R^2$;

wherein the compound of formula (I) is present in a hole-transport layer, an electron-blocking layer, a hole-injection layer or in an emitting layer.

12. A compound selected from the group consisting of:
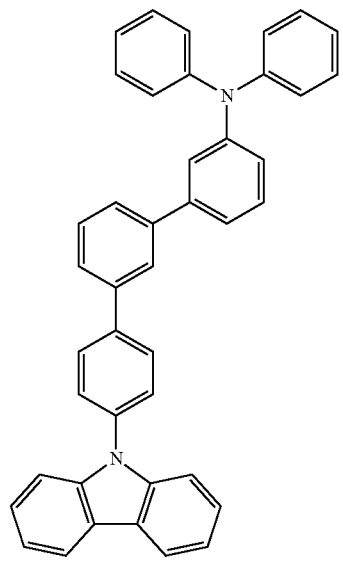 [SMILES: c1ccc(N(c2ccccc2)c2cccc(-c3cccc(-c4ccc(-n5c6ccccc6c6ccccc65)cc4)c3)c2)cc1]
1
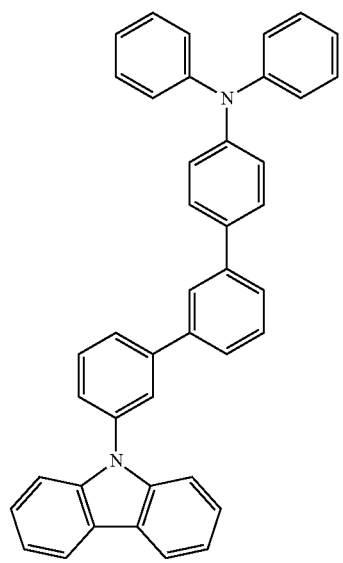 [SMILES: c1ccc(N(c2ccccc2)c2ccc(-c3cccc(-c4cccc(-n5c6ccccc6c6ccccc65)c4)c3)cc2)cc1]
2

-continued
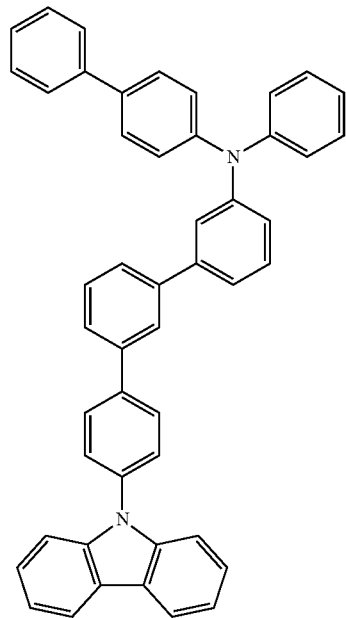 [SMILES: c1ccc(-c2ccc(N(c3ccccc3)c3cccc(-c4cccc(-c5ccc(-n6c7ccccc7c7ccccc76)cc5)c4)c3)cc2)cc1]
3
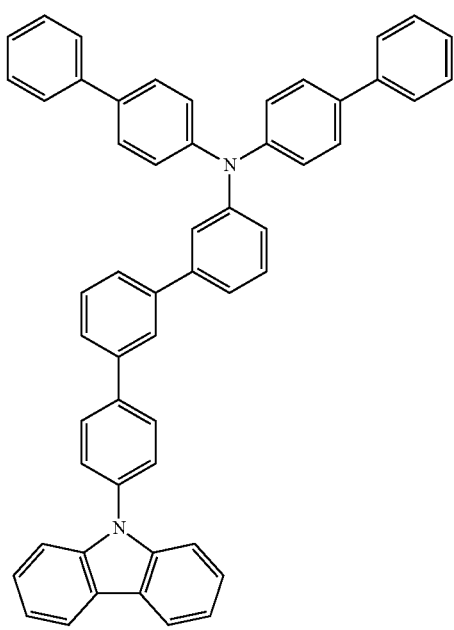
4

-continued
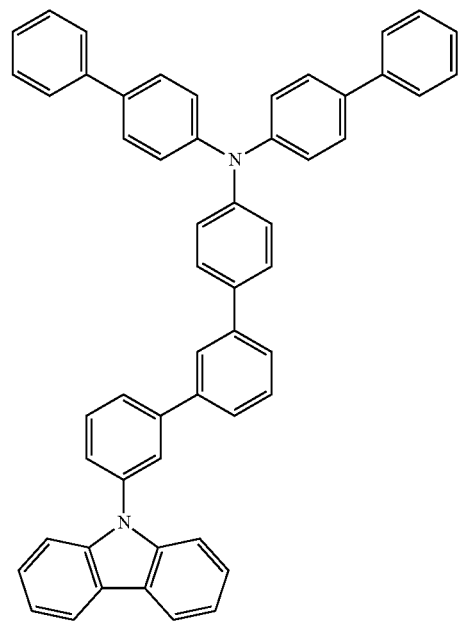 [SMILES: c1ccc(-c2ccc(N(c3ccc(-c4ccccc4)cc3)c3ccc(-c4cccc(-c5cccc(-n6c7ccccc7c7ccccc76)c5)c4)cc3)cc2)cc1]
5
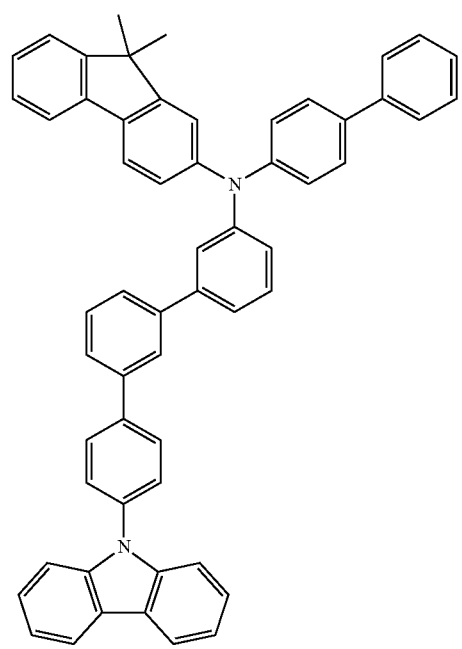 [SMILES: CC1(C)c2ccccc2-c2ccc(N(c3ccc(-c4ccccc4)cc3)c3cccc(-c4cccc(-c5ccc(-n6c7ccccc7c7ccccc76)cc5)c4)c3)cc21]
6

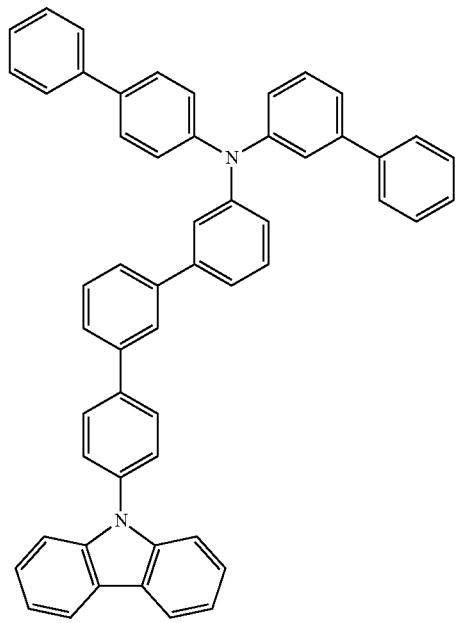 [SMILES: c1ccc(-c2ccc(N(c3cccc(-c4ccccc4)c3)c3cccc(-c4cccc(-c5ccc(-n6c7ccccc7c7ccccc76)cc5)c4)c3)cc2)cc1]
7
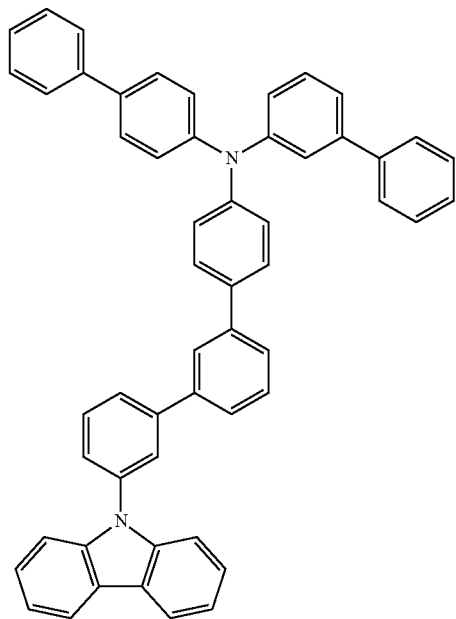 [SMILES: c1ccc(-c2ccc(N(c3ccc(-c4cccc(-c5cccc(-n6c7ccccc7c7ccccc76)c5)c4)cc3)c3cccc(-c4ccccc4)c3)cc2)cc1]
8

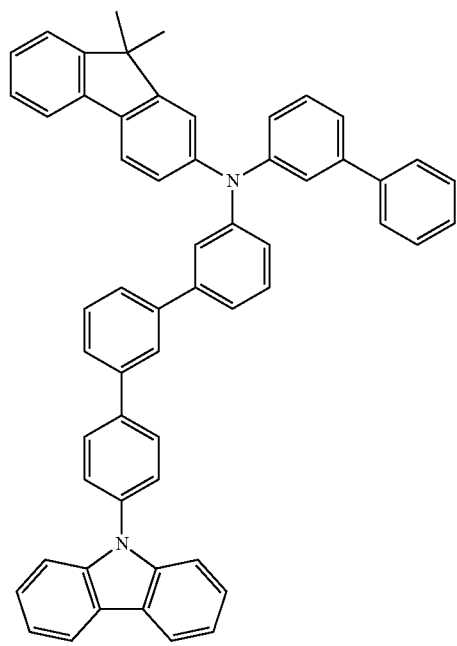 [SMILES: CC1(C)c2ccccc2-c2ccc(N(c3cccc(-c4ccccc4)c3)c3cccc(-c4cccc(-c5ccc(-n6c7ccccc7c7ccccc76)cc5)c4)c3)cc21]
9
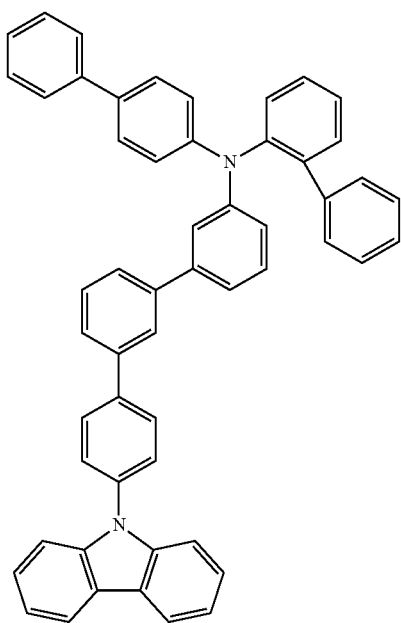 [SMILES: c1ccc(-c2ccc(N(c3cccc(-c4cccc(-c5ccc(-n6c7ccccc7c7ccccc76)cc5)c4)c3)c3ccccc3-c3ccccc3)cc2)cc1]
10

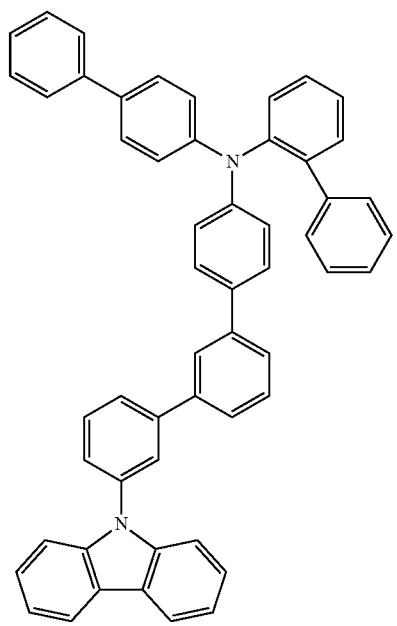 [SMILES: c1ccc(-c2ccc(N(c3ccc(-c4cccc(-c5cccc(-n6c7ccccc7c7ccccc76)c5)c4)cc3)c3ccccc3-c3ccccc3)cc2)cc1]
11
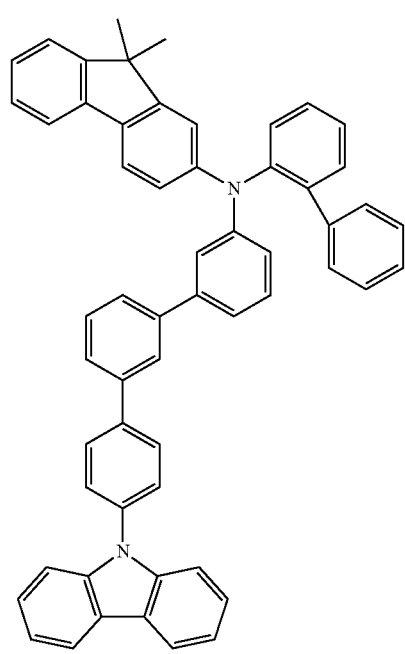 [SMILES: CC1(C)c2ccccc2-c2ccc(N(c3cccc(-c4cccc(-c5ccc(-n6c7ccccc7c7ccccc76)cc5)c4)c3)c3ccccc3-c3ccccc3)cc21]
12

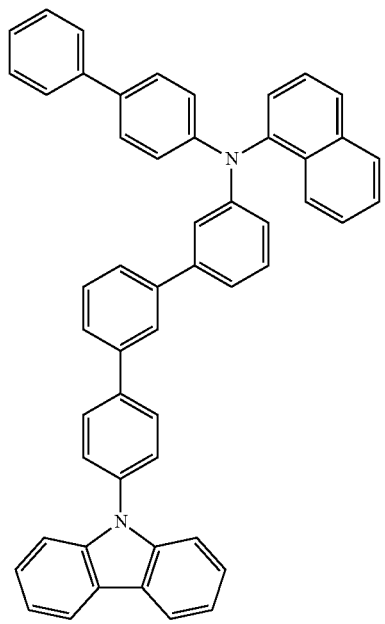 [SMILES: c1ccc(-c2ccc(N(c3cccc(-c4cccc(-c5ccc(-n6c7ccccc7c7ccccc76)cc5)c4)c3)c3cccc4ccccc34)cc2)cc1]
13
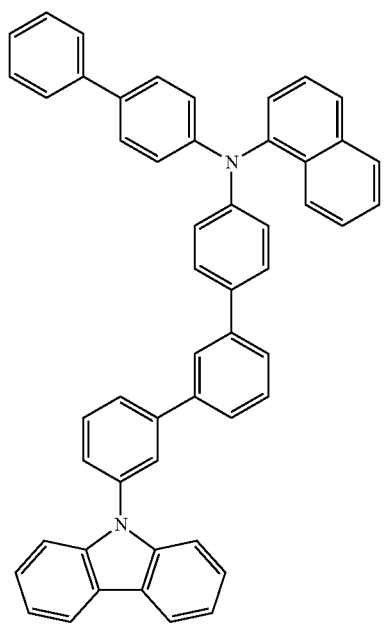 [SMILES: c1ccc(-c2ccc(N(c3ccc(-c4cccc(-c5cccc(-n6c7ccccc7c7ccccc76)c5)c4)cc3)c3cccc4ccccc34)cc2)cc1]
14

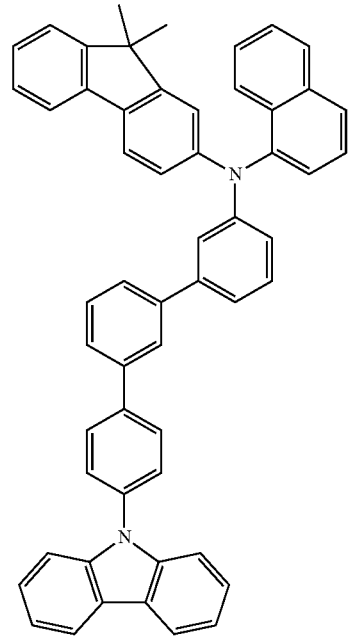 [SMILES: CC1(C)c2ccccc2-c2ccc(N(c3cccc(-c4cccc(-c5ccc(-n6c7ccccc7c7ccccc76)cc5)c4)c3)c3cccc4ccccc34)cc21]
15
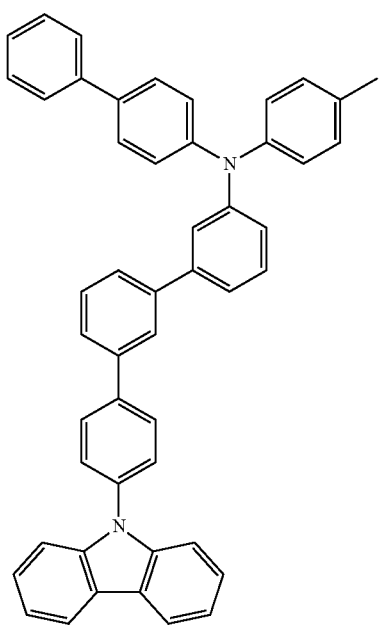 [SMILES: Cc1ccc(N(c2ccc(-c3ccccc3)cc2)c2cccc(-c3cccc(-c4ccc(-n5c6ccccc6c6ccccc65)cc4)c3)c2)cc1]
16

-continued
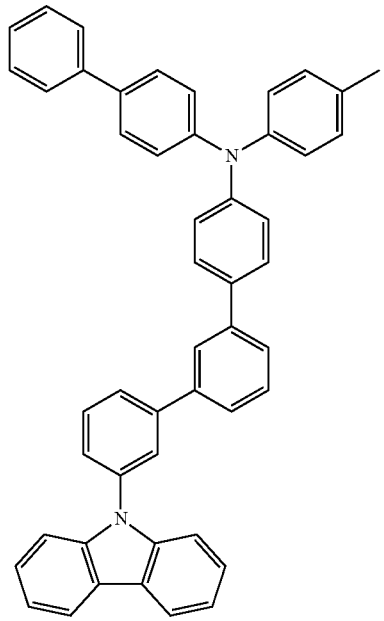 [SMILES: Cc1ccc(N(c2ccc(-c3ccccc3)cc2)c2ccc(-c3cccc(-c4cccc(-n5c6ccccc6c6ccccc65)c4)c3)cc2)cc1]
17
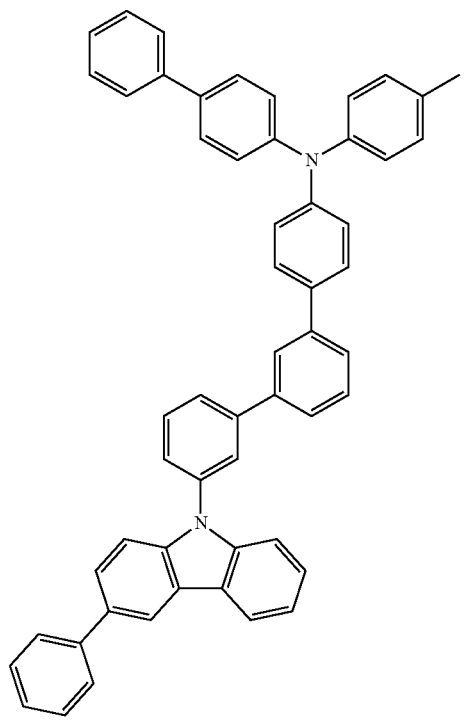 [SMILES: Cc1ccc(N(c2ccc(-c3ccccc3)cc2)c2ccc(-c3cccc(-c4cccc(-n5c6ccccc6c6cc(-c7ccccc7)ccc65)c4)c3)cc2)cc1]
18

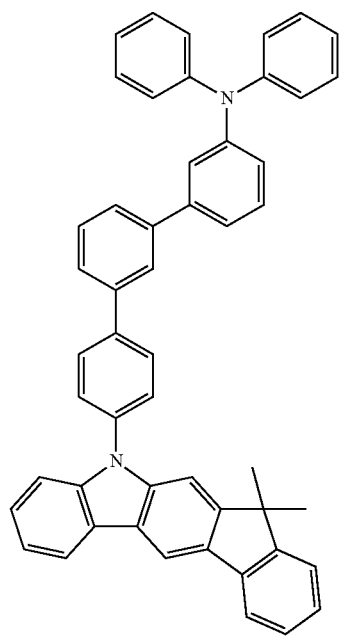 [SMILES: CC1(C)c2ccccc2-c2cc3c4ccccc4n(-c4ccc(-c5cccc(-c6cccc(N(c7ccccc7)c7ccccc7)c6)c5)cc4)c3cc21]
19
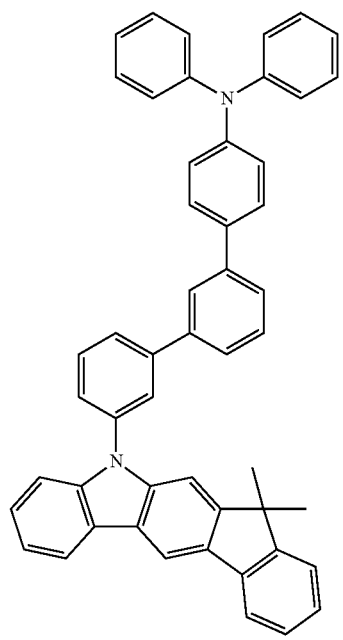 [SMILES: CC1(C)c2ccccc2-c2cc3c4ccccc4n(-c4cccc(-c5cccc(-c6ccc(N(c7ccccc7)c7ccccc7)cc6)c5)c4)c3cc21]
20

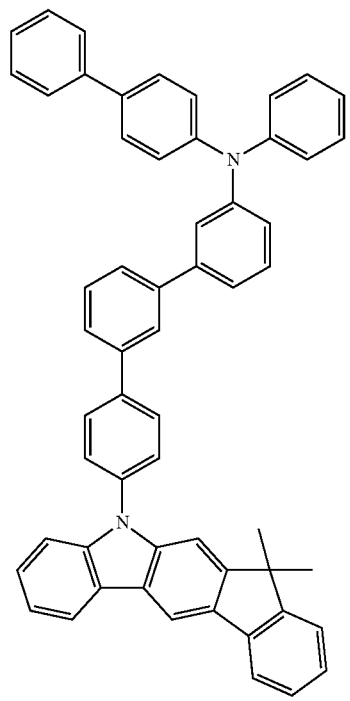 [SMILES: CC1(C)c2ccccc2-c2cc3c4ccccc4n(-c4ccc(-c5cccc(-c6cccc(N(c7ccccc7)c7ccc(-c8ccccc8)cc7)c6)c5)cc4)c3cc21]
21
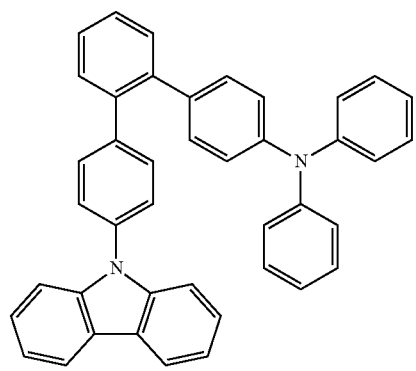 [SMILES: c1ccc(N(c2ccccc2)c2ccc(-c3ccccc3-c3ccc(-n4c5ccccc5c5ccccc54)cc3)cc2)cc1]
22
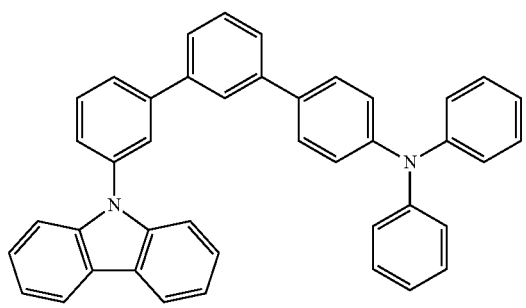 [SMILES: c1ccc(N(c2ccccc2)c2ccc(-c3cccc(-c4cccc(-n5c6ccccc6c6ccccc65)c4)c3)cc2)cc1]
23

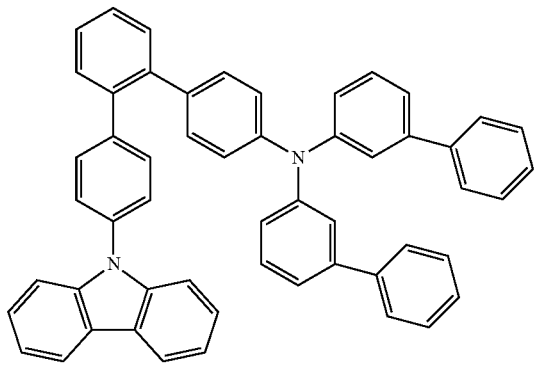 [SMILES: c1ccc(-c2cccc(N(c3ccc(-c4ccccc4-c4ccc(-n5c6ccccc6c6ccccc65)cc4)cc3)c3cccc(-c4ccccc4)c3)c2)cc1]
24
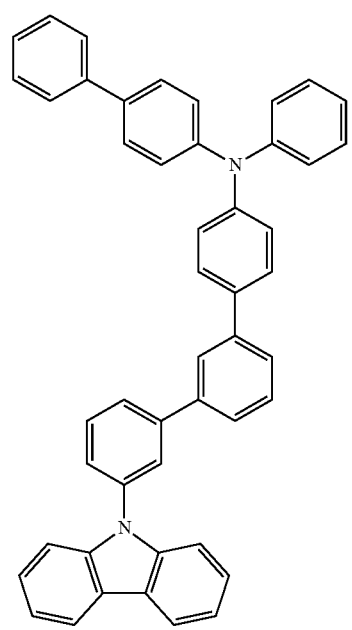 [SMILES: c1ccc(-c2ccc(N(c3ccccc3)c3ccc(-c4cccc(-c5cccc(-n6c7ccccc7c7ccccc76)c5)c4)cc3)cc2)cc1]
25
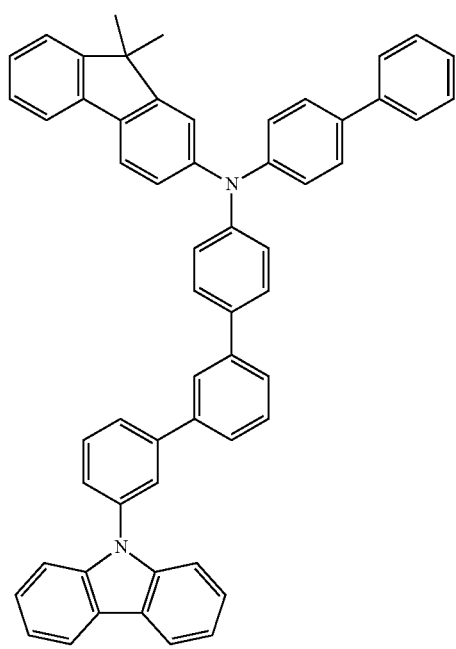 [SMILES: CC1(C)c2ccccc2-c2ccc(N(c3ccc(-c4ccccc4)cc3)c3ccc(-c4cccc(-c5cccc(-n6c7ccccc7c7ccccc76)c5)c4)cc3)cc21]
26

-continued
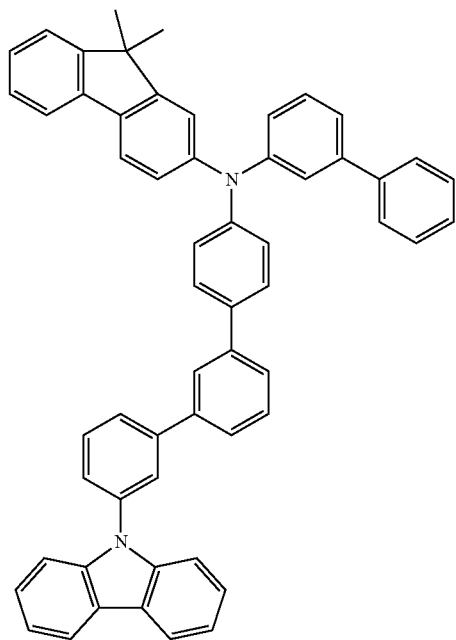 [SMILES: CC1(C)c2ccccc2-c2ccc(N(c3ccc(-c4cccc(-c5cccc(-n6c7ccccc7c7ccccc76)c5)c4)cc3)c3cccc(-c4ccccc4)c3)cc21]
27
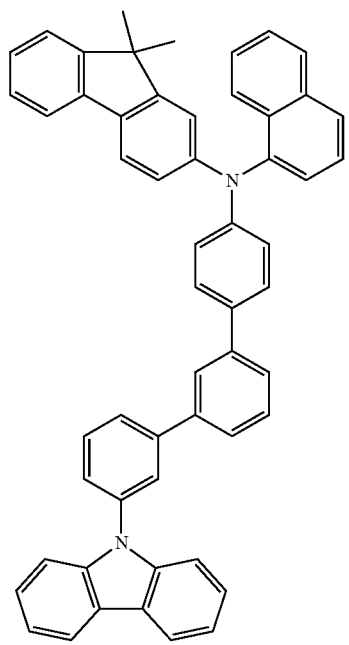 [SMILES: CC1(C)c2ccccc2-c2ccc(N(c3ccc(-c4cccc(-c5cccc(-n6c7ccccc7c7ccccc76)c5)c4)cc3)c3cccc4ccccc34)cc21]
28

-continued
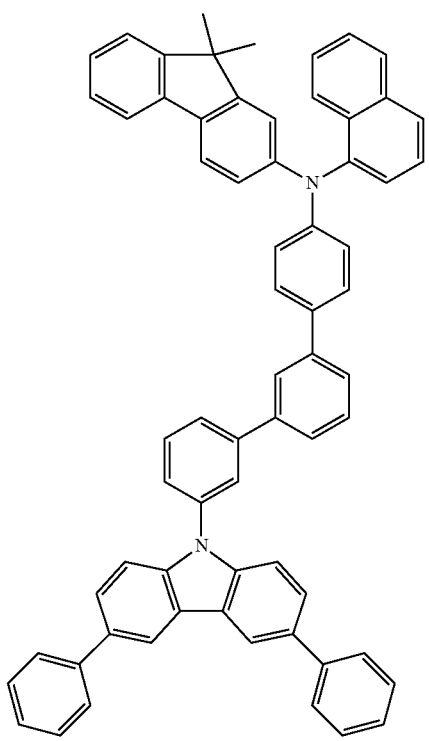 [SMILES: CC1(C)c2ccccc2-c2ccc(N(c3ccc(-c4cccc(-c5cccc(-n6c7ccc(-c8ccccc8)cc7c7cc(-c8ccccc8)ccc76)c5)c4)cc3)c3cccc4ccccc34)cc21]
29
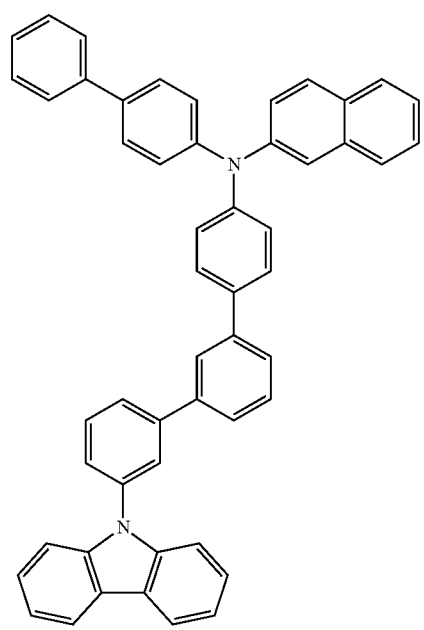 [SMILES: c1ccc(-c2ccc(N(c3ccc(-c4cccc(-c5cccc(-n6c7ccccc7c7ccccc76)c5)c4)cc3)c3ccc4ccccc4c3)cc2)cc1]
30

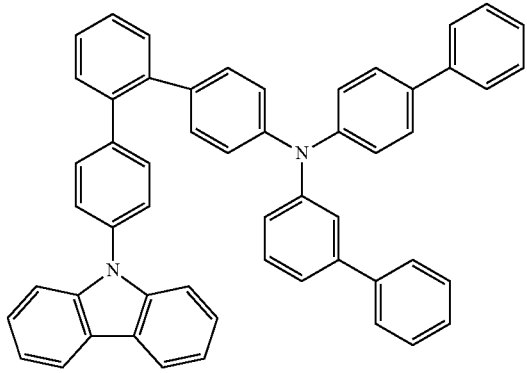 [SMILES: c1ccc(-c2ccc(N(c3ccc(-c4ccccc4-c4ccc(-n5c6ccccc6c6ccccc65)cc4)cc3)c3cccc(-c4ccccc4)c3)cc2)cc1]
31
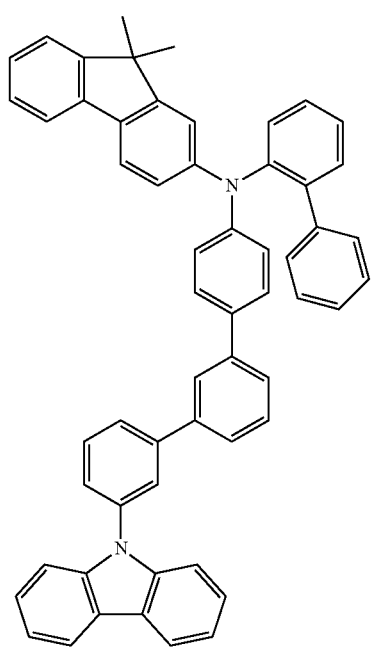 [SMILES: CC1(C)c2ccccc2-c2ccc(N(c3ccc(-c4cccc(-c5cccc(-n6c7ccccc7c7ccccc76)c5)c4)cc3)c3ccccc3-c3ccccc3)cc21]
32

-continued
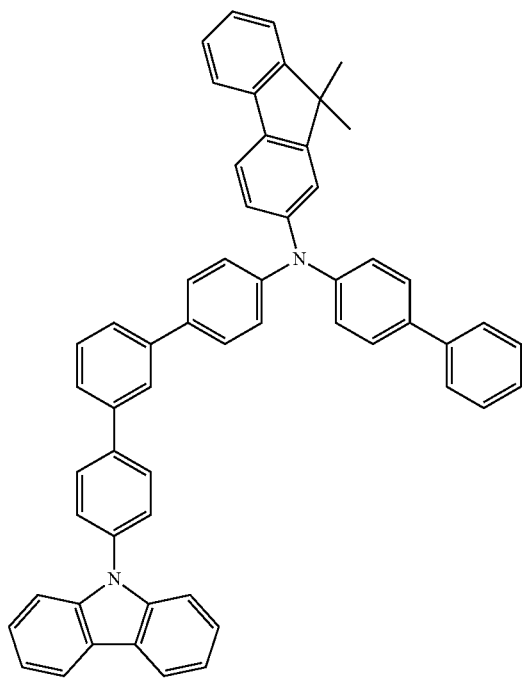 [SMILES: CC1(C)c2ccccc2-c2ccc(N(c3ccc(-c4ccccc4)cc3)c3ccc(-c4cccc(-c5ccc(-n6c7ccccc7c7ccccc76)cc5)c4)cc3)cc21]
33
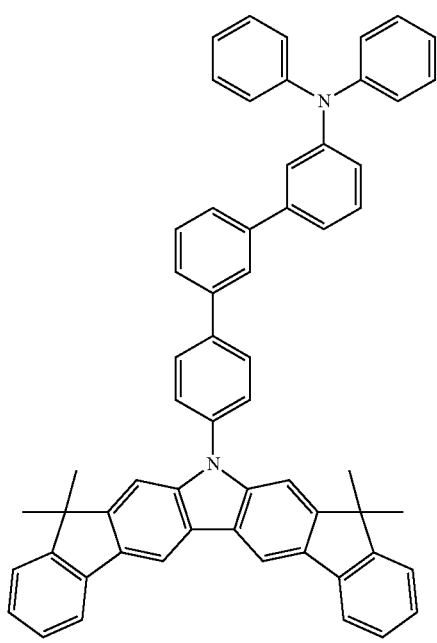 [SMILES: CC1(C)c2ccccc2-c2cc3c4cc5c(cc4n(-c4ccc(-c6cccc(-c7cccc(N(c8ccccc8)c8ccccc8)c7)c6)cc4)c3cc21)C(C)(C)c1ccccc1-5]
34

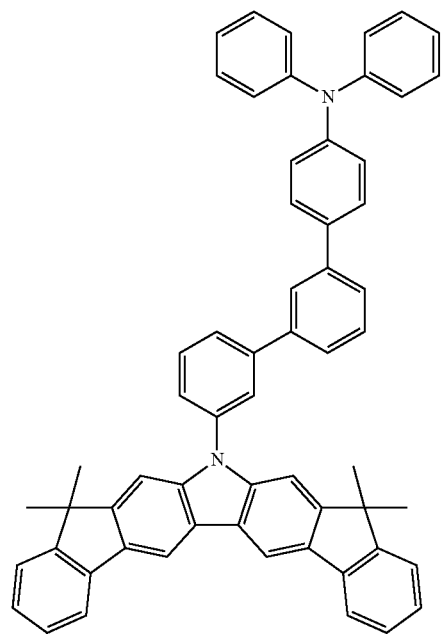 [SMILES: CC1(C)c2ccccc2-c2cc3c4cc5c(cc4n(-c4cccc(-c6cccc(-c7ccc(N(c8ccccc8)c8ccccc8)cc7)c6)c4)c3cc21)C(C)(C)c1ccccc1-5]
35
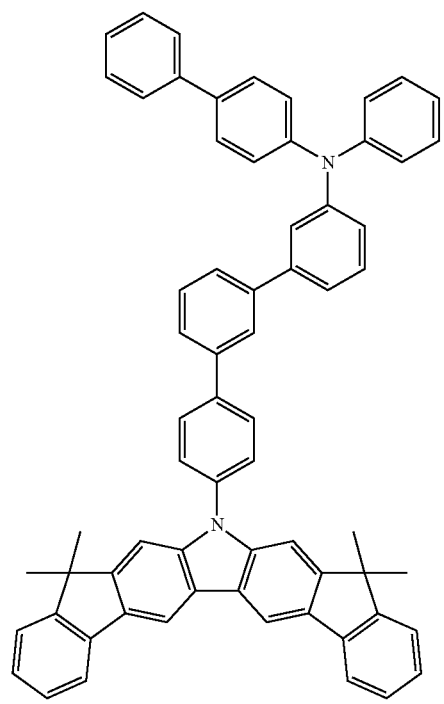 [SMILES: CC1(C)c2ccccc2-c2cc3c4cc5c(cc4n(-c4ccc(-c6cccc(-c7cccc(N(c8ccccc8)c8ccc(-c9ccccc9)cc8)c7)c6)cc4)c3cc21)C(C)(C)c1ccccc1-5]
36

-continued
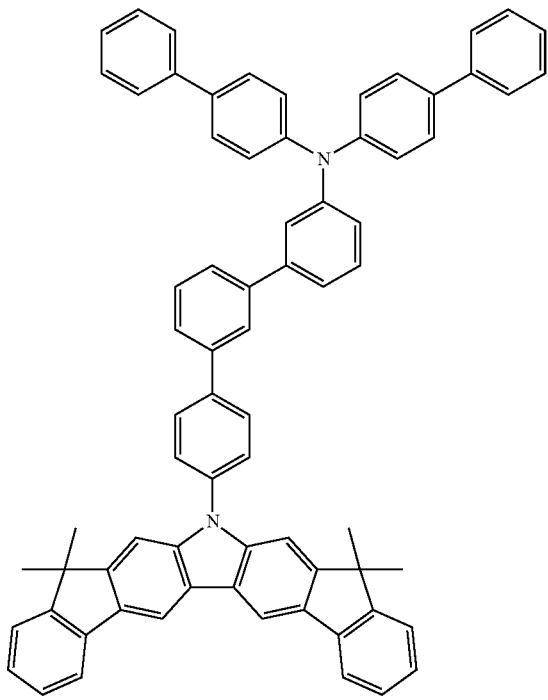 [SMILES: CC1(C)c2ccccc2-c2cc3c4cc5c(cc4n(-c4ccc(-c6cccc(-c7cccc(N(c8ccc(-c9ccccc9)cc8)c8ccc(-c9ccccc9)cc8)c7)c6)cc4)c3cc21)C(C)(C)c1ccccc1-5]
37
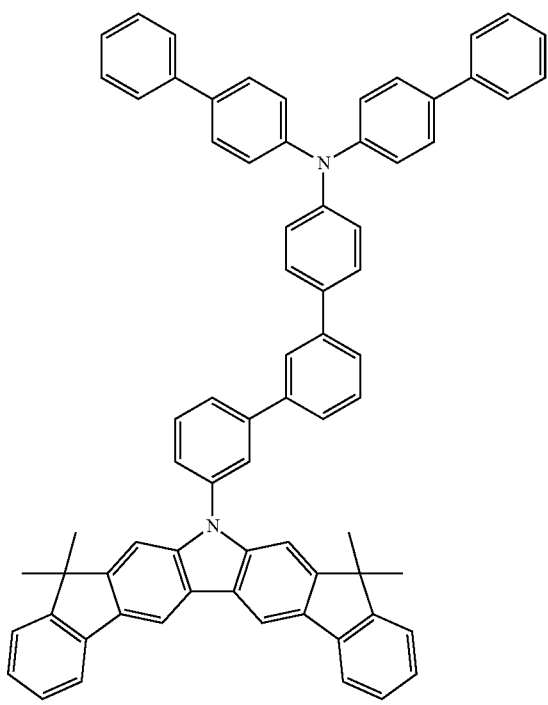 [SMILES: CC1(C)c2ccccc2-c2cc3c4cc5c(cc4n(-c4cccc(-c6cccc(-c7ccc(N(c8ccc(-c9ccccc9)cc8)c8ccc(-c9ccccc9)cc8)cc7)c6)c4)c3cc21)C(C)(C)c1ccccc1-5]
38

-continued
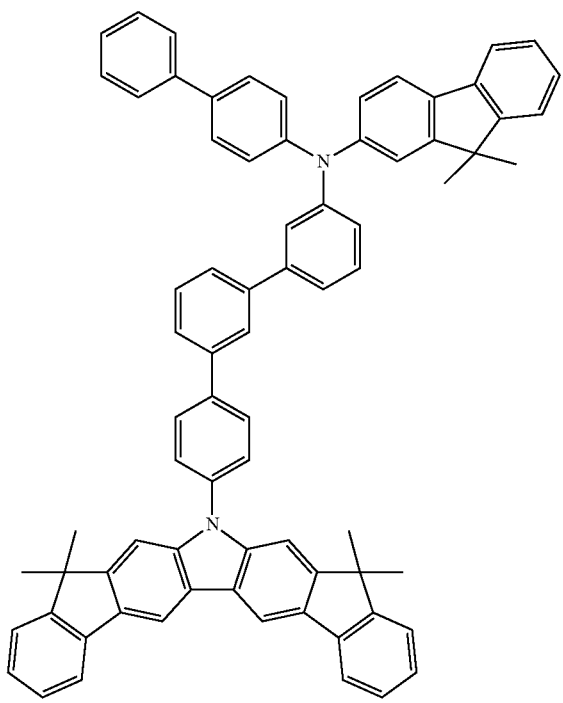 [SMILES: CC1(C)c2ccccc2-c2ccc(N(c3ccc(-c4ccccc4)cc3)c3cccc(-c4cccc(-c5ccc(-n6c7cc8c(cc7c7cc9c(cc76)C(C)(C)c6ccccc6-9)-c6ccccc6C8(C)C)cc5)c4)c3)cc21]
39
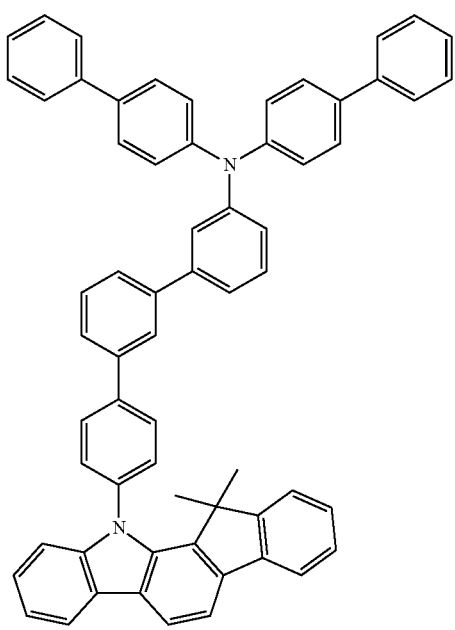 [SMILES: CC1(C)c2ccccc2-c2ccc3c4ccccc4n(-c4ccc(-c5cccc(-c6cccc(N(c7ccc(-c8ccccc8)cc7)c7ccc(-c8ccccc8)cc7)c6)c5)cc4)c3c21]
40

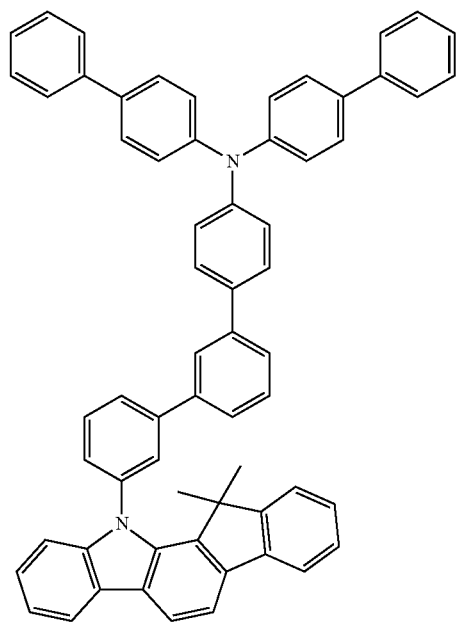 [SMILES: CC1(C)c2ccccc2-c2ccc3c4ccccc4n(-c4cccc(-c5cccc(-c6ccc(N(c7ccc(-c8ccccc8)cc7)c7ccc(-c8ccccc8)cc7)cc6)c5)c4)c3c21]
41
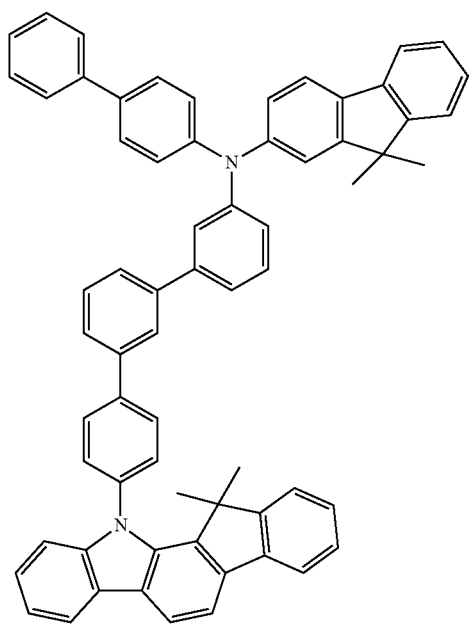 [SMILES: CC1(C)c2ccccc2-c2ccc(N(c3ccc(-c4ccccc4)cc3)c3cccc(-c4cccc(-c5ccc(-n6c7ccccc7c7ccc8c(c76)C(C)(C)c6ccccc6-8)cc5)c4)c3)cc21]
42

-continued
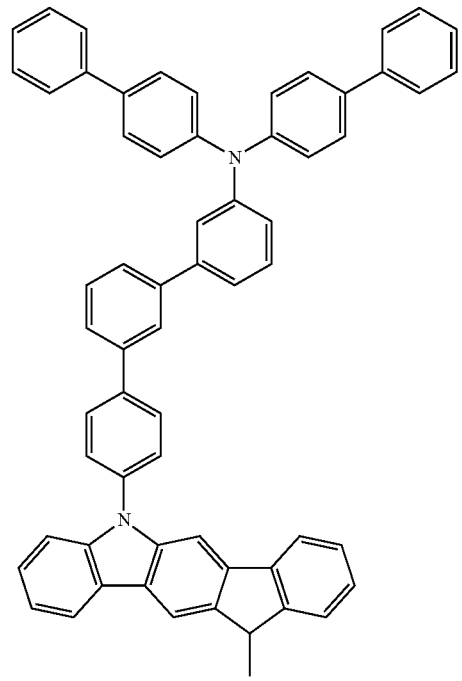 [SMILES: CC1c2ccccc2-c2cc3c(cc21)c1ccccc1n3-c1ccc(-c2cccc(-c3cccc(N(c4ccc(-c5ccccc5)cc4)c4ccc(-c5ccccc5)cc4)c3)c2)cc1]
43
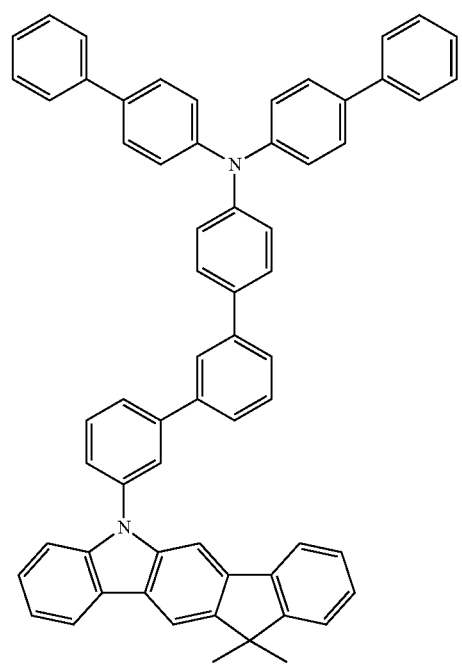 [SMILES: CC1(C)c2ccccc2-c2cc3c(cc21)c1ccccc1n3-c1cccc(-c2cccc(-c3ccc(N(c4ccc(-c5ccccc5)cc4)c4ccc(-c5ccccc5)cc4)cc3)c2)c1]
44

-continued
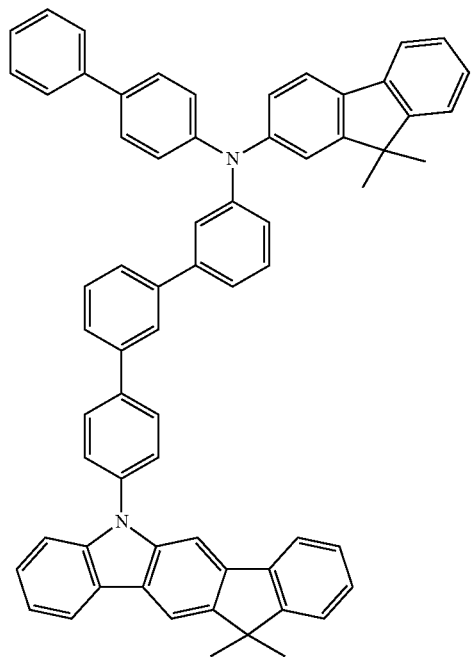 [SMILES: CC1(C)c2ccccc2-c2ccc(N(c3ccc(-c4ccccc4)cc3)c3cccc(-c4cccc(-c5ccc(-n6c7ccccc7c7cc8c(cc76)-c6ccccc6C8(C)C)cc5)c4)c3)cc21]
45
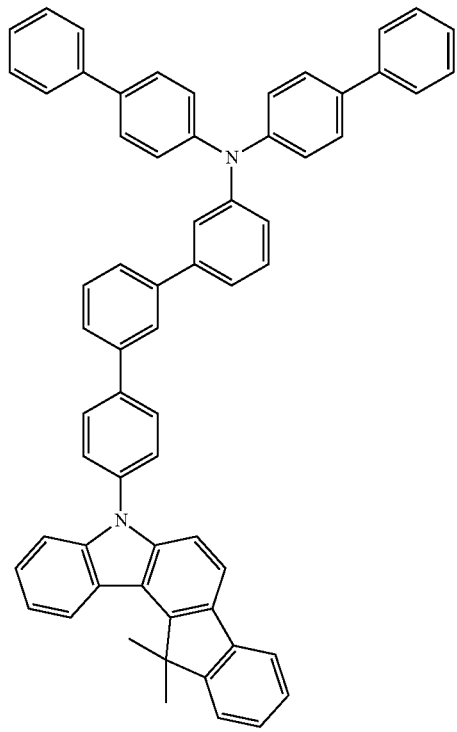 [SMILES: CC1(C)c2ccccc2-c2ccc3c(c21)c1ccccc1n3-c1ccc(-c2cccc(-c3cccc(N(c4ccc(-c5ccccc5)cc4)c4ccc(-c5ccccc5)cc4)c3)c2)cc1]
46

-continued
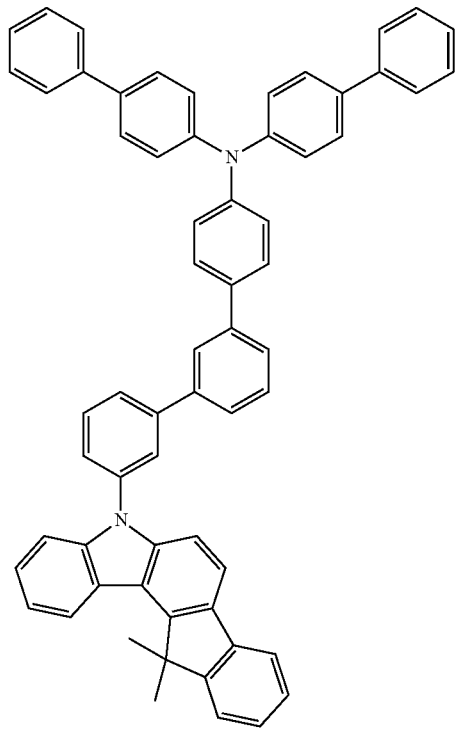 [SMILES: CC1(C)c2ccccc2-c2ccc3c(c21)c1ccccc1n3-c1cccc(-c2cccc(-c3ccc(N(c4ccc(-c5ccccc5)cc4)c4ccc(-c5ccccc5)cc4)cc3)c2)c1]
47
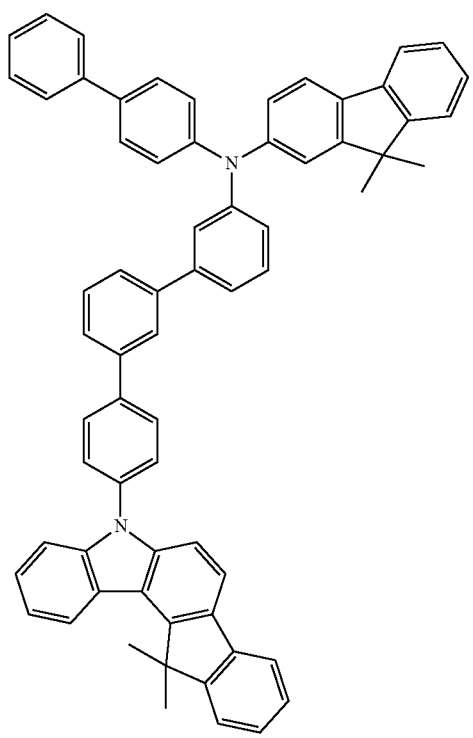 [SMILES: CC1(C)c2ccccc2-c2ccc(N(c3ccc(-c4ccccc4)cc3)c3cccc(-c4cccc(-c5ccc(-n6c7ccccc7c7c8c(ccc76)-c6ccccc6C8(C)C)cc5)c4)c3)cc21]
48

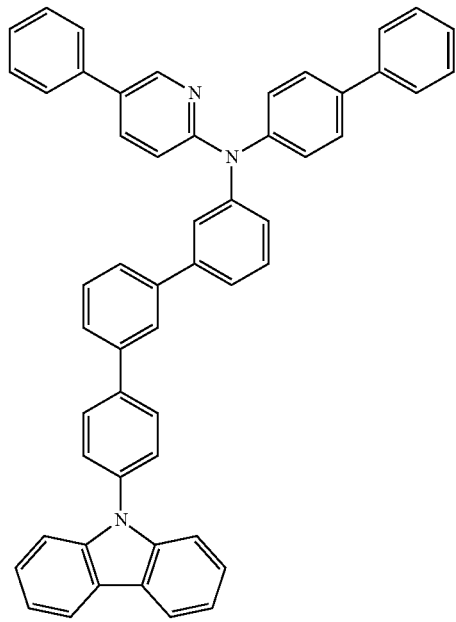 [SMILES: c1ccc(-c2ccc(N(c3cccc(-c4cccc(-c5ccc(-n6c7ccccc7c7ccccc76)cc5)c4)c3)c3ccc(-c4ccccc4)cn3)cc2)cc1]
49
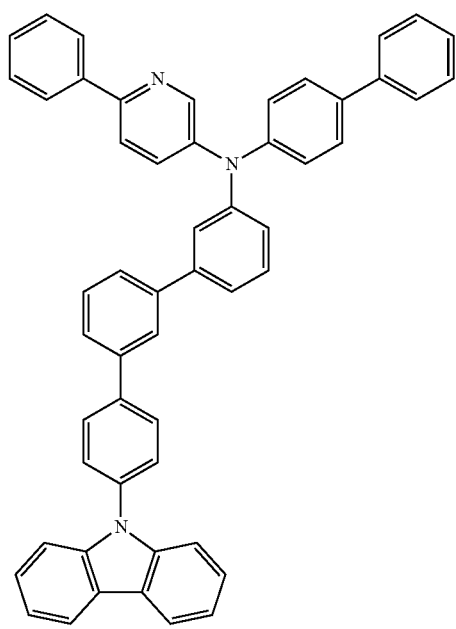 [SMILES: c1ccc(-c2ccc(N(c3ccc(-c4ccccc4)nc3)c3cccc(-c4cccc(-c5ccc(-n6c7ccccc7c7ccccc76)cc5)c4)c3)cc2)cc1]
50

-continued
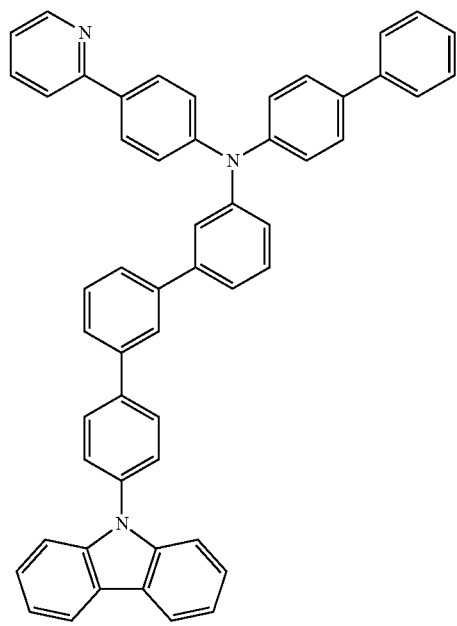 [SMILES: c1ccc(-c2ccc(N(c3ccc(-c4ccccn4)cc3)c3cccc(-c4cccc(-c5ccc(-n6c7ccccc7c7ccccc76)cc5)c4)c3)cc2)cc1]
51
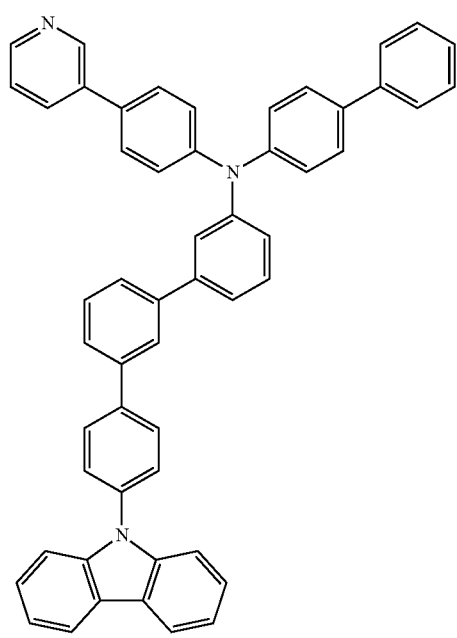 [SMILES: c1ccc(-c2ccc(N(c3ccc(-c4cccnc4)cc3)c3cccc(-c4cccc(-c5ccc(-n6c7ccccc7c7ccccc76)cc5)c4)c3)cc2)cc1]
52

| | |
|---|---|
| 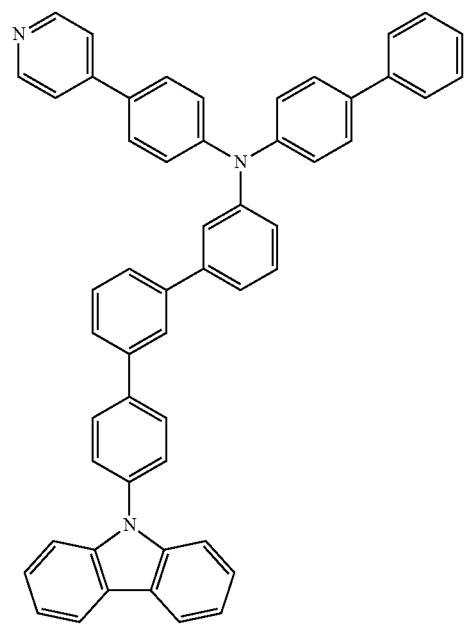 [SMILES: c1ccc(-c2ccc(N(c3ccc(-c4ccncc4)cc3)c3cccc(-c4cccc(-c5ccc(-n6c7ccccc7c7ccccc76)cc5)c4)c3)cc2)cc1] | 53 |
| 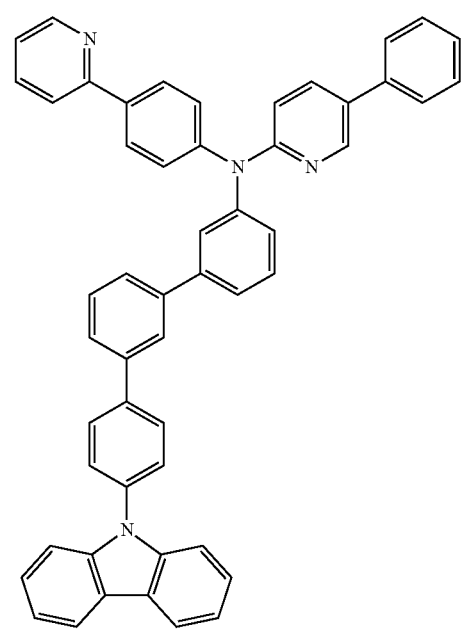 [SMILES: c1ccc(-c2ccc(N(c3ccc(-c4ccccn4)cc3)c3cccc(-c4cccc(-c5ccc(-n6c7ccccc7c7ccccc76)cc5)c4)c3)nc2)cc1] | 54 |

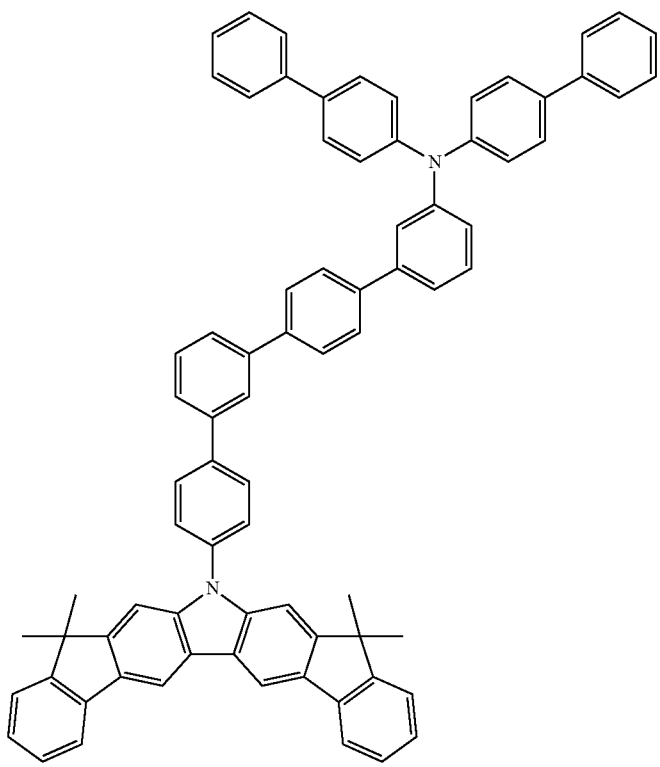 [SMILES: CC1(C)c2ccccc2-c2cc3c4cc5c(cc4n(-c4ccc(-c6cccc(-c7ccc(-c8cccc(N(c9ccc(-c%10ccccc%10)cc9)c9ccc(-c%10ccccc%10)cc9)c8)cc7)c6)cc4)c3cc21)C(C)(C)c1ccccc1-5]
55
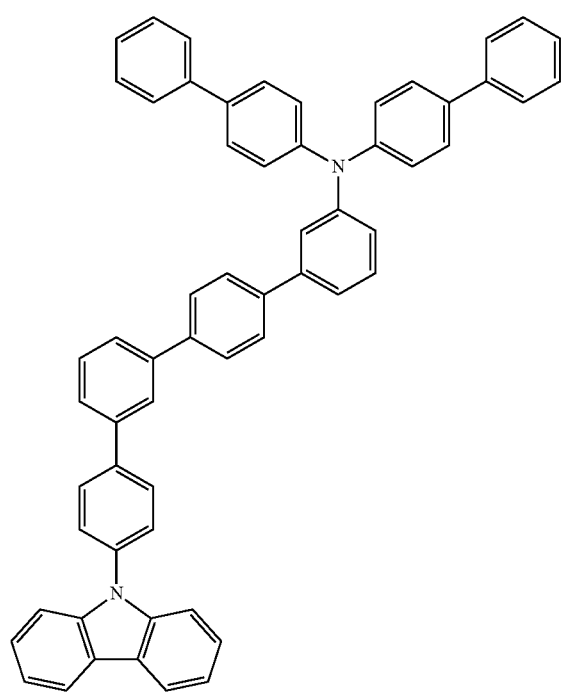 [SMILES: c1ccc(-c2ccc(N(c3ccc(-c4ccccc4)cc3)c3cccc(-c4ccc(-c5cccc(-c6ccc(-n7c8ccccc8c8ccccc87)cc6)c5)cc4)c3)cc2)cc1]
56

57
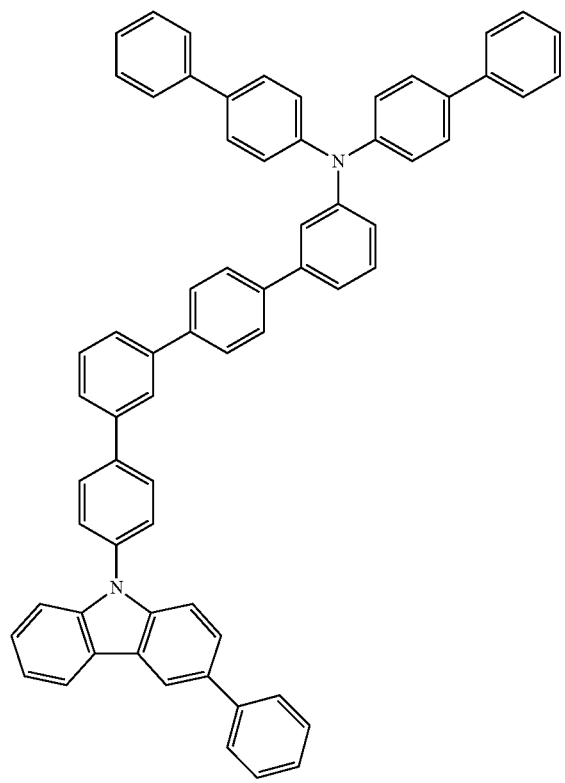 [SMILES: c1ccc(-c2ccc(N(c3ccc(-c4ccccc4)cc3)c3cccc(-c4ccc(-c5cccc(-c6ccc(-n7c8ccccc8c8cc(-c9ccccc9)ccc87)cc6)c5)cc4)c3)cc2)cc1]
58
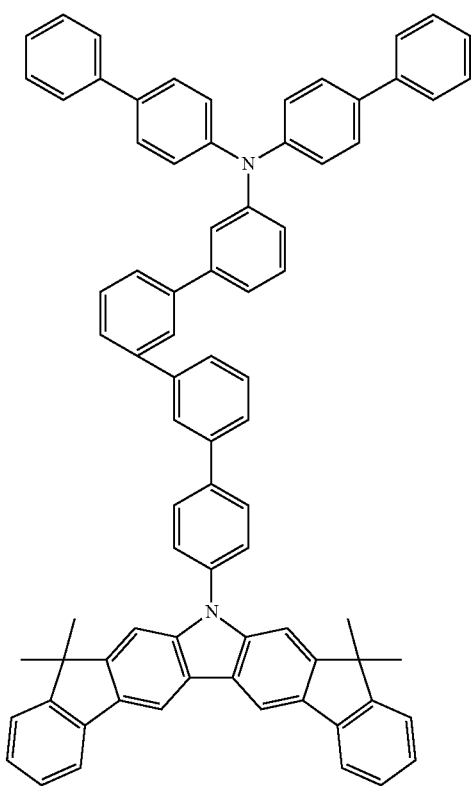 [SMILES: CC1(C)c2ccccc2-c2cc3c4cc5c(cc4n(-c4ccc(-c6cccc(-c7cccc(-c8cccc(N(c9ccc(-c%10ccccc%10)cc9)c9ccc(-c%10ccccc%10)cc9)c8)c7)c6)cc4)c3cc21)C(C)(C)c1ccccc1-5]

-continued
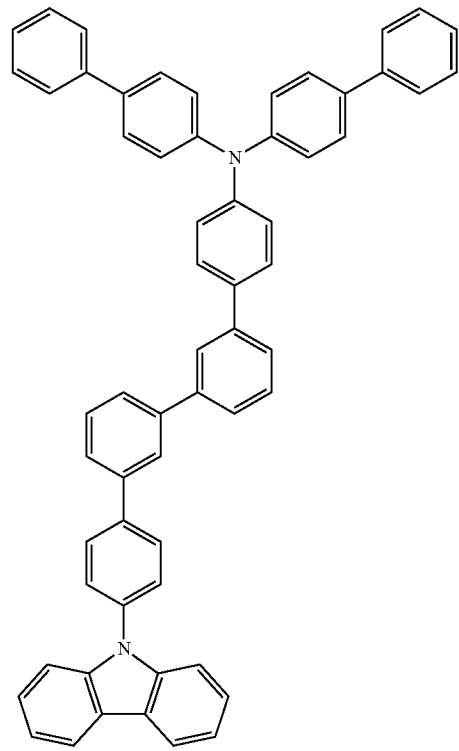 [SMILES: c1ccc(-c2ccc(N(c3ccc(-c4ccccc4)cc3)c3ccc(-c4cccc(-c5cccc(-c6ccc(-n7c8ccccc8c8ccccc87)cc6)c5)c4)cc3)cc2)cc1]
59
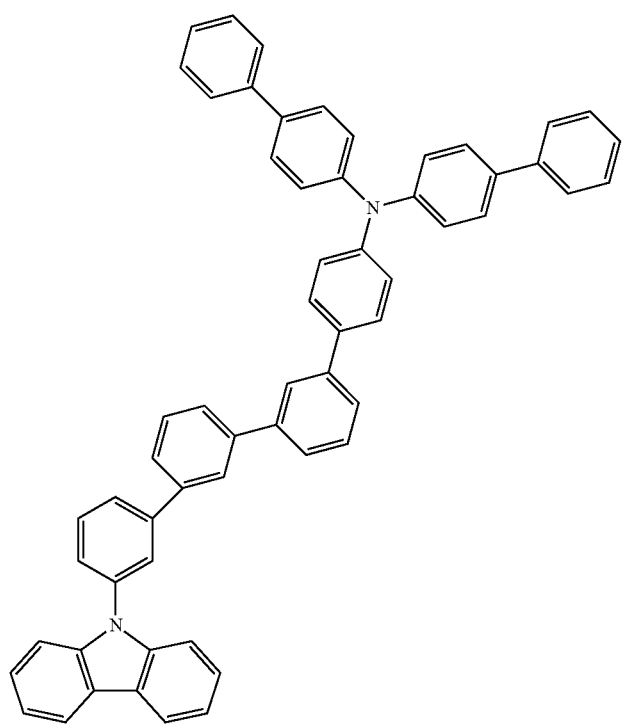 [SMILES: c1ccc(-c2ccc(N(c3ccc(-c4ccccc4)cc3)c3ccc(-c4cccc(-c5cccc(-c6cccc(-n7c8ccccc8c8ccccc87)c6)c5)c4)cc3)cc2)cc1]
60

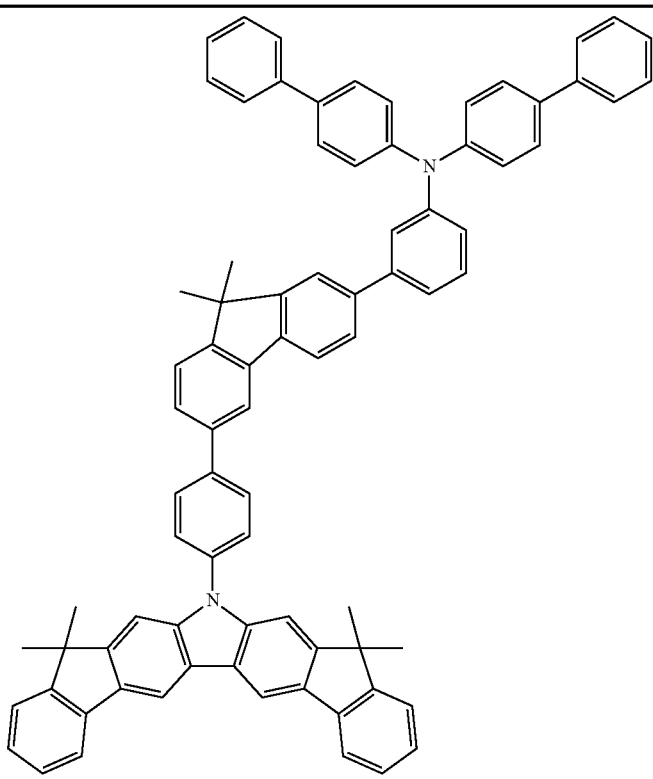
61
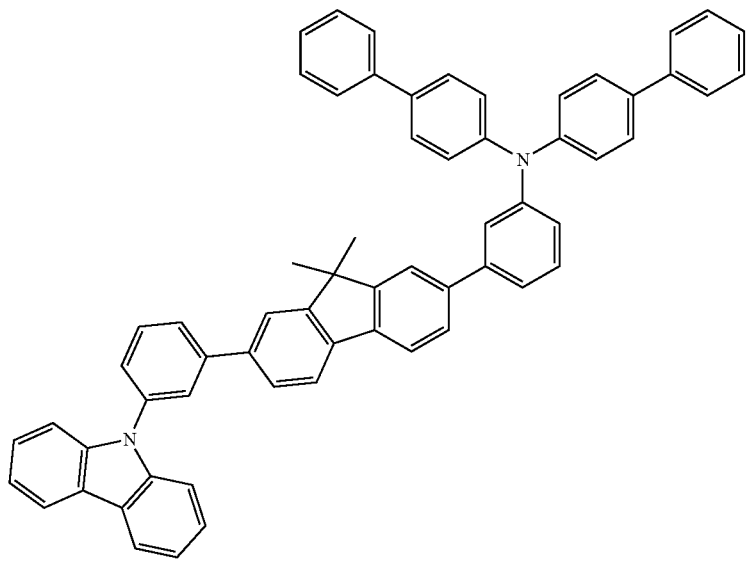 [SMILES: CC1(C)c2cc(-c3cccc(N(c4ccc(-c5ccccc5)cc4)c4ccc(-c5ccccc5)cc4)c3)ccc2-c2ccc(-c3cccc(-n4c5ccccc5c5ccccc54)c3)cc21]
62

63
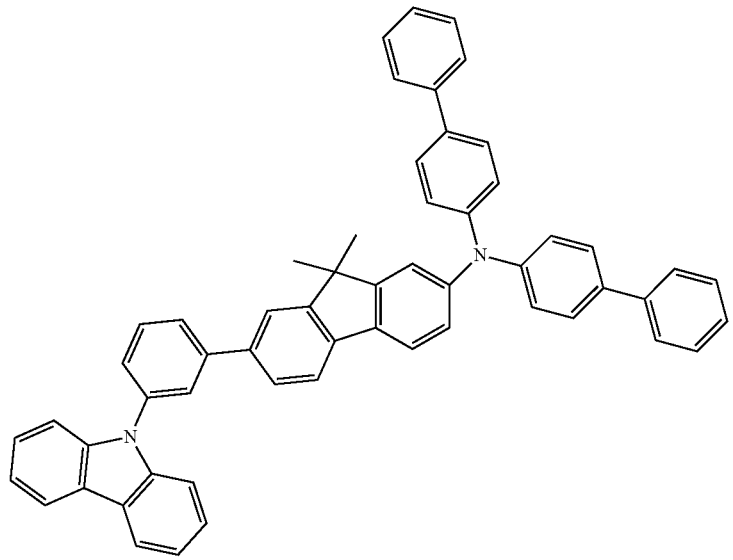 [SMILES: CC1(C)c2cc(-c3cccc(-n4c5ccccc5c5ccccc54)c3)ccc2-c2ccc(N(c3ccc(-c4ccccc4)cc3)c3ccc(-c4ccccc4)cc3)cc21]
64
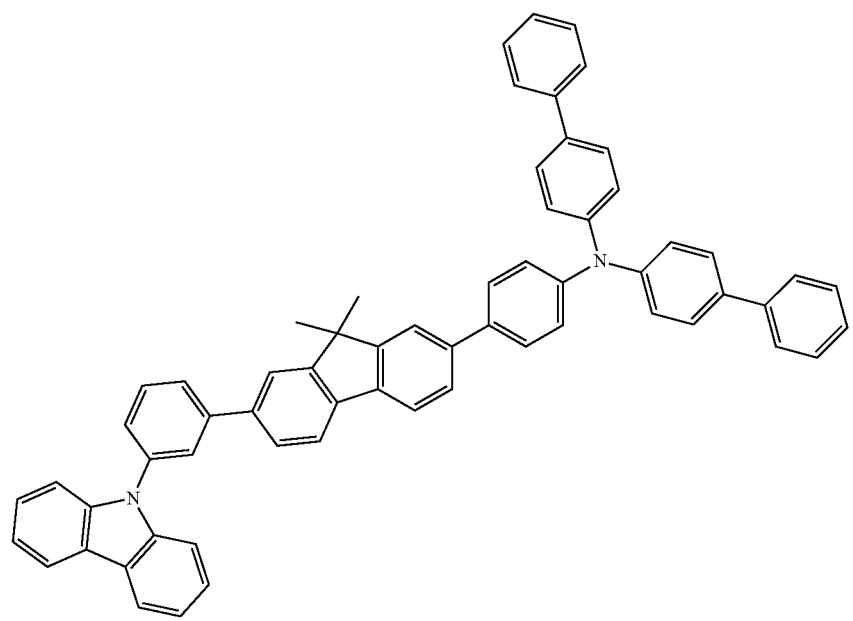 [SMILES: CC1(C)c2cc(-c3ccc(N(c4ccc(-c5ccccc5)cc4)c4ccc(-c5ccccc5)cc4)cc3)ccc2-c2ccc(-c3cccc(-n4c5ccccc5c5ccccc54)c3)cc21]
65
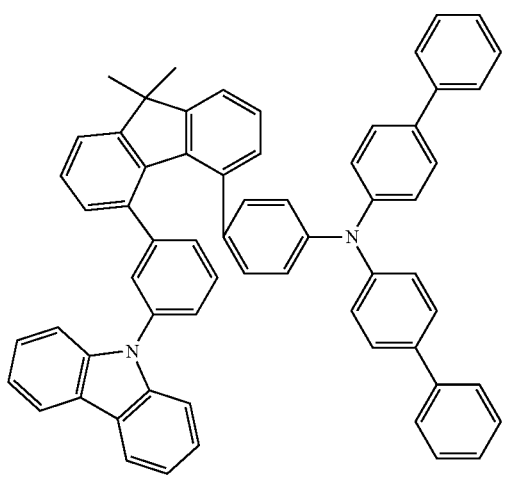 [SMILES: CC1(C)c2cccc(-c3ccc(N(c4ccc(-c5ccccc5)cc4)c4ccc(-c5ccccc5)cc4)cc3)c2-c2c(-c3cccc(-n4c5ccccc5c5ccccc54)c3)cccc21]

-continued
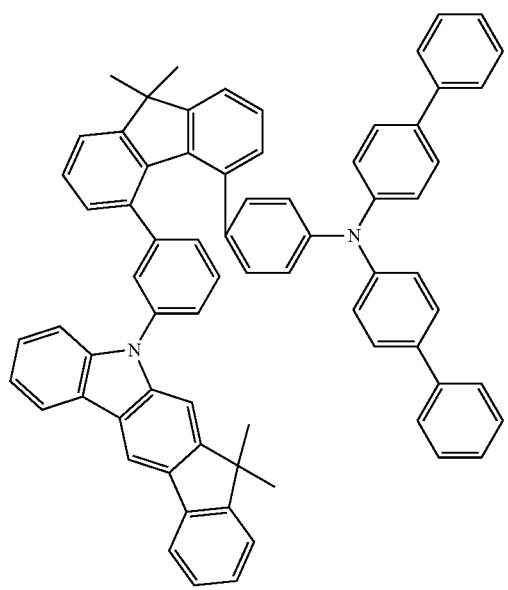 [SMILES: CC1(C)c2ccccc2-c2cc3c4ccccc4n(-c4cccc(-c5cccc6c5-c5c(-c7ccc(N(c8ccc(-c9ccccc9)cc8)c8ccc(-c9ccccc9)cc8)cc7)cccc5C6(C)C)c4)c3cc21]
66
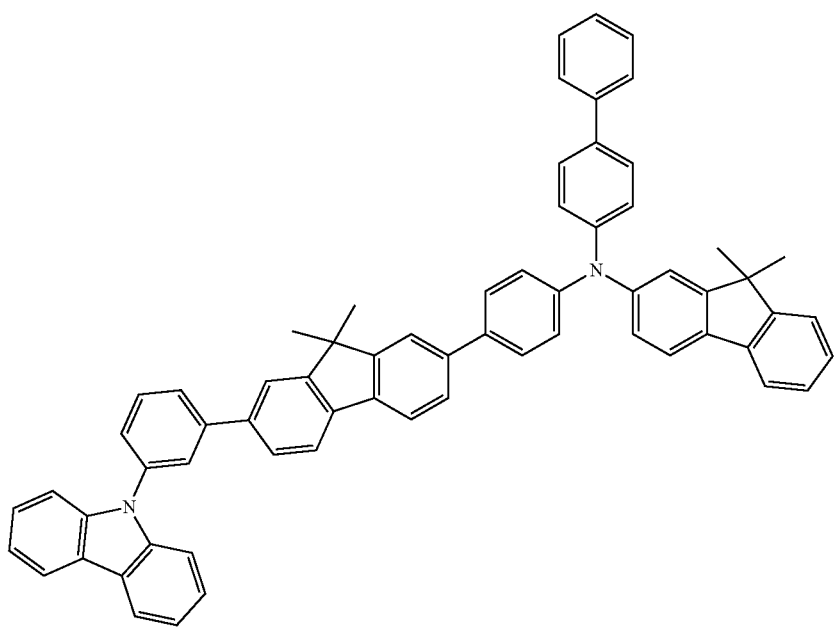 [SMILES: CC1(C)c2cc(-c3ccc(N(c4ccc(-c5ccccc5)cc4)c4ccc5c(c4)C(C)(C)c4ccccc4-5)cc3)ccc2-c2ccc(-c3cccc(-n4c5ccccc5c5ccccc54)c3)cc21]
67

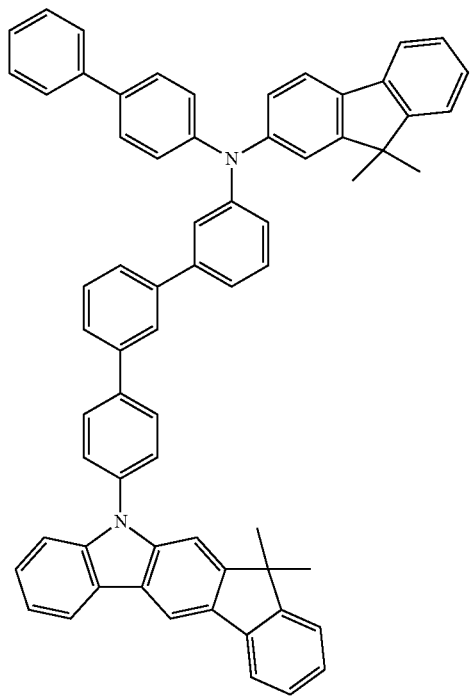 [SMILES: CC1(C)c2ccccc2-c2ccc(N(c3ccc(-c4ccccc4)cc3)c3cccc(-c4cccc(-c5ccc(-n6c7ccccc7c7cc8c(cc76)C(C)(C)c6ccccc6-8)cc5)c4)c3)cc21]
68
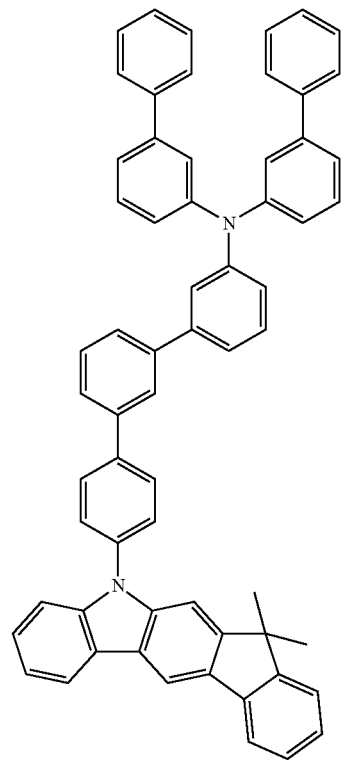 [SMILES: CC1(C)c2ccccc2-c2cc3c4ccccc4n(-c4ccc(-c5cccc(-c6cccc(N(c7cccc(-c8ccccc8)c7)c7cccc(-c8ccccc8)c7)c6)c5)cc4)c3cc21]
69

-continued
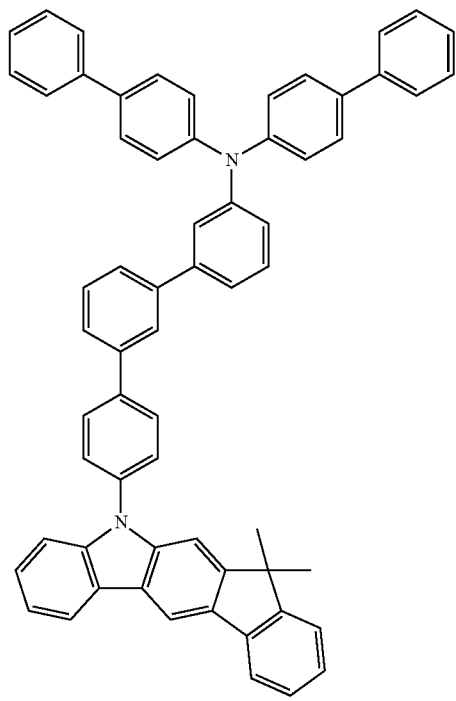 [SMILES: CC1(C)c2ccccc2-c2cc3c4ccccc4n(-c4ccc(-c5cccc(-c6cccc(N(c7ccc(-c8ccccc8)cc7)c7ccc(-c8ccccc8)cc7)c6)c5)cc4)c3cc21]
70
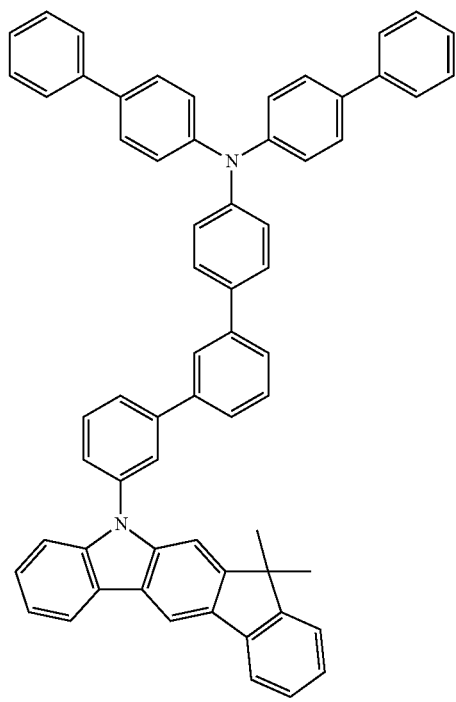 [SMILES: CC1(C)c2ccccc2-c2cc3c4ccccc4n(-c4cccc(-c5cccc(-c6ccc(N(c7ccc(-c8ccccc8)cc7)c7ccc(-c8ccccc8)cc7)cc6)c5)c4)c3cc21]
71

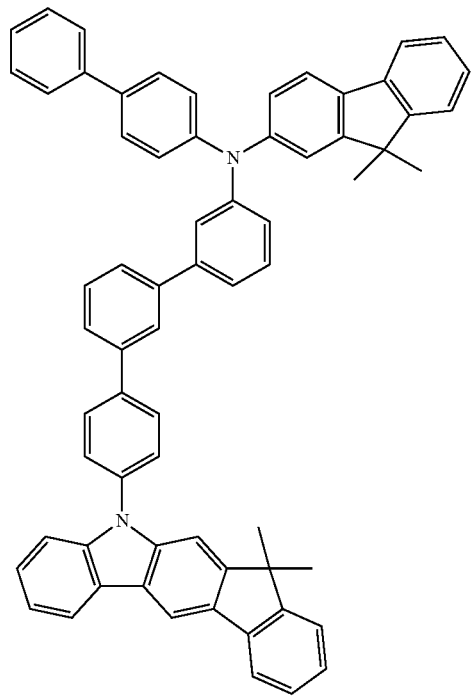
72